(12) United States Patent
Whitfield et al.

(10) Patent No.: US 7,905,890 B2
(45) Date of Patent: Mar. 15, 2011

(54) ENDOSCOPIC SURGICAL CLIP APPLIER

(75) Inventors: Kenneth H. Whitfield, New Haven, CT (US); Greg Sorrentino, Wallingford, CT (US)

(73) Assignee: Tyco Healthcare Group LP, Norwalk, CT (US)

( * ) Notice: Subject to any disclaimer, the term of this patent is extended or adjusted under 35 U.S.C. 154(b) by 49 days.

(21) Appl. No.: 11/245,528

(22) Filed: Oct. 7, 2005

(65) Prior Publication Data
US 2006/0079913 A1 Apr. 13, 2006

Related U.S. Application Data

(60) Provisional application No. 60/617,104, filed on Oct. 8, 2004, provisional application No. 60/617,016, filed on Oct. 8, 2004.

(51) Int. Cl.
*A61B 17/10* (2006.01)
(52) U.S. Cl. ...................................................... 606/142
(58) Field of Classification Search .................. 606/142, 606/143; 227/175.1, 175.2, 175.3, 175.4, 227/176.1, 178.1, 179.1, 19, 177.1, 182.1
See application file for complete search history.

(56) References Cited

U.S. PATENT DOCUMENTS

| | | | |
|---|---|---|---|
| 3,120,230 A | 2/1964 | Skold | |
| 3,638,847 A | 2/1972 | Noiles et al. | |
| 4,242,902 A | 1/1981 | Green | |
| 4,296,751 A | 10/1981 | Blake, III et al. | |
| 4,372,316 A | 2/1983 | Blake, III et al. | |
| 4,408,603 A | 10/1983 | Blake, III et al. | |
| 4,480,640 A | 11/1984 | Becht | |
| 4,480,641 A | 11/1984 | Failla et al. | |
| 4,487,204 A | 12/1984 | Hrouda | |
| 4,487,205 A | 12/1984 | Di Giovanni et al. | |
| 4,491,133 A | 1/1985 | Menges et al. | |
| 4,492,232 A | 1/1985 | Green | |
| 4,498,476 A | 2/1985 | Cerwin et al. | |
| 4,500,024 A | 2/1985 | DiGiovanni et al. | |

(Continued)

FOREIGN PATENT DOCUMENTS

EP 0 732 078 A2 9/1996

(Continued)

OTHER PUBLICATIONS

International Search Report for application EP 07 25 3905 date Feb. 7, 2008.

(Continued)

*Primary Examiner* — Eduardo C Robert
*Assistant Examiner* — Lindsey Bachman

(57) ABSTRACT

An apparatus for application of surgical clips to body tissue has a handle portion and a body extending distally from the handle portion and defining a longitudinal axis. The apparatus also has a plurality of surgical clips disposed within the body, and a jaw assembly mounted adjacent a distal end portion of the body. The jaw assembly includes first and second jaw portions movable between a spaced-apart and an approximated position. The apparatus also has a wedge plate longitudinally movable between the first and the second jaw portions, and a clip pusher configured to individually distally advance a surgical clip to the jaw assembly while the jaw portions are in the spaced apart position. The apparatus still further has an actuator at least partially disposed within the body and longitudinally movable in response to actuation of the handle portion and a jaw closure member positioned adjacent the first and second jaw portions to move the jaw portions to the approximated position.

12 Claims, 51 Drawing Sheets

U.S. PATENT DOCUMENTS

| | | | |
|---|---|---|---|
| 4,509,518 A | 4/1985 | McGarry et al. | |
| 4,512,345 A | 4/1985 | Green | |
| 4,522,207 A | 6/1985 | Klieman et al. | |
| 4,532,925 A | 8/1985 | Blake, III | |
| 4,534,351 A | 8/1985 | Rothfuss et al. | |
| 4,545,377 A | 10/1985 | Cerwin et al. | |
| 4,549,544 A | 10/1985 | Favaron | |
| 4,556,058 A | 12/1985 | Green | |
| 4,557,263 A | 12/1985 | Green | |
| 4,562,839 A | 1/1986 | Blake, III et al. | |
| 4,572,183 A | 2/1986 | Juska | |
| 4,576,165 A | 3/1986 | Green et al. | |
| 4,576,166 A | 3/1986 | Montgomery et al. | |
| 4,590,937 A | 5/1986 | Deniega | |
| 4,598,711 A | 7/1986 | Deniega | |
| 4,602,631 A | 7/1986 | Funatsu | |
| 4,611,595 A | 9/1986 | Klieman et al. | |
| 4,612,932 A | 9/1986 | Caspar et al. | |
| 4,616,650 A | 10/1986 | Green et al. | |
| 4,616,651 A | 10/1986 | Golden | |
| 4,624,254 A | 11/1986 | McGarry et al. | |
| 4,637,395 A | 1/1987 | Caspar et al. | |
| 4,646,740 A | 3/1987 | Peters et al. | |
| 4,647,504 A | 3/1987 | Kimimura et al. | |
| 4,658,822 A | 4/1987 | Kees, Jr. | |
| 4,660,558 A | 4/1987 | Kees, Jr. | |
| 4,662,373 A | 5/1987 | Montgomery et al. | |
| 4,662,374 A | 5/1987 | Blake, III | |
| 4,671,278 A | 6/1987 | Chin | |
| 4,671,282 A | 6/1987 | Tretbar | |
| 4,674,504 A | 6/1987 | Klieman et al. | |
| 4,681,107 A | 7/1987 | Kees, Jr. | |
| 4,696,396 A | 9/1987 | Samuels | |
| 4,702,247 A | 10/1987 | Blake, III et al. | |
| 4,706,668 A | 11/1987 | Backer | |
| 4,712,549 A | 12/1987 | Peters et al. | |
| 4,733,664 A | 3/1988 | Kirsch et al. | |
| 4,733,666 A | 3/1988 | Mercer, Jr. | |
| 4,759,364 A | 7/1988 | Boebel | |
| 4,765,335 A | 8/1988 | Schmidt et al. | |
| 4,777,949 A | 10/1988 | Perlin | |
| 4,777,950 A | 10/1988 | Kees, Jr. | |
| 4,796,625 A | 1/1989 | Kees, Jr. | |
| 4,799,481 A | 1/1989 | Transue et al. | |
| 4,815,466 A | 3/1989 | Perlin | |
| 4,817,604 A | 4/1989 | Smith, III | |
| 4,821,721 A | 4/1989 | Chin et al. | |
| 4,822,348 A | 4/1989 | Casey | |
| 4,827,930 A | 5/1989 | Kees, Jr. | |
| 4,834,096 A | 5/1989 | Oh et al. | |
| 4,850,355 A | 7/1989 | Brooks et al. | |
| 4,854,317 A | 8/1989 | Braun | |
| 4,856,517 A | 8/1989 | Collins et al. | |
| 4,929,239 A | 5/1990 | Braun | |
| 4,929,240 A | 5/1990 | Kirsch et al. | |
| 4,931,058 A | 6/1990 | Cooper | |
| 4,932,955 A | 6/1990 | Merz et al. | |
| 4,934,364 A | 6/1990 | Green | |
| 4,943,298 A | 7/1990 | Fujita et al. | |
| 4,957,500 A | 9/1990 | Liang et al. | |
| 4,966,603 A | 10/1990 | Focelle et al. | |
| 4,967,949 A | 11/1990 | Sandhaus | |
| 4,983,176 A | 1/1991 | Cushman et al. | |
| 4,988,355 A | 1/1991 | Leveen et al. | |
| 5,002,552 A | 3/1991 | Casey | |
| 5,026,379 A | 6/1991 | Yoon | |
| 5,030,224 A | 7/1991 | Wright et al. | |
| 5,030,226 A | 7/1991 | Green et al. | |
| 5,032,127 A | 7/1991 | Frazee et al. | |
| 5,035,692 A | 7/1991 | Lyon et al. | |
| 5,047,038 A | 9/1991 | Peters et al. | |
| 5,049,152 A * | 9/1991 | Simon et al. | 606/143 |
| 5,049,153 A | 9/1991 | Nakao et al. | |
| 5,053,045 A | 10/1991 | Schmidt et al. | |
| 5,059,202 A | 10/1991 | Liang et al. | |
| 5,062,846 A | 11/1991 | Oh et al. | |
| 5,078,731 A | 1/1992 | Hayhurst | |
| 5,084,057 A | 1/1992 | Green et al. | |
| 5,100,416 A | 3/1992 | Oh et al. | |
| 5,100,420 A | 3/1992 | Green et al. | |
| 5,104,394 A | 4/1992 | Knoepfler | |
| 5,104,395 A | 4/1992 | Thornton et al. | |
| 5,112,343 A | 5/1992 | Thornton | |
| 5,122,150 A | 6/1992 | Puig | |
| 5,127,915 A | 7/1992 | Mattson | |
| 5,129,885 A | 7/1992 | Green et al. | |
| 5,156,608 A | 10/1992 | Troidl et al. | |
| 5,160,339 A | 11/1992 | Chen et al. | |
| 5,163,945 A | 11/1992 | Ortiz et al. | |
| 5,171,247 A | 12/1992 | Hughett et al. | |
| 5,171,249 A | 12/1992 | Stefanchik et al. | |
| 5,171,250 A | 12/1992 | Yoon | |
| 5,171,251 A | 12/1992 | Bregen et al. | |
| 5,171,252 A | 12/1992 | Friedland | |
| 5,171,253 A | 12/1992 | Klieman | |
| 5,192,288 A | 3/1993 | Thompson et al. | |
| 5,197,970 A | 3/1993 | Green et al. | |
| 5,199,566 A | 4/1993 | Ortiz et al. | |
| 5,201,746 A | 4/1993 | Shichman | |
| 5,201,900 A | 4/1993 | Nardella | |
| 5,207,691 A | 5/1993 | Nardella | |
| 5,207,692 A | 5/1993 | Kraus et al. | |
| 5,217,473 A | 6/1993 | Yoon | |
| 5,219,353 A | 6/1993 | Garvey, III et al. | |
| 5,246,450 A | 9/1993 | Thornton et al. | |
| 5,269,792 A | 12/1993 | Kovac et al. | |
| 5,281,228 A | 1/1994 | Wolfson | |
| 5,282,807 A | 2/1994 | Knoepfler | |
| 5,282,808 A | 2/1994 | Kovac et al. | |
| 5,282,832 A | 2/1994 | Toso et al. | |
| 5,289,963 A * | 3/1994 | McGarry et al. | 227/175.1 |
| 5,290,299 A | 3/1994 | Fain et al. | |
| 5,300,081 A * | 4/1994 | Young et al. | 606/143 |
| 5,304,183 A | 4/1994 | Gourlay et al. | |
| 5,306,280 A | 4/1994 | Bregen et al. | |
| 5,306,283 A | 4/1994 | Conners | |
| 5,312,426 A | 5/1994 | Segawa et al. | |
| 5,330,442 A | 7/1994 | Green et al. | |
| 5,330,487 A | 7/1994 | Thornton et al. | |
| 5,340,360 A | 8/1994 | Stefanchik | |
| 5,342,373 A | 8/1994 | Stefanchik et al. | |
| 5,354,304 A | 10/1994 | Allen et al. | |
| 5,354,306 A | 10/1994 | Garvey, III et al. | |
| 5,366,458 A | 11/1994 | Korthoff et al. | |
| 5,366,459 A | 11/1994 | Yoon | |
| 5,368,600 A | 11/1994 | Failla et al. | |
| 5,382,253 A | 1/1995 | Hogendijk | |
| 5,382,255 A | 1/1995 | Castro et al. | |
| 5,383,881 A | 1/1995 | Green et al. | |
| 5,395,375 A | 3/1995 | Turkel et al. | |
| 5,395,381 A | 3/1995 | Green et al. | |
| 5,403,327 A | 4/1995 | Thornton et al. | |
| 5,409,498 A | 4/1995 | Braddock et al. | |
| 5,413,584 A | 5/1995 | Scjulze | |
| 5,423,835 A | 6/1995 | Green et al. | |
| 5,425,740 A | 6/1995 | Hutchinson, Jr. | |
| 5,431,667 A | 7/1995 | Thompson et al. | |
| 5,431,668 A | 7/1995 | Burbank, III et al. | |
| 5,431,669 A | 7/1995 | Thompson et al. | |
| 5,439,468 A | 8/1995 | Schulze et al. | |
| 5,441,509 A | 8/1995 | Vidal et al. | |
| 5,447,513 A | 9/1995 | Davison et al. | |
| 5,449,365 A | 9/1995 | Green et al. | |
| 5,462,555 A | 10/1995 | Bolanos et al. | |
| 5,462,558 A | 10/1995 | Kolesa et al. | |
| 5,464,416 A | 11/1995 | Steckel | |
| 5,474,566 A | 12/1995 | Alesi et al. | |
| 5,474,567 A | 12/1995 | Stefanchik et al. | |
| 5,474,572 A | 12/1995 | Hayhurst | |
| 5,487,746 A | 1/1996 | Yu et al. | |
| 5,501,693 A | 3/1996 | Gravener | |
| 5,509,920 A | 4/1996 | Phillips et al. | |
| 5,514,149 A | 5/1996 | Green et al. | |
| 5,520,701 A | 5/1996 | Lerch | |
| 5,522,823 A | 6/1996 | Kuntz et al. | |
| 5,527,318 A | 6/1996 | McGarry | |
| 5,527,319 A | 6/1996 | Green et al. | |

| | | | | | |
|---|---|---|---|---|---|
| 5,527,320 A | 6/1996 | Carruthers et al. | 5,913,862 A | 6/1999 | Ramsey et al. |
| 5,542,949 A | 8/1996 | Yoon | 5,918,791 A | 7/1999 | Sorrentino et al. |
| 5,547,474 A | 8/1996 | Kloeckl et al. | 5,921,996 A | 7/1999 | Sherman |
| 5,569,274 A | 10/1996 | Rapacki et al. | 5,921,997 A | 7/1999 | Fogelberg et al. |
| 5,571,121 A | 11/1996 | Heifetz | 5,928,251 A | 7/1999 | Aranyi et al. |
| 5,575,802 A | 11/1996 | McQuildin et al. | 5,938,667 A * | 8/1999 | Peyser et al. .................. 606/142 |
| 5,582,615 A | 12/1996 | Foshee et al. | 5,951,574 A | 9/1999 | Stefanchik et al. |
| 5,584,840 A | 12/1996 | Ramsey et al. | 5,972,003 A | 10/1999 | Rousseau et al. |
| 5,591,178 A | 1/1997 | Green et al. | 5,976,159 A | 11/1999 | Bolduc et al. |
| 5,593,414 A | 1/1997 | Shipp et al. | 5,993,465 A | 11/1999 | Shipp et al. |
| 5,593,421 A | 1/1997 | Bauer | 6,004,335 A | 12/1999 | Vaitekunas et al. |
| 5,601,573 A | 2/1997 | Fogelberg et al. | 6,017,358 A | 1/2000 | Yoon et al. |
| 5,601,574 A | 2/1997 | Stefanchik et al. | RE36,720 E | 5/2000 | Green et al. |
| 5,607,436 A | 3/1997 | Pratt et al. | 6,059,799 A * | 5/2000 | Aranyi et al. .................. 606/143 |
| 5,618,291 A | 4/1997 | Thompson et al. | 6,099,536 A | 8/2000 | Petillo |
| 5,618,306 A | 4/1997 | Roth et al. | 6,099,537 A | 8/2000 | Sugai et al. |
| 5,620,452 A | 4/1997 | Yoon | 6,139,555 A | 10/2000 | Hart et al. |
| 5,626,585 A | 5/1997 | Mittelstadt et al. | 6,210,418 B1 | 4/2001 | Storz et al. |
| 5,626,586 A | 5/1997 | Pistl et al. | 6,217,590 B1 | 4/2001 | Levinson |
| 5,626,592 A | 5/1997 | Phillips et al. | 6,228,097 B1 | 5/2001 | Levinson et al. |
| RE35,525 E | 6/1997 | Stefanchik et al. | 6,241,740 B1 | 6/2001 | Davis et al. |
| 5,634,930 A | 6/1997 | Thornton et al. | 6,258,105 B1 | 7/2001 | Hart et al. |
| 5,643,291 A | 7/1997 | Pier et al. | 6,261,302 B1 | 7/2001 | Voegele et al. |
| 5,645,551 A | 7/1997 | Green et al. | 6,273,898 B1 | 8/2001 | Kienzle et al. |
| 5,645,553 A | 7/1997 | Kolesa et al. | 6,277,131 B1 | 8/2001 | Kalikow |
| 5,649,937 A | 7/1997 | Bito et al. | 6,306,149 B1 | 10/2001 | Meade |
| 5,653,720 A | 8/1997 | Johnson et al. | 6,318,619 B1 | 11/2001 | Lee |
| 5,662,676 A | 9/1997 | Koninckx | 6,322,571 B1 | 11/2001 | Adams |
| 5,662,679 A | 9/1997 | Voss et al. | 6,350,269 B1 | 2/2002 | Shipp et al. |
| 5,665,097 A | 9/1997 | Baker et al. | 6,352,541 B1 | 3/2002 | Kienzle et al. |
| 5,676,676 A | 10/1997 | Porter | 6,391,035 B1 | 5/2002 | Appleby et al. |
| 5,681,330 A | 10/1997 | Hughett et al. | 6,423,079 B1 | 7/2002 | Blake, III |
| 5,683,405 A | 11/1997 | Yacoubian et al. | 6,428,548 B1 | 8/2002 | Durgin et al. |
| 5,695,502 A | 12/1997 | Pier et al. | 6,440,144 B1 | 8/2002 | Bacher |
| 5,695,505 A | 12/1997 | Yoon | 6,461,363 B1 | 10/2002 | Gadberry et al. |
| 5,697,938 A | 12/1997 | Jensen et al. | 6,464,710 B1 | 10/2002 | Foster |
| 5,700,270 A | 12/1997 | Peyser et al. | 6,494,886 B1 | 12/2002 | Wilk et al. |
| 5,700,271 A | 12/1997 | Whitfield et al. | 6,517,536 B2 | 2/2003 | Hooven et al. |
| 5,702,048 A | 12/1997 | Eberlin | 6,520,972 B2 | 2/2003 | Peters |
| 5,709,706 A | 1/1998 | Kienzle et al. | 6,527,786 B1 | 3/2003 | Davis et al. |
| 5,713,911 A | 2/1998 | Racenet et al. | 6,537,289 B1 | 3/2003 | Kayan et al. |
| 5,713,912 A | 2/1998 | Porter | 6,546,935 B2 | 4/2003 | Hooven |
| 5,720,756 A | 2/1998 | Green et al. | 6,551,333 B2 | 4/2003 | Kuhns et al. |
| 5,722,982 A | 3/1998 | Ferreira et al. | 6,569,171 B2 | 5/2003 | DeGuillebon et al. |
| 5,725,537 A | 3/1998 | Green et al. | 6,579,304 B1 | 6/2003 | Hart et al. |
| 5,725,538 A | 3/1998 | Green et al. | 6,599,298 B1 | 7/2003 | Forster et al. |
| 5,725,542 A | 3/1998 | Yoon | 6,602,252 B2 | 8/2003 | Mollenauer |
| 5,733,295 A | 3/1998 | Back et al. | 6,607,540 B1 | 8/2003 | Shipp |
| 5,755,726 A | 5/1998 | Pratt et al. | 6,613,060 B2 | 9/2003 | Adams et al. |
| 5,766,189 A | 6/1998 | Matsuno | 6,626,916 B1 | 9/2003 | Yeung et al. |
| 5,769,857 A | 6/1998 | Reztzov et al. | 6,626,922 B1 | 9/2003 | Hart et al. |
| 5,772,673 A | 6/1998 | Cuny et al. | 6,648,898 B1 | 11/2003 | Baxter |
| 5,776,146 A | 7/1998 | Sackier et al. | 6,652,538 B2 | 11/2003 | Kayan et al. |
| 5,776,147 A | 7/1998 | Dolendo | 6,652,539 B2 | 11/2003 | Shipp et al. |
| 5,779,718 A | 7/1998 | Green et al. | 6,673,083 B1 | 1/2004 | Kayan et al. |
| 5,779,720 A | 7/1998 | Walder-Utz et al. | 6,676,659 B2 | 1/2004 | Hutchins et al. |
| 5,782,844 A | 7/1998 | Yoon et al. | 6,679,894 B2 | 1/2004 | Damarati |
| 5,788,698 A | 8/1998 | Savornin | RE38,445 E | 2/2004 | Pistl et al. |
| 5,792,149 A | 8/1998 | Sherts et al. | 6,695,854 B2 | 2/2004 | Kayan et al. |
| 5,792,150 A | 8/1998 | Pratt et al. | 6,706,057 B1 | 3/2004 | Bidoia et al. |
| 5,797,922 A | 8/1998 | Hessel et al. | 6,716,226 B2 | 4/2004 | Sixto, Jr. et al. |
| 5,810,853 A | 9/1998 | Yoon | 6,723,109 B2 | 4/2004 | Solingen |
| 5,817,116 A | 10/1998 | Takahashi et al. | 6,743,240 B2 | 6/2004 | Smith et al. |
| 5,827,306 A | 10/1998 | Yoon | 6,773,438 B1 | 8/2004 | Knodel et al. |
| 5,833,695 A | 11/1998 | Yoon | 6,773,440 B2 | 8/2004 | Gannoe et al. |
| 5,833,696 A | 11/1998 | Whitfield et al. | 6,776,783 B1 | 8/2004 | Frantzen et al. |
| 5,833,700 A | 11/1998 | Fogelberg et al. | 6,776,784 B2 | 8/2004 | Ginn |
| 5,843,097 A | 12/1998 | Mayenberger et al. | 6,780,195 B2 | 8/2004 | Porat |
| 5,843,101 A | 12/1998 | Fry | 6,793,663 B2 | 9/2004 | Kneifel et al. |
| 5,846,255 A | 12/1998 | Casey | 6,793,664 B2 | 9/2004 | Mazzocchi et al. |
| 5,849,019 A | 12/1998 | Yoon | 6,802,848 B2 | 10/2004 | Anderson et al. |
| 5,858,018 A | 1/1999 | Shipp et al. | 6,814,742 B2 | 11/2004 | Kimura et al. |
| 5,861,005 A | 1/1999 | Kontos | 6,818,009 B2 | 11/2004 | Hart et al. |
| 5,868,759 A | 2/1999 | Peyser et al. | 6,821,273 B2 | 11/2004 | Mollenauer |
| 5,868,761 A | 2/1999 | Nicholas et al. | 6,821,284 B2 | 11/2004 | Sturtz et al. |
| 5,876,410 A | 3/1999 | Petillo | 6,824,547 B2 | 11/2004 | Wilson, Jr. et al. |
| 5,895,394 A | 4/1999 | Kienzle et al. | 6,824,548 B2 | 11/2004 | Smith et al. |
| 5,897,565 A | 4/1999 | Foster | 6,835,199 B2 | 12/2004 | McGuckin, Jr. et al. |
| 5,904,693 A | 5/1999 | Dicesare et al. | 6,835,200 B2 | 12/2004 | Laufer et al. |

| | | |
|---|---|---|
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 * | 5/2006 | Hughett .................. 606/142 |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,696 B2 | 1/2008 | Wilson, Jr. et al. |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |
| 2004/0138681 A1 | 7/2004 | Pier |
| 2004/0153100 A1 | 8/2004 | Ahlberg et al. |
| 2005/0080440 A1 | 4/2005 | Durgin et al. |
| 2005/0085830 A1 | 4/2005 | Lehman et al. |
| 2005/0090837 A1 | 4/2005 | Sixto, Jr. et al. |
| 2005/0090838 A1 | 4/2005 | Sixto, Jr. et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake, III et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |

| | | |
|---|---|---|
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0100649 A1 | 5/2006 | Hart |
| 2006/0111731 A1 | 5/2006 | Manzo |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson, Jr. et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | De La Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093856 A1 | 4/2007 | Whitfield |
| 2007/0106314 A1 | 5/2007 | Dunn |
| 2007/0112365 A1 | 5/2007 | Hilal et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto, Jr. et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr et al. |
| 2007/0282355 A1 | 12/2007 | Brown et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |

FOREIGN PATENT DOCUMENTS

| | | |
|---|---|---|
| EP | 0 755 655 A | 1/1997 |
| EP | 0 769 275 | 4/1997 |
| EP | 0769274 | 4/1997 |
| EP | 0 834 286 | 4/1998 |
| EP | 1 317 906 | 6/2003 |
| EP | 1 609 427 A1 | 12/2005 |
| EP | 1 712 191 A2 | 10/2006 |
| EP | 1 813 199 A1 | 8/2007 |
| EP | 1 908 423 A | 4/2008 |
| EP | 1 913 881 A1 | 4/2008 |
| WO | WO 2005/091457 | 9/2005 |
| WO | WO 2006/042076 | 4/2006 |
| WO | WO 2006/042084 | 4/2006 |
| WO | WO 2006/042110 | 4/2006 |
| WO | WO 2008/118928 A2 | 10/2008 |
| WO | WO 2008/127968 A | 10/2008 |

OTHER PUBLICATIONS

Extended European Search Report from Application No. EP 07 25 3807 mailed Nov. 26, 2008.

European Search Report corresponding to EP 09252053; date of mailing is Dec. 1, 2009; date of completion of Search is Nov. 24, 2009 (3 Pages).

European Search Report corresponding to EP 09252051; date of mailing is Jan. 28, 2010; date of completion of Search is Dec. 21, 2009 (3 Pages).

European Search Report corresponding to EP 09252050; date of mailing is Jan. 21, 2010; date of completion of Search is Dec. 23, 2009 (3 Pages).

European Search Report corresponding to EP 09252054; date of mailing is Jan. 22, 2010; date of completion of Search is Jan. 7, 2010 (3 Pages).

Extended European Search Report corresponding to EP 09252056.8, date of mailing is Feb. 5, 2010; date of completion of Search is Jan. 8, 2010 (3 Pages).

Extended European Search Report corresponding to EP 10250497.4, date of mailing is May 12, 2010; date of completion of Search is May 4, 2010 (6 Pages).

International Search Report from European Application No. EP 07 25 3807 mailed Aug. 1, 2008.

International Search Report from PCT Application No. PCT/US08/58185 dated Sep. 9, 2008.

International Search Report from PCT Application No. PCT/US08/59859 dated Sep. 18, 2008.

* cited by examiner

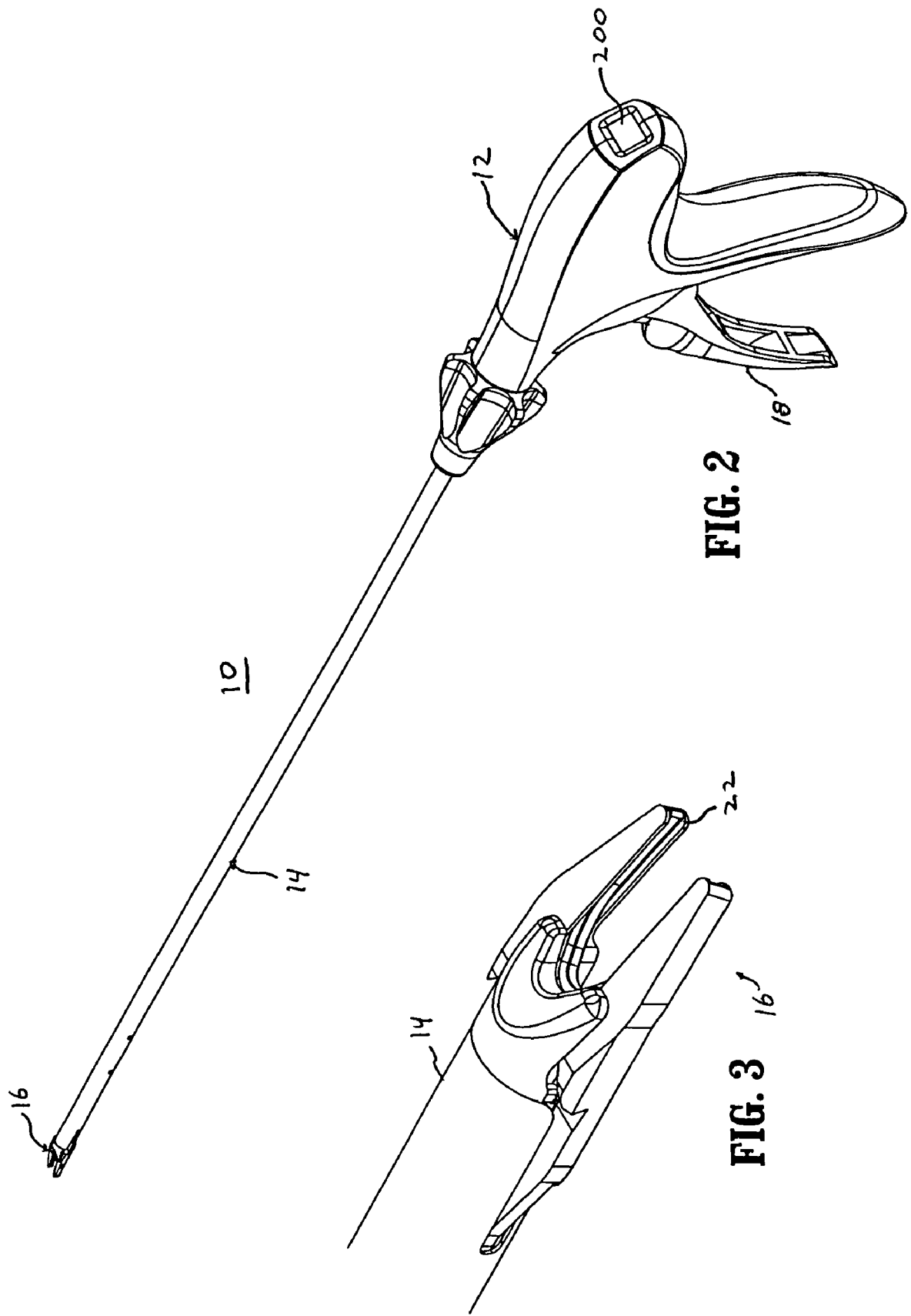

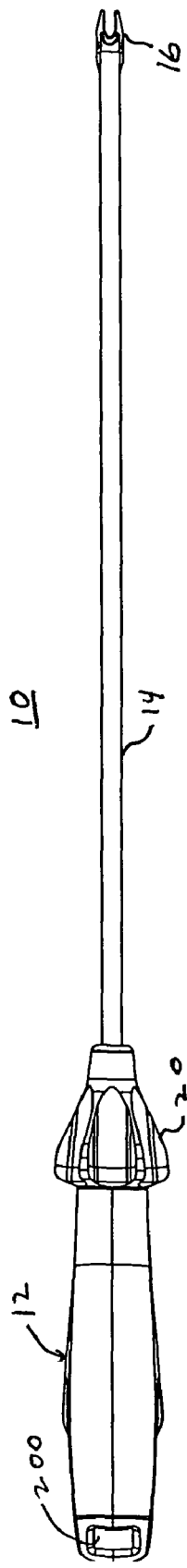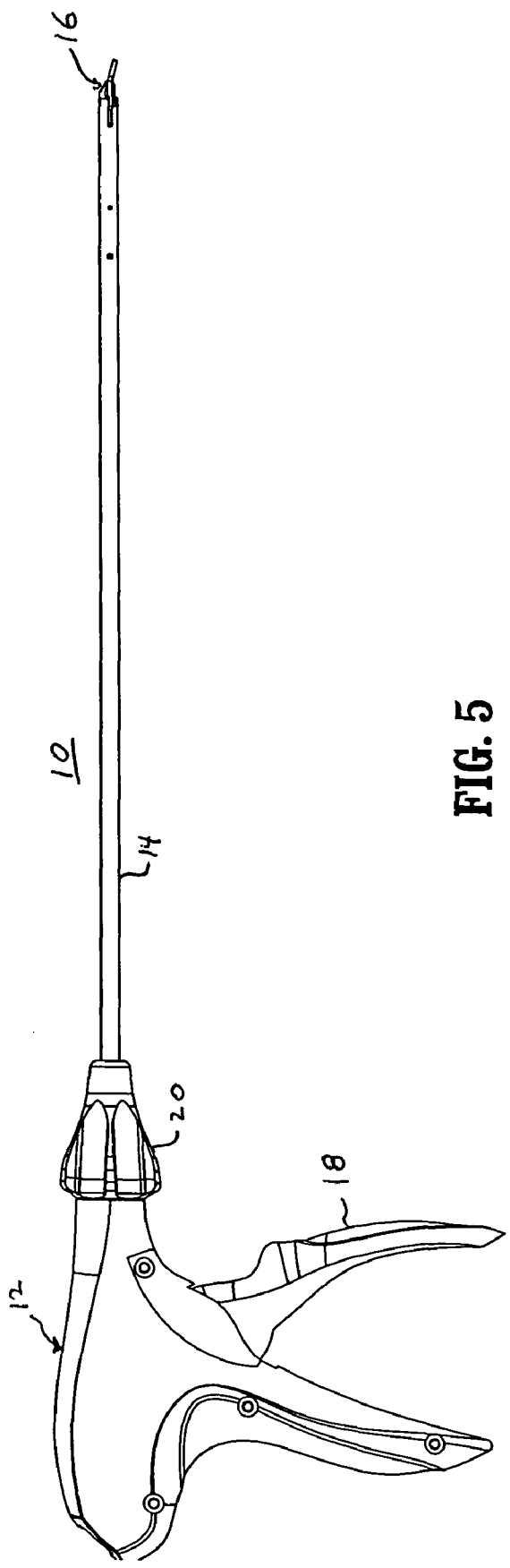
FIG. 4
FIG. 5

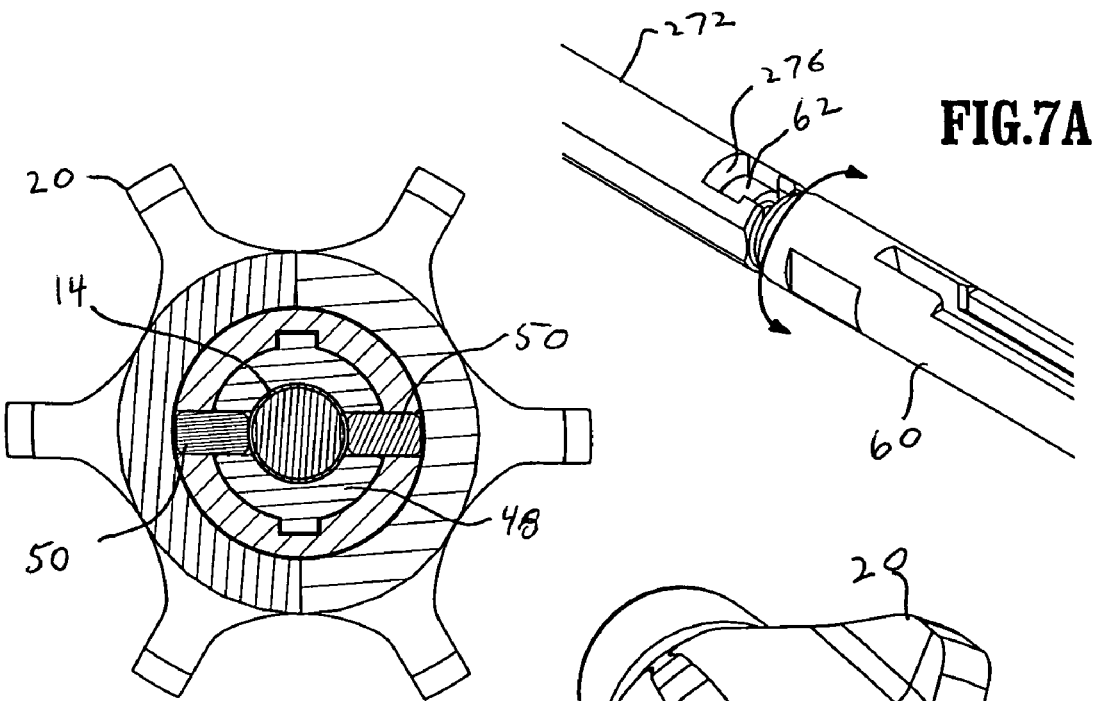
FIG. 7A
FIG. 7B
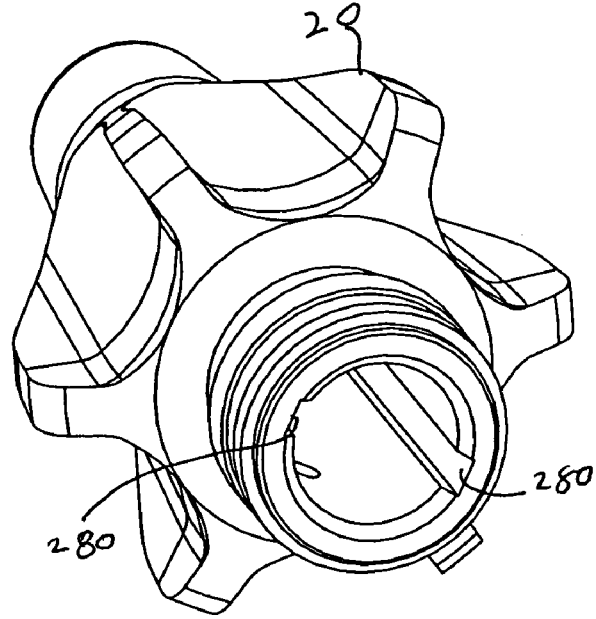
FIG. 7C
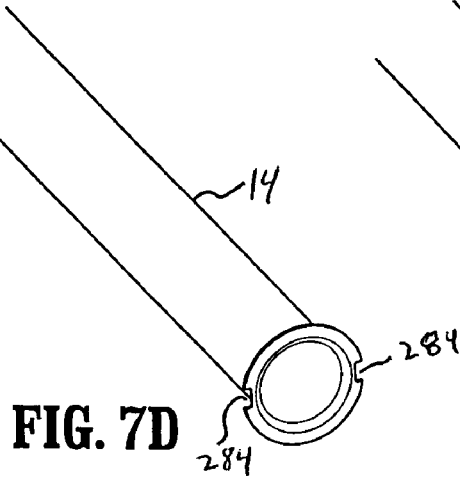
FIG. 7D
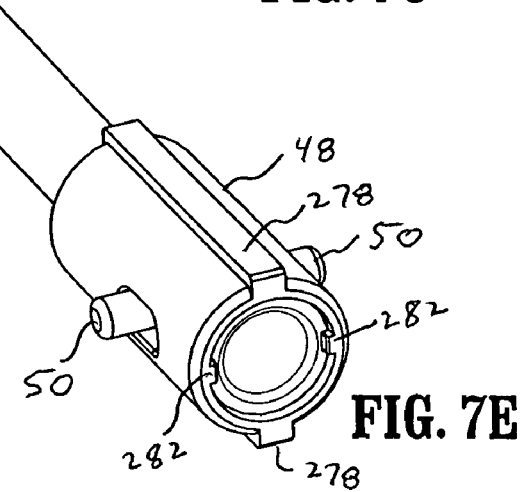
FIG. 7E

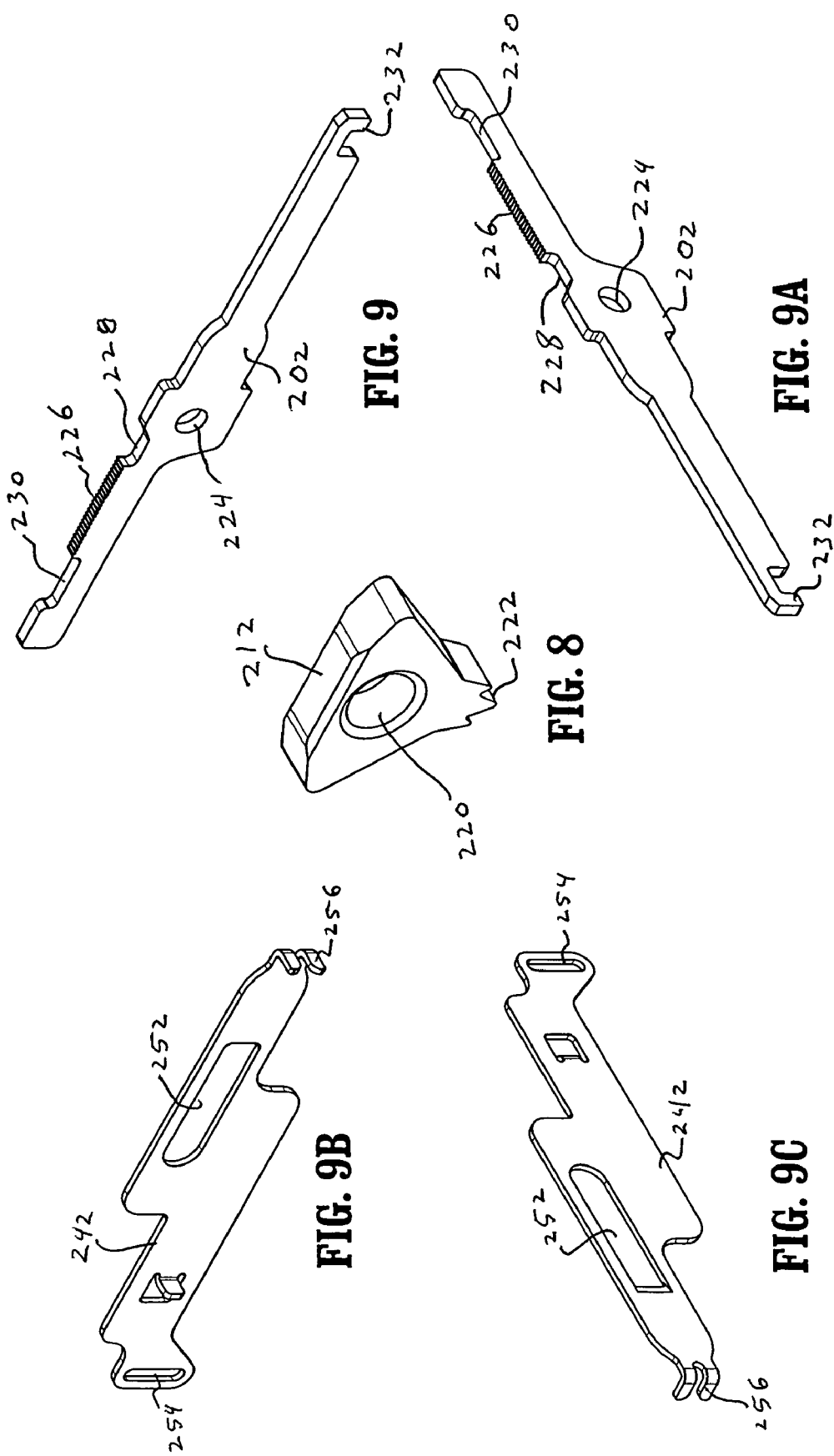

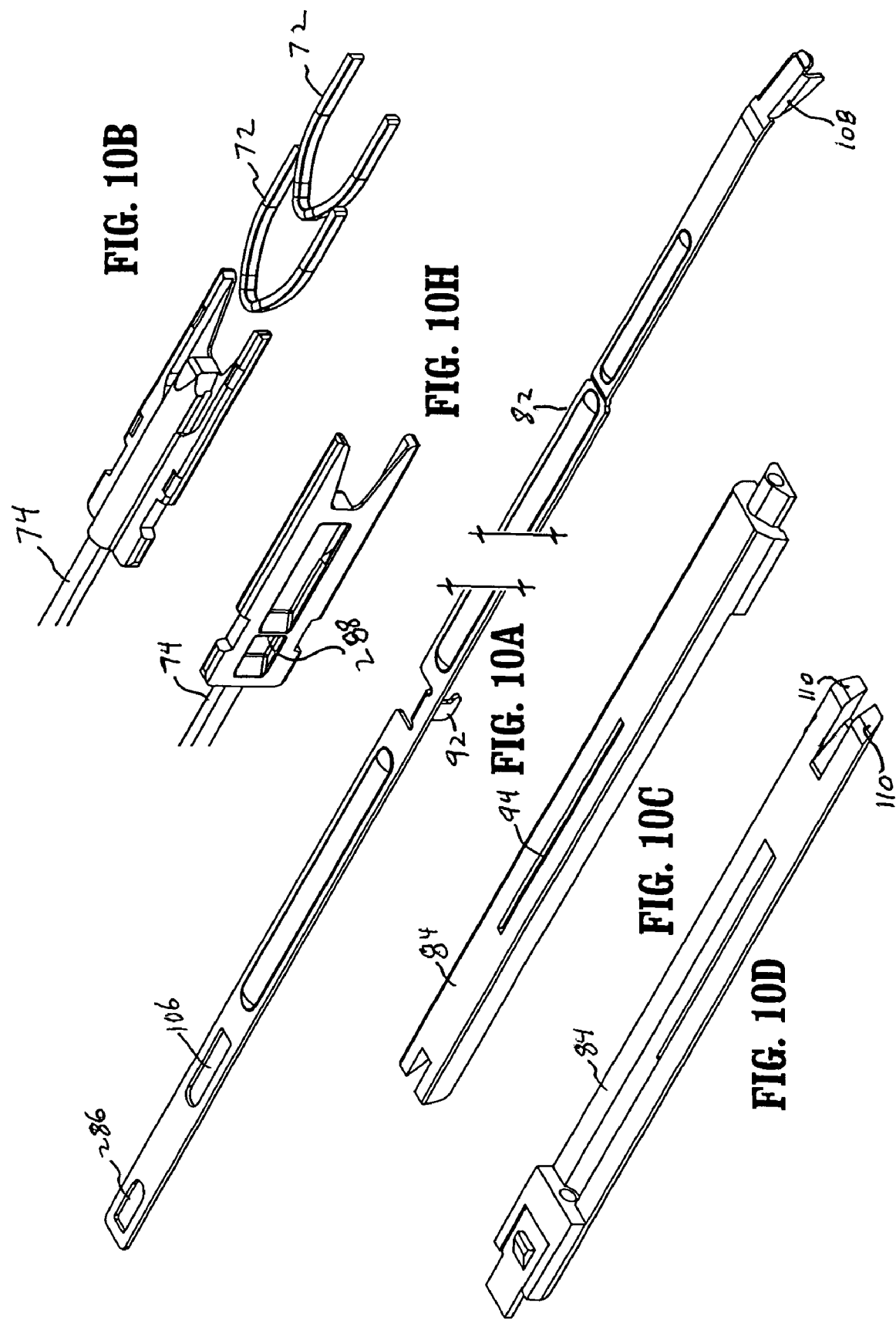

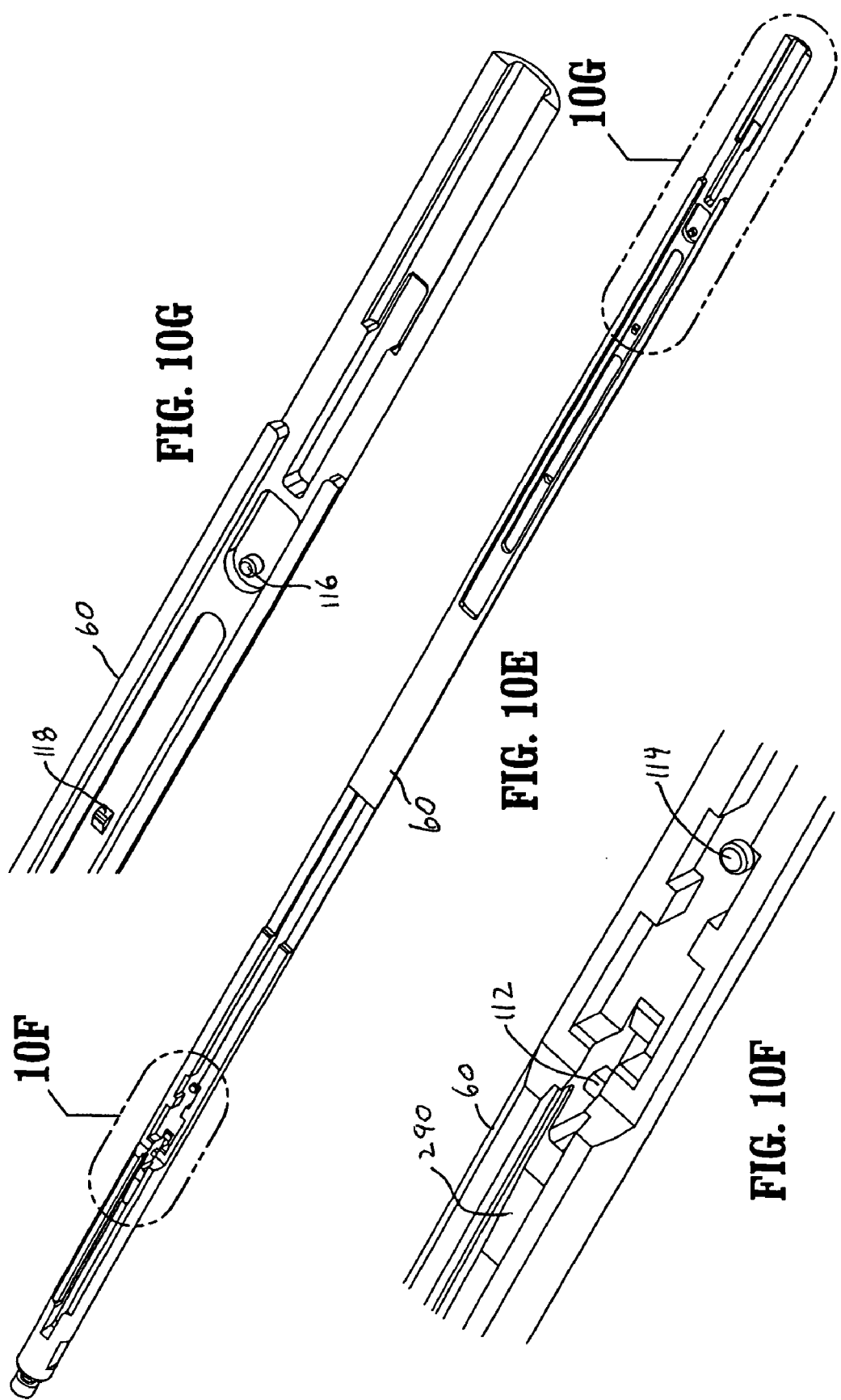

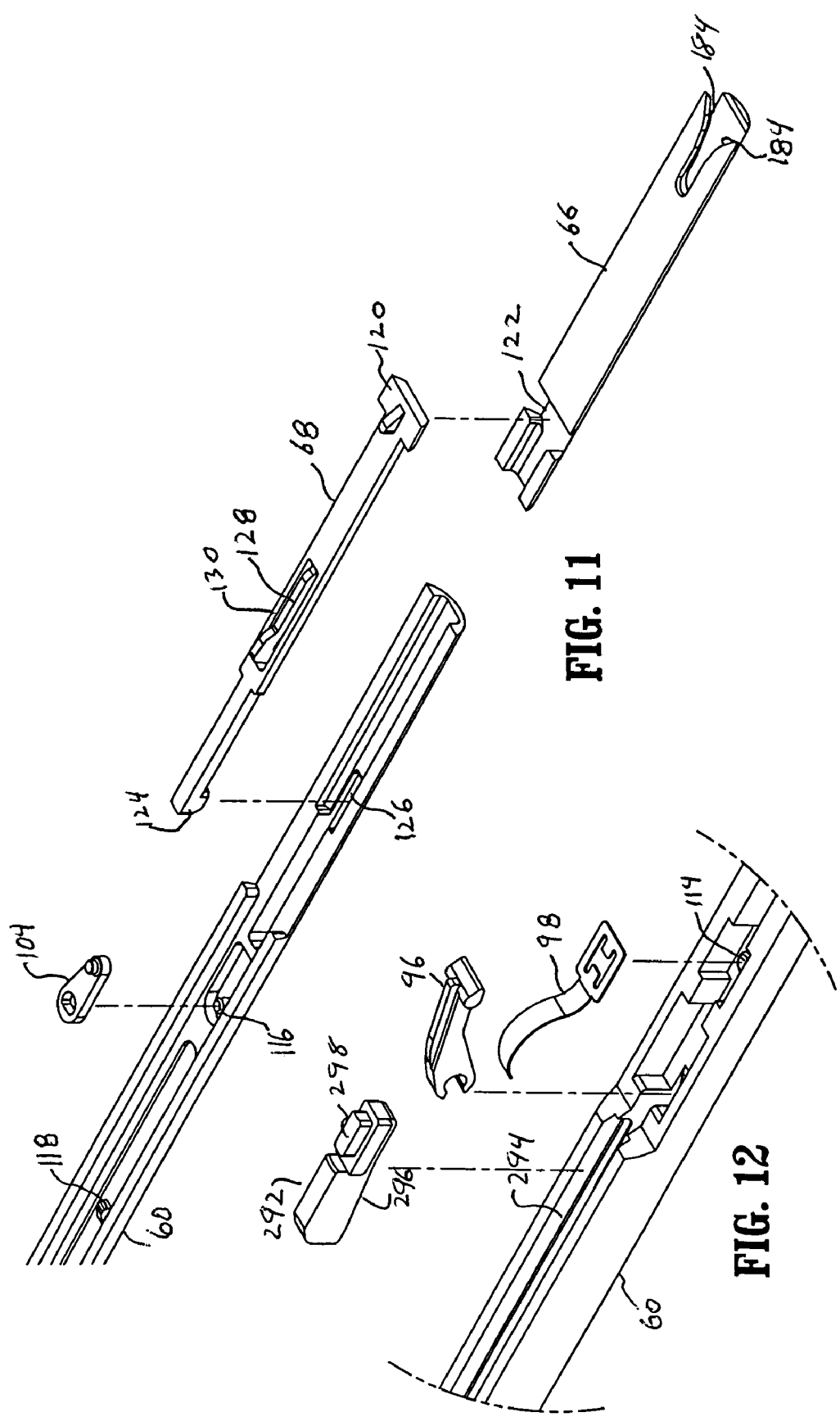

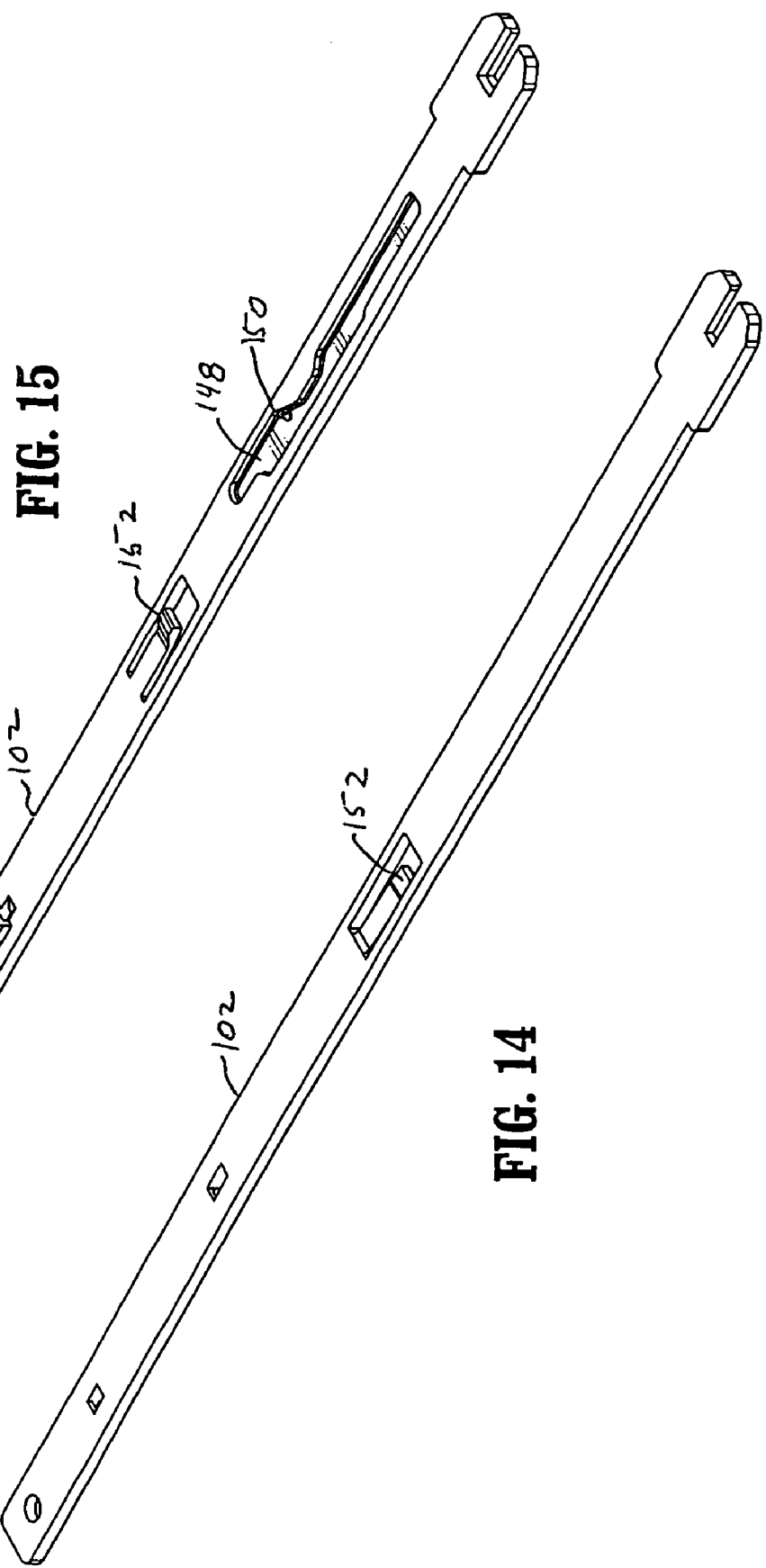

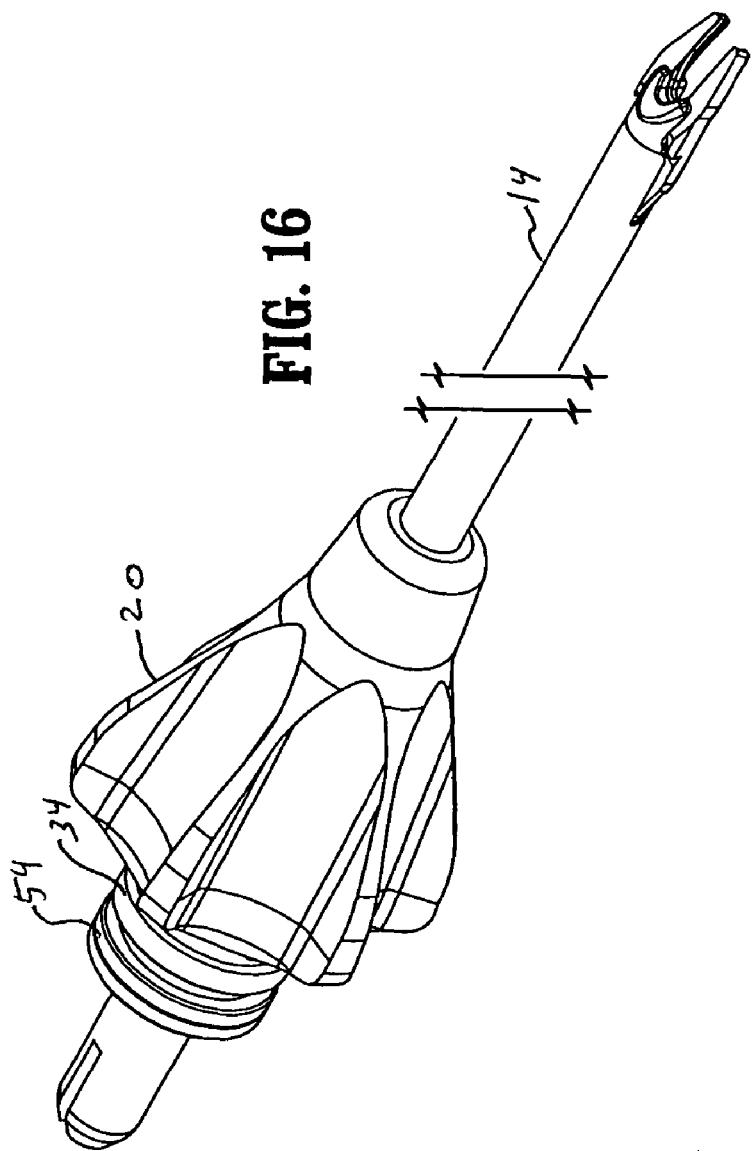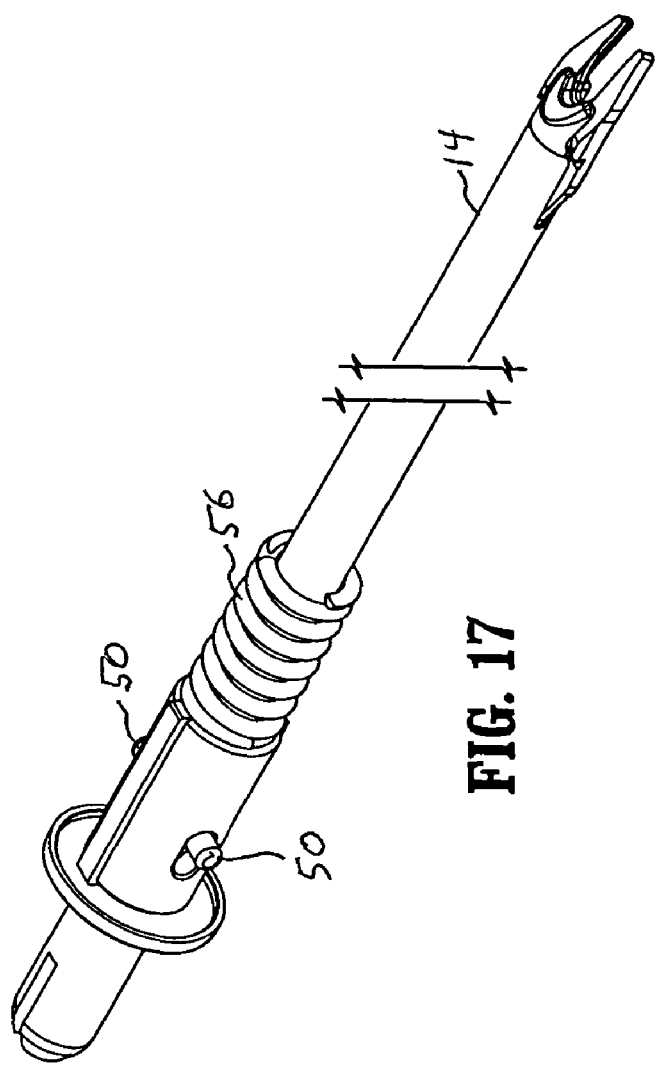

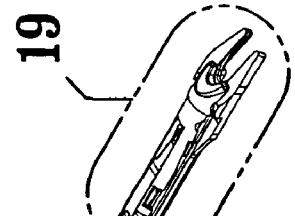
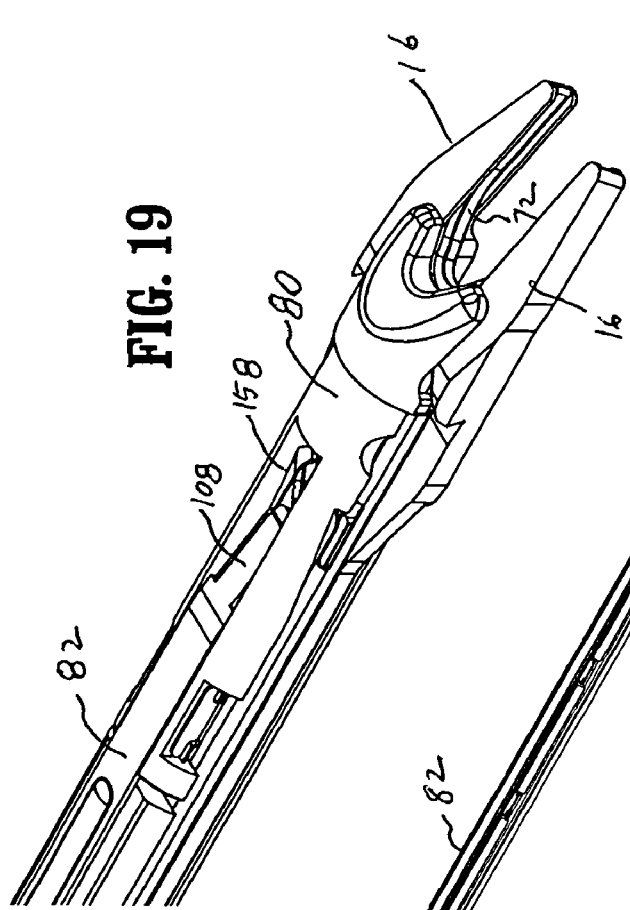
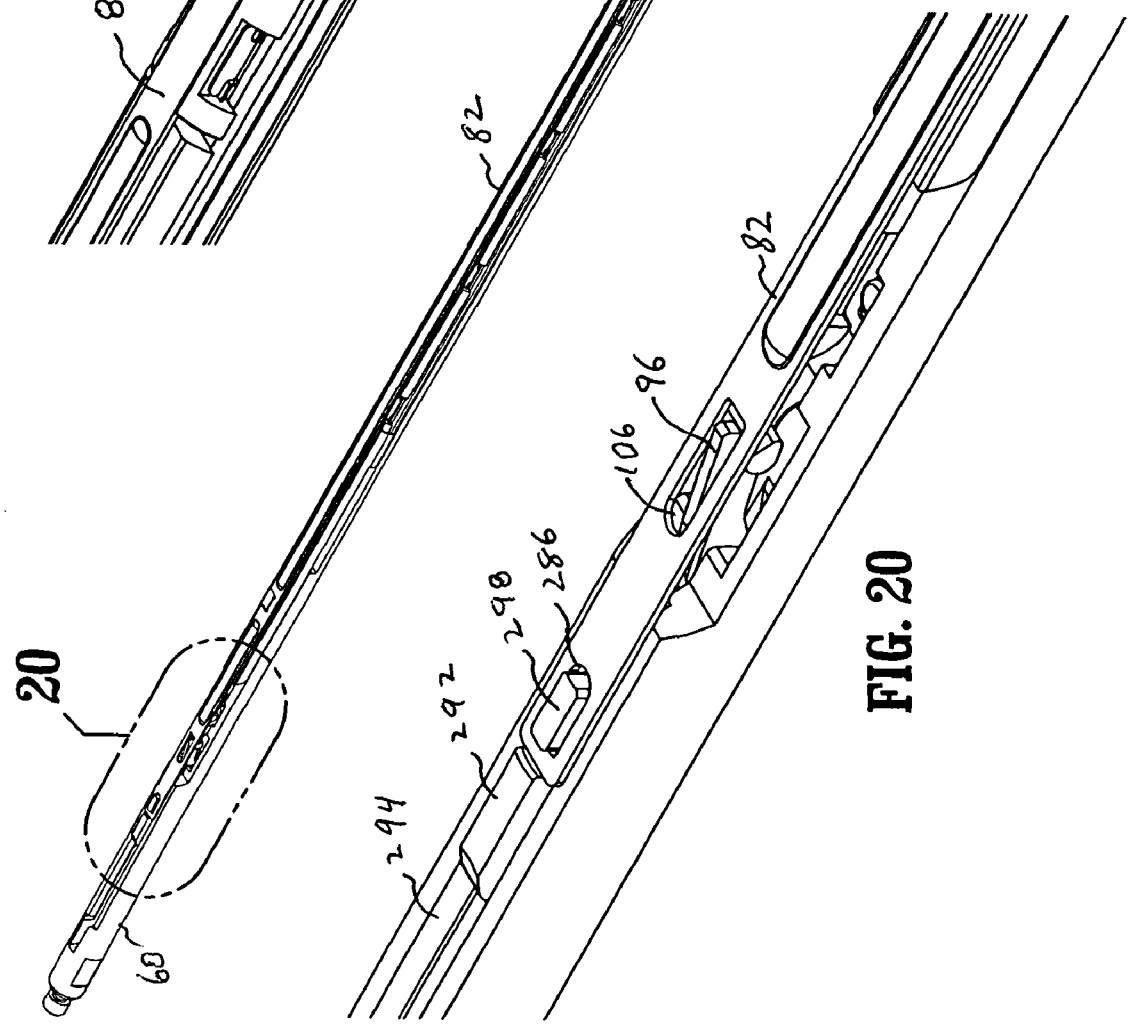

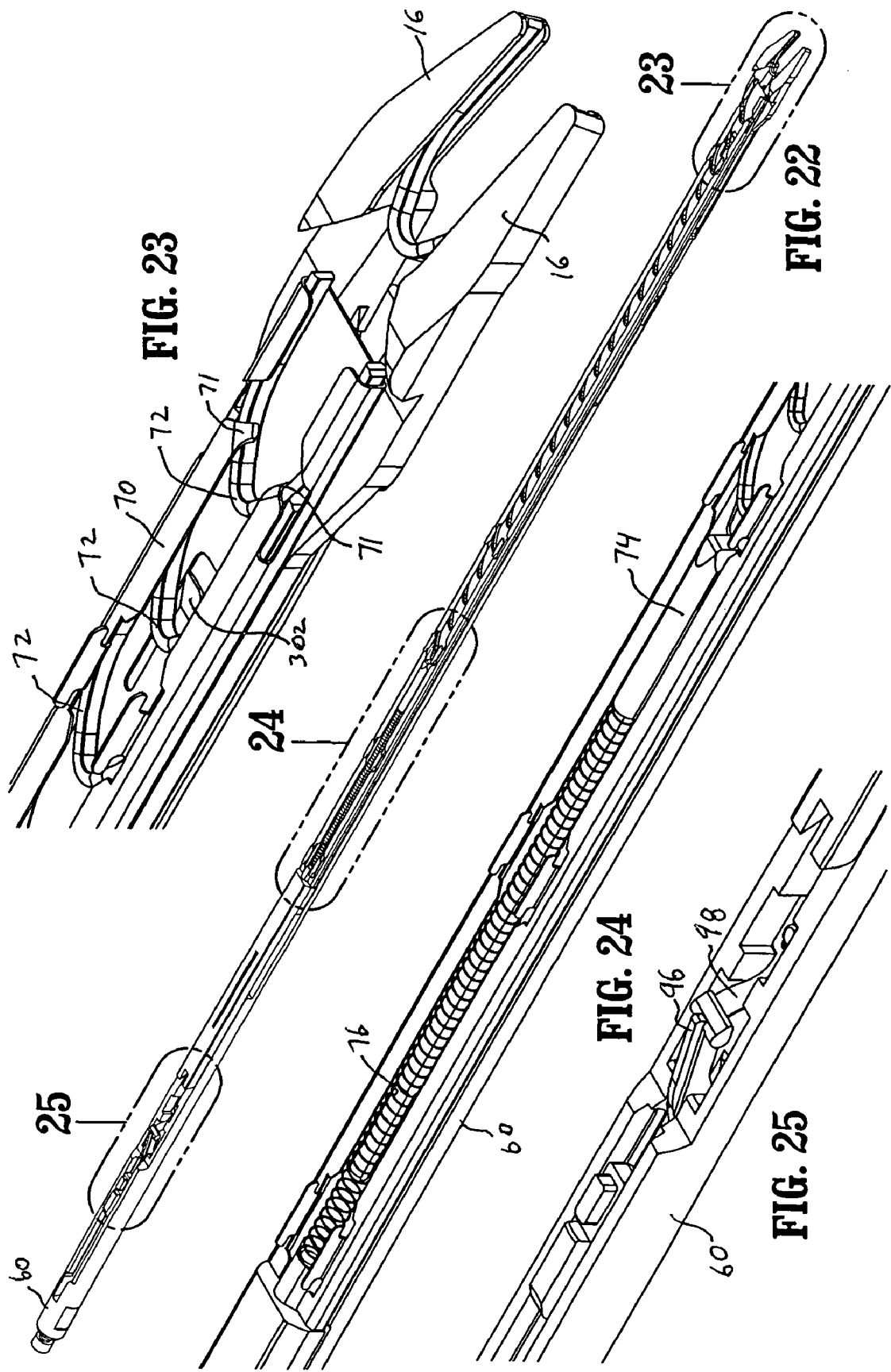

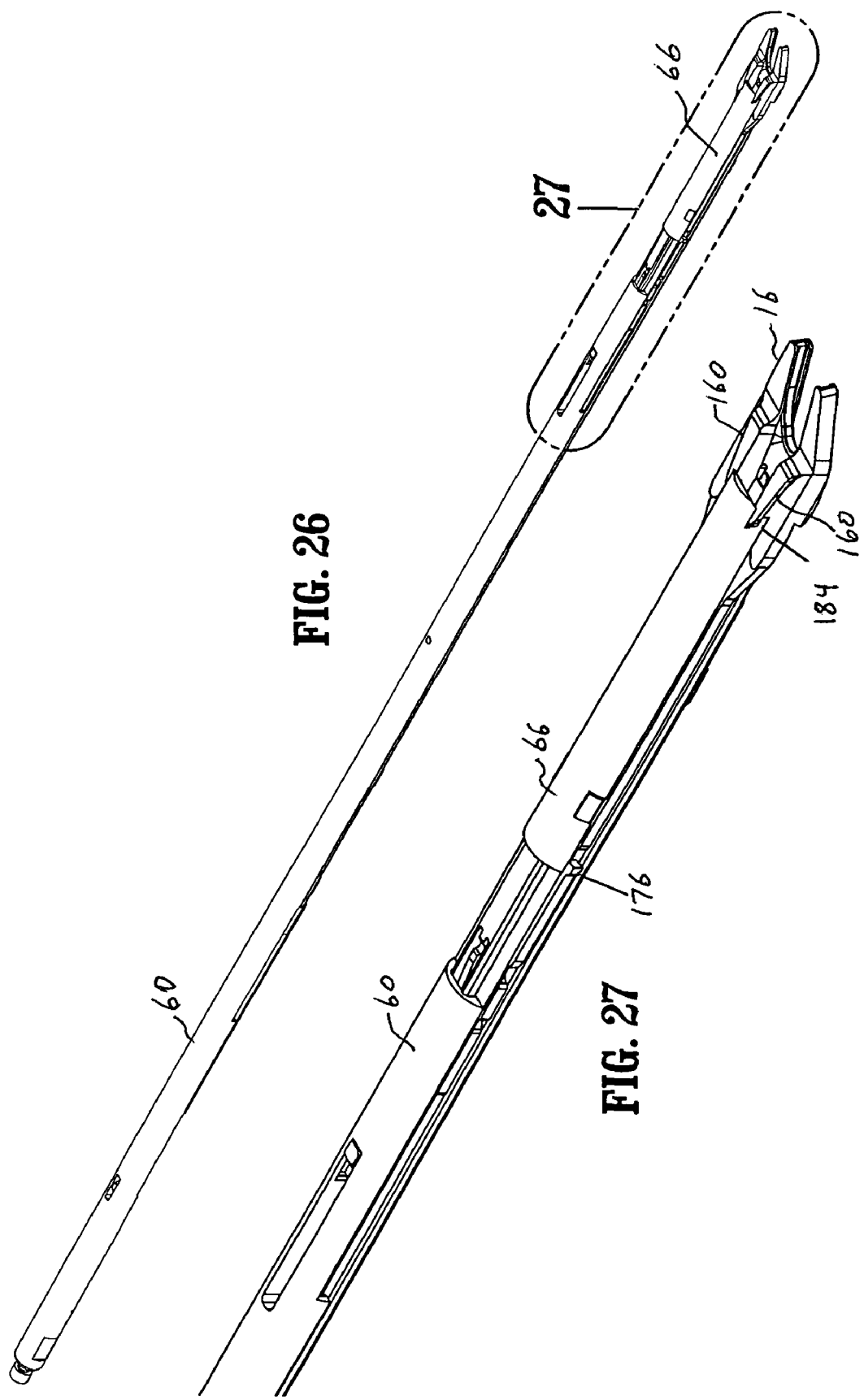

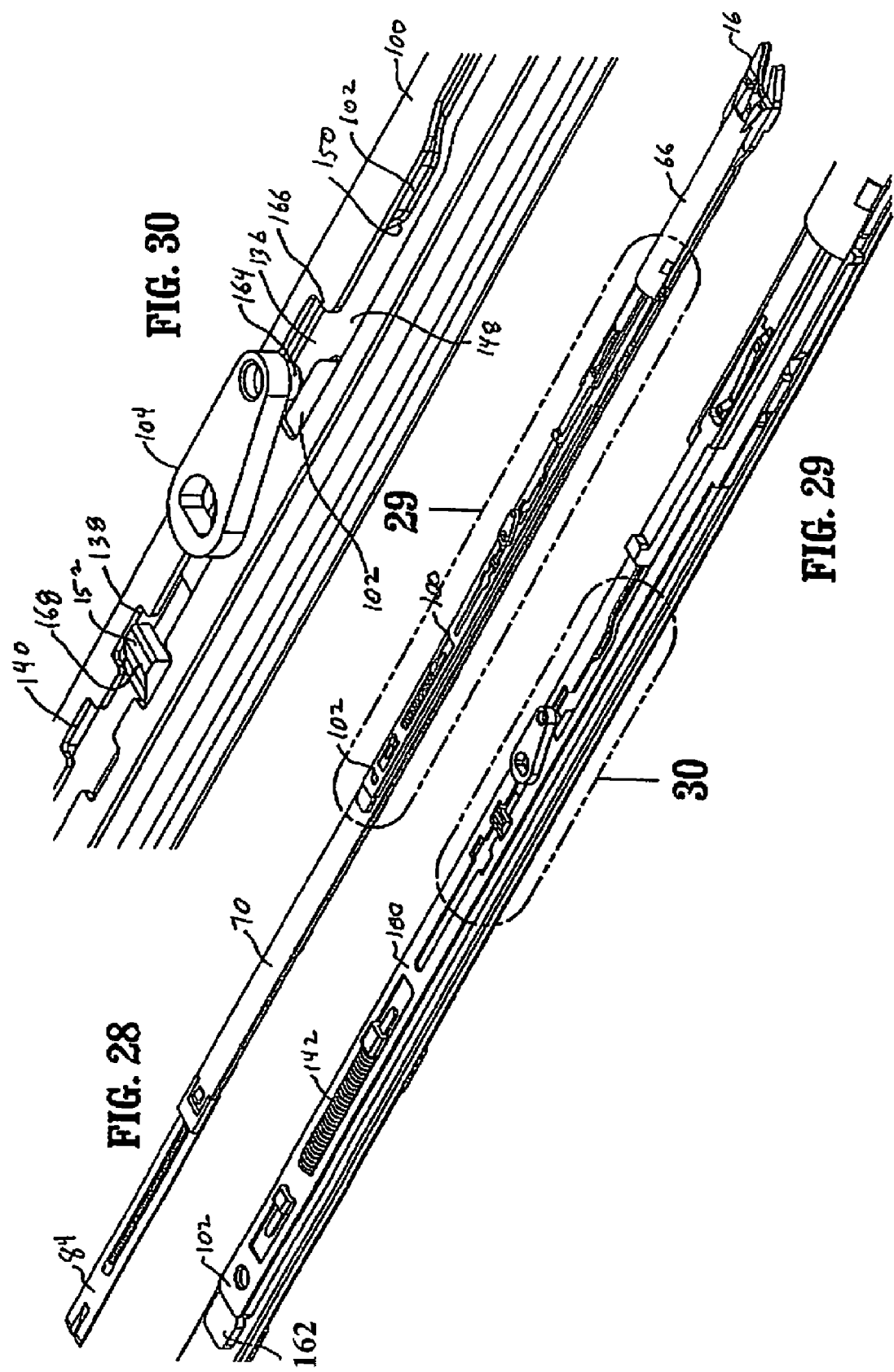

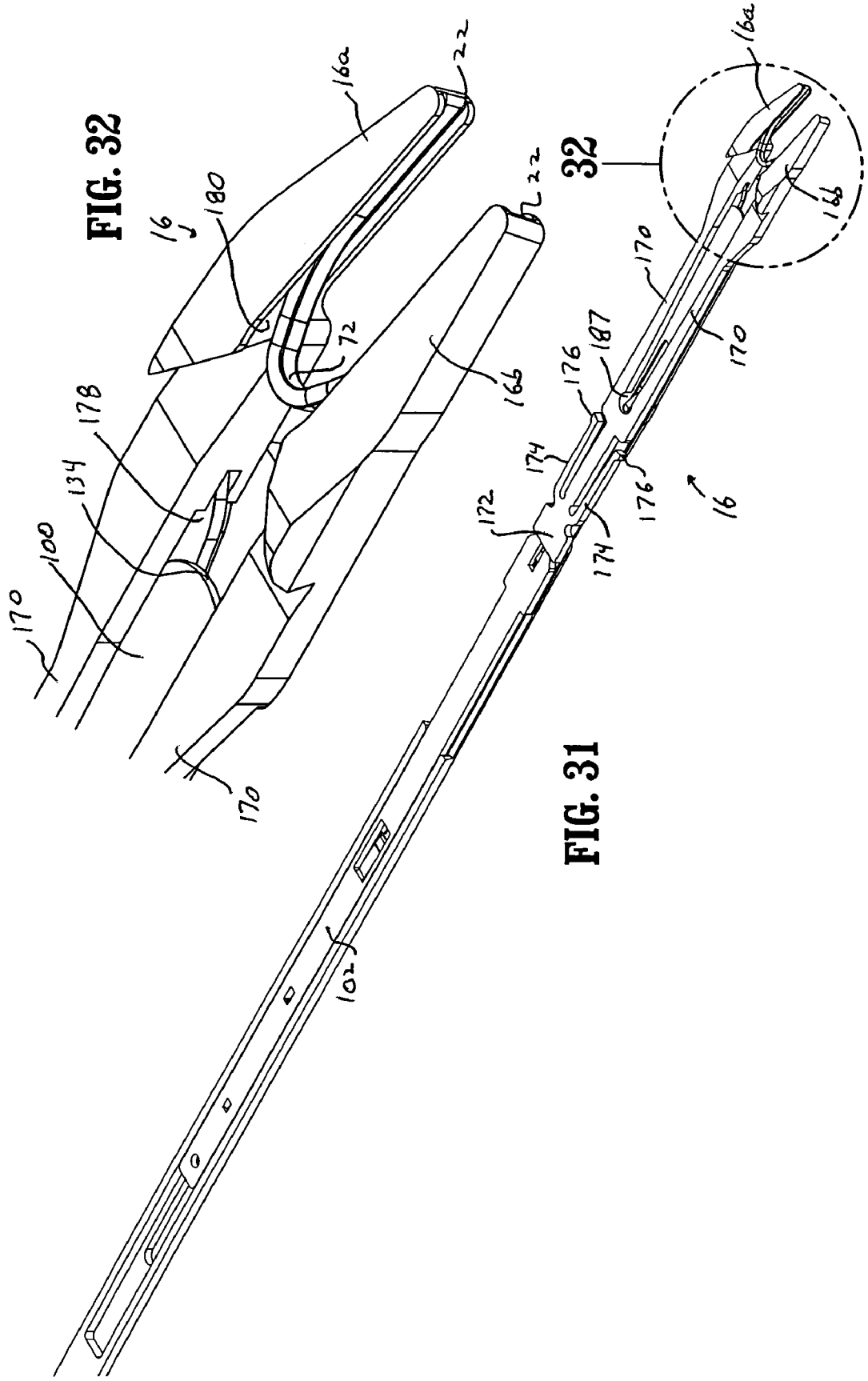

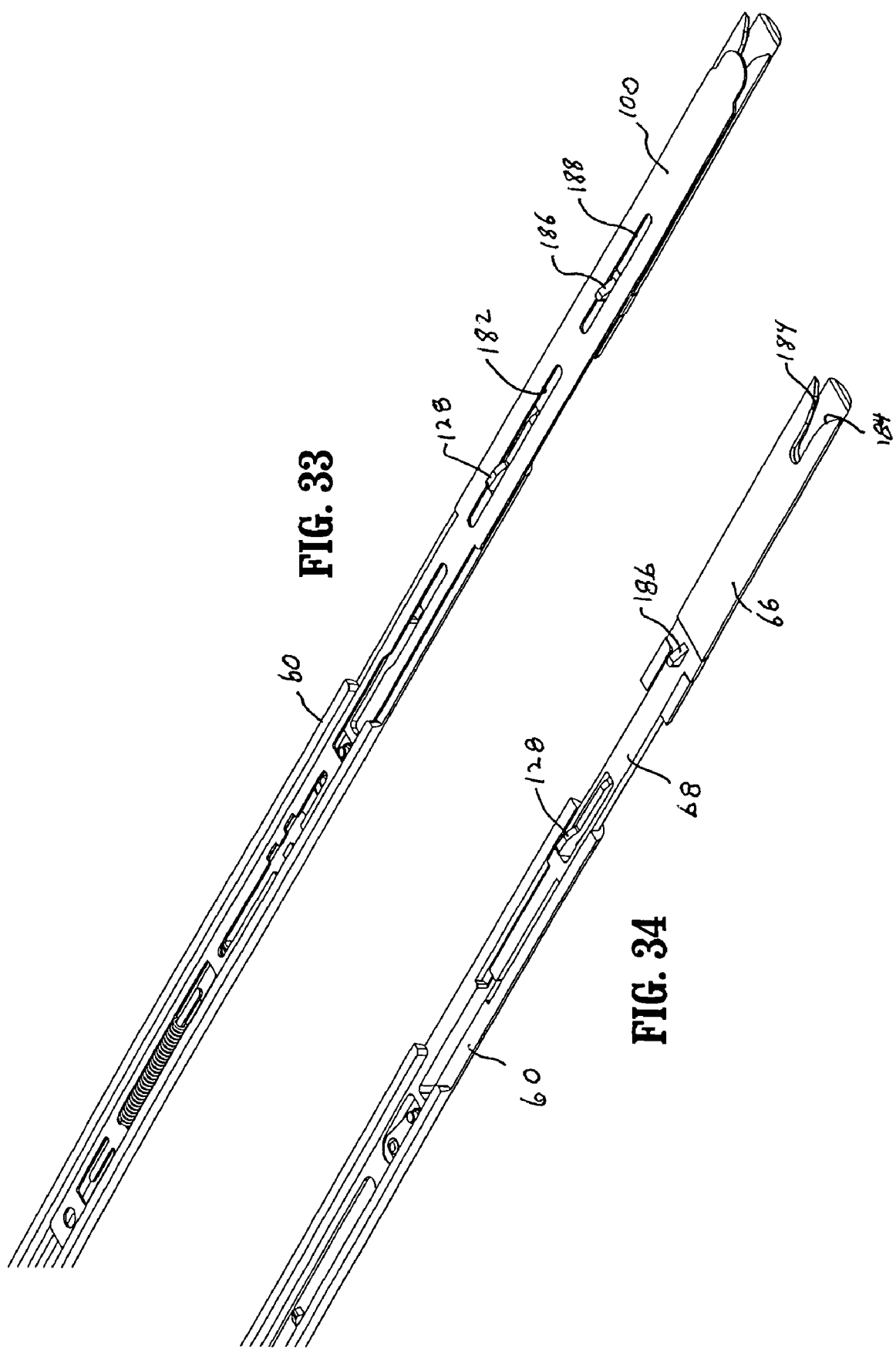

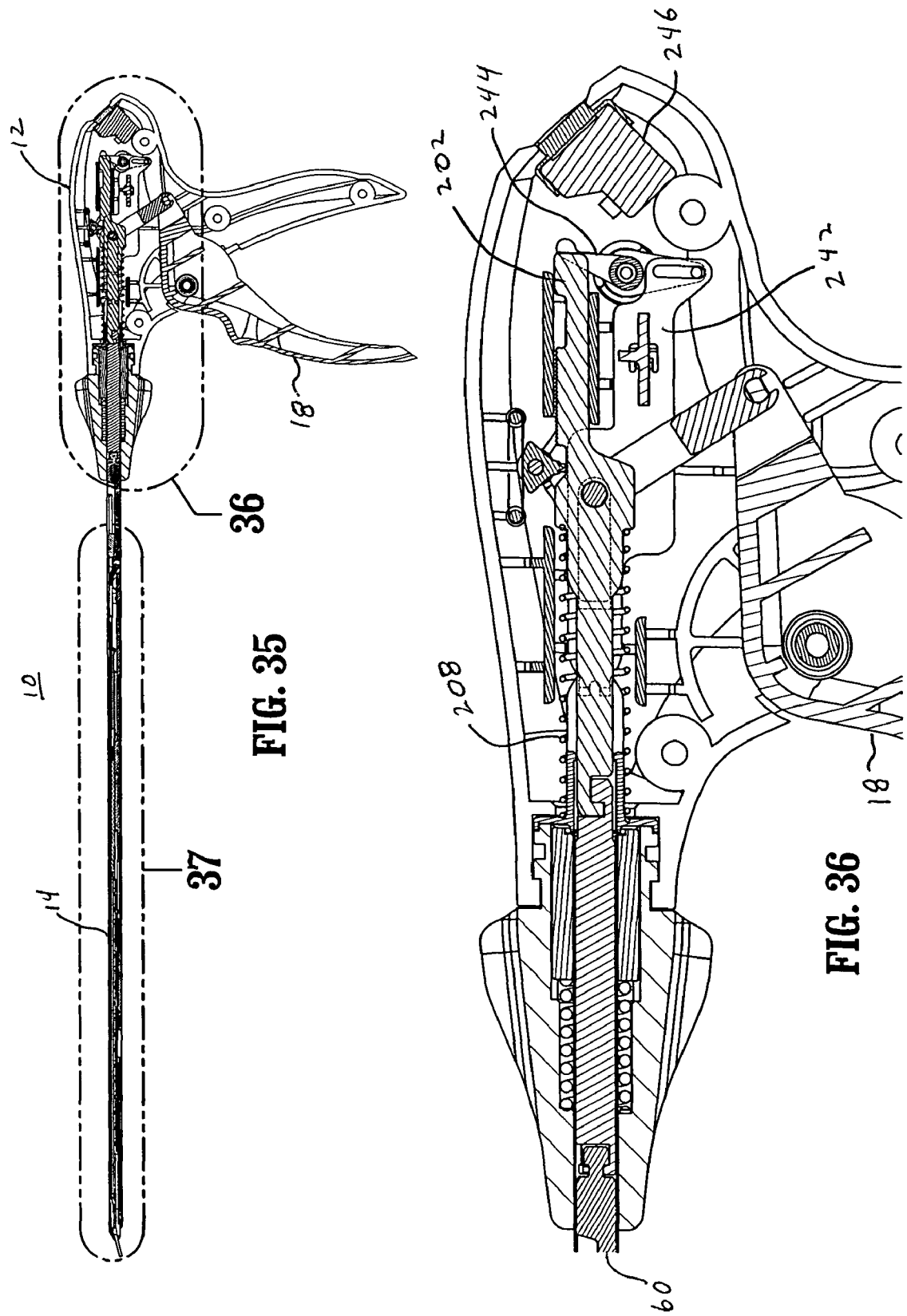

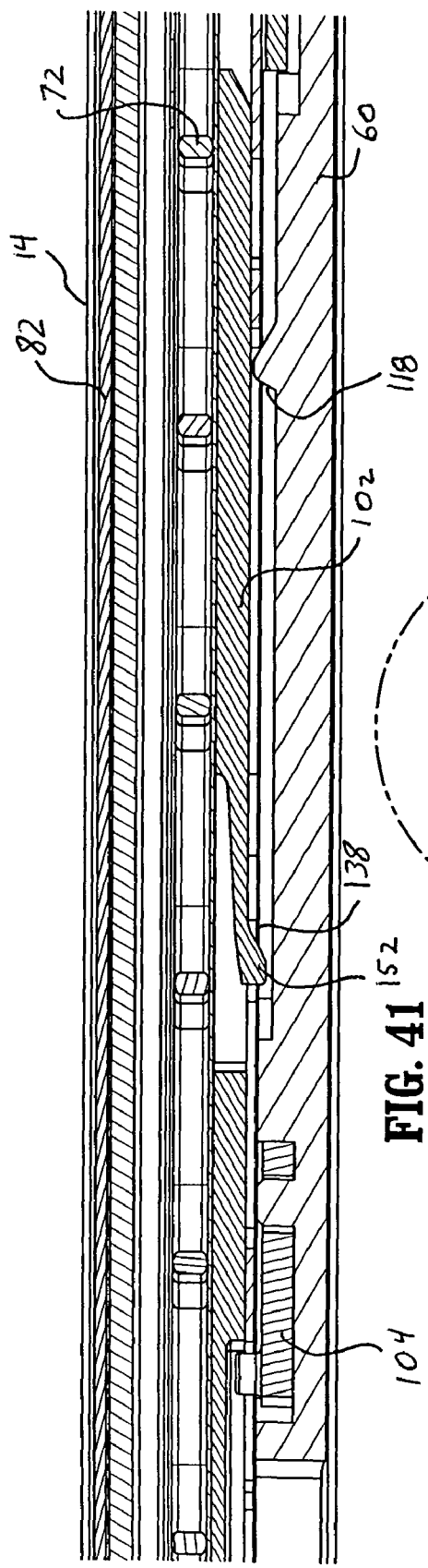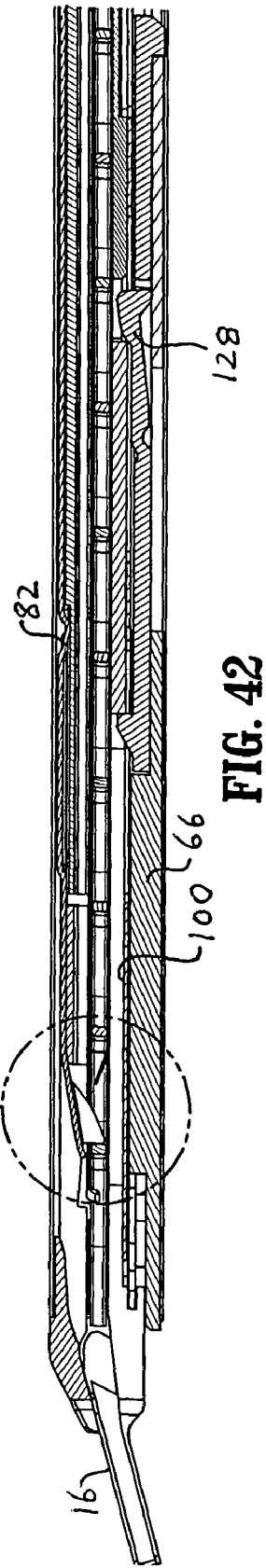

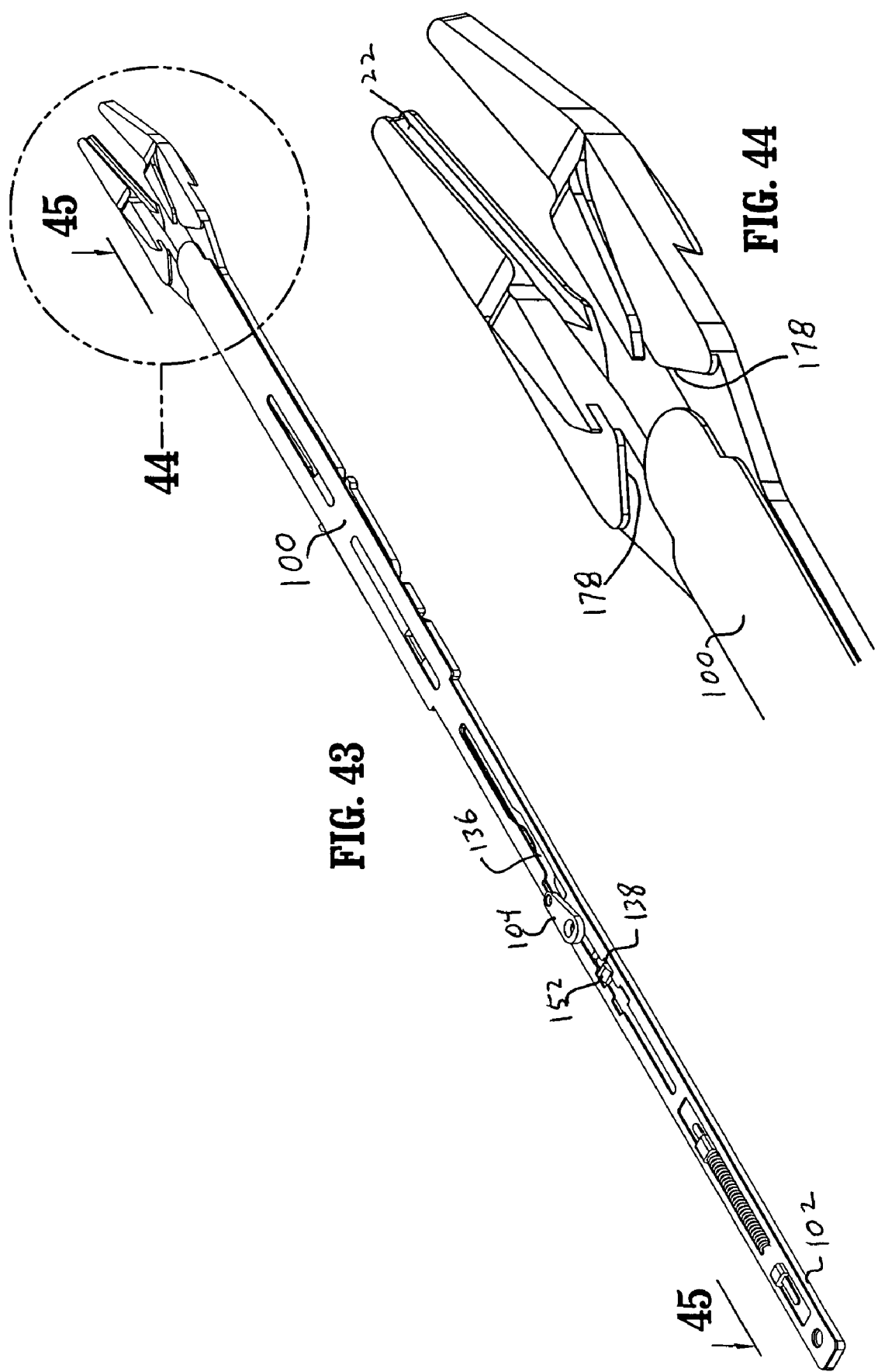

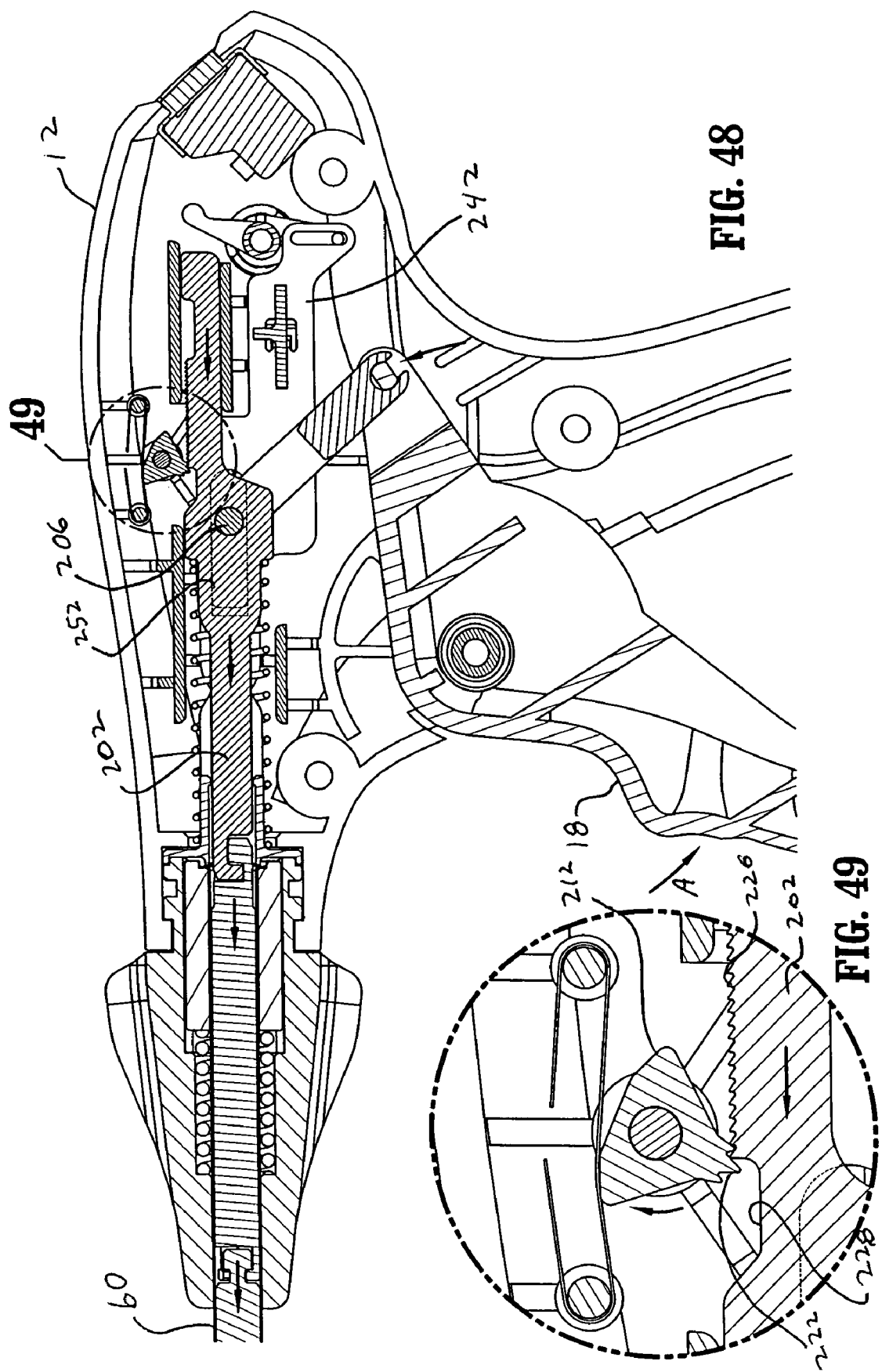

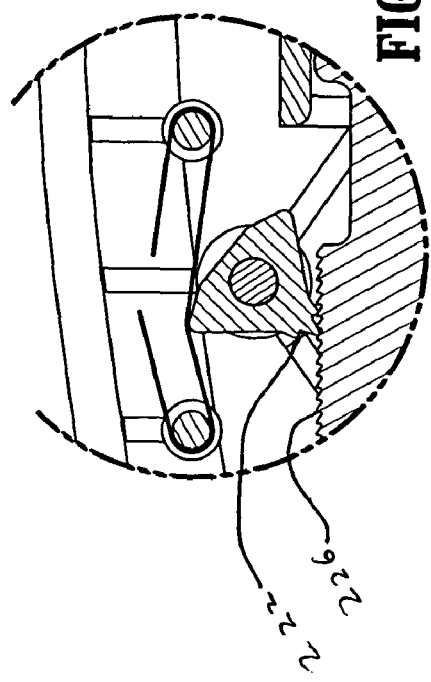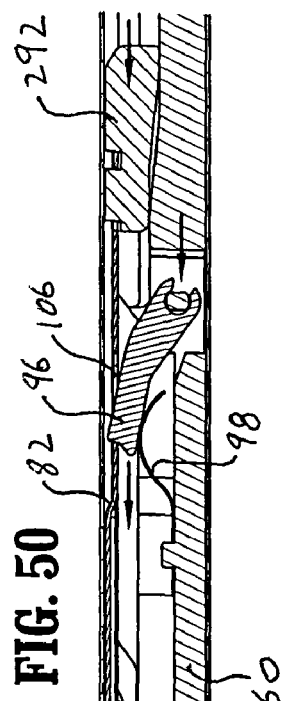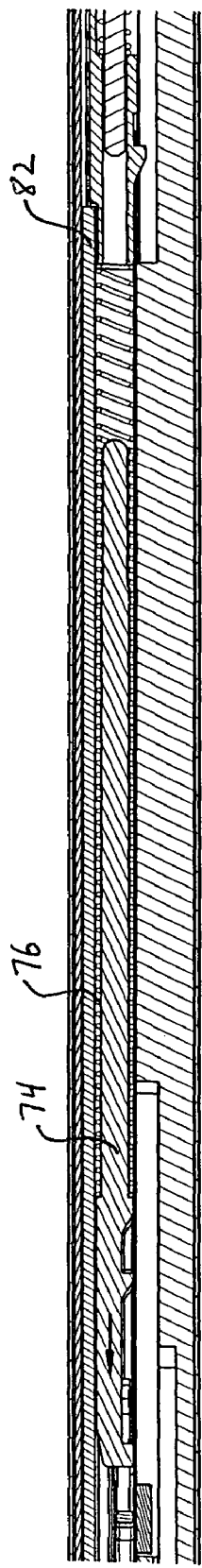

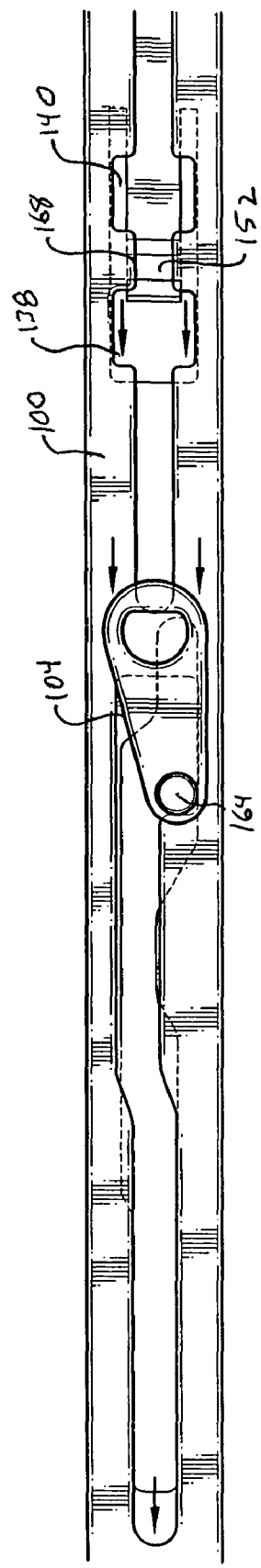
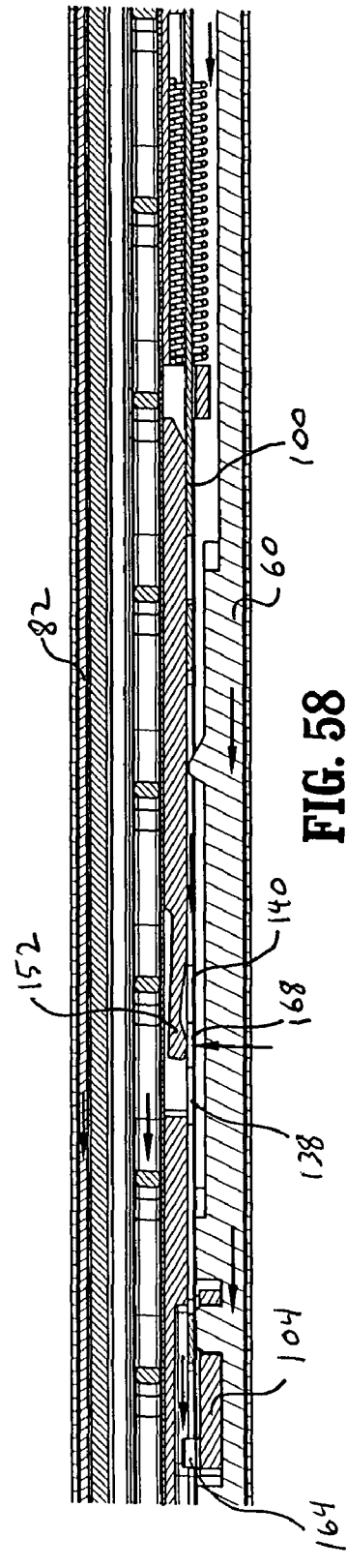
FIG. 57
FIG. 58

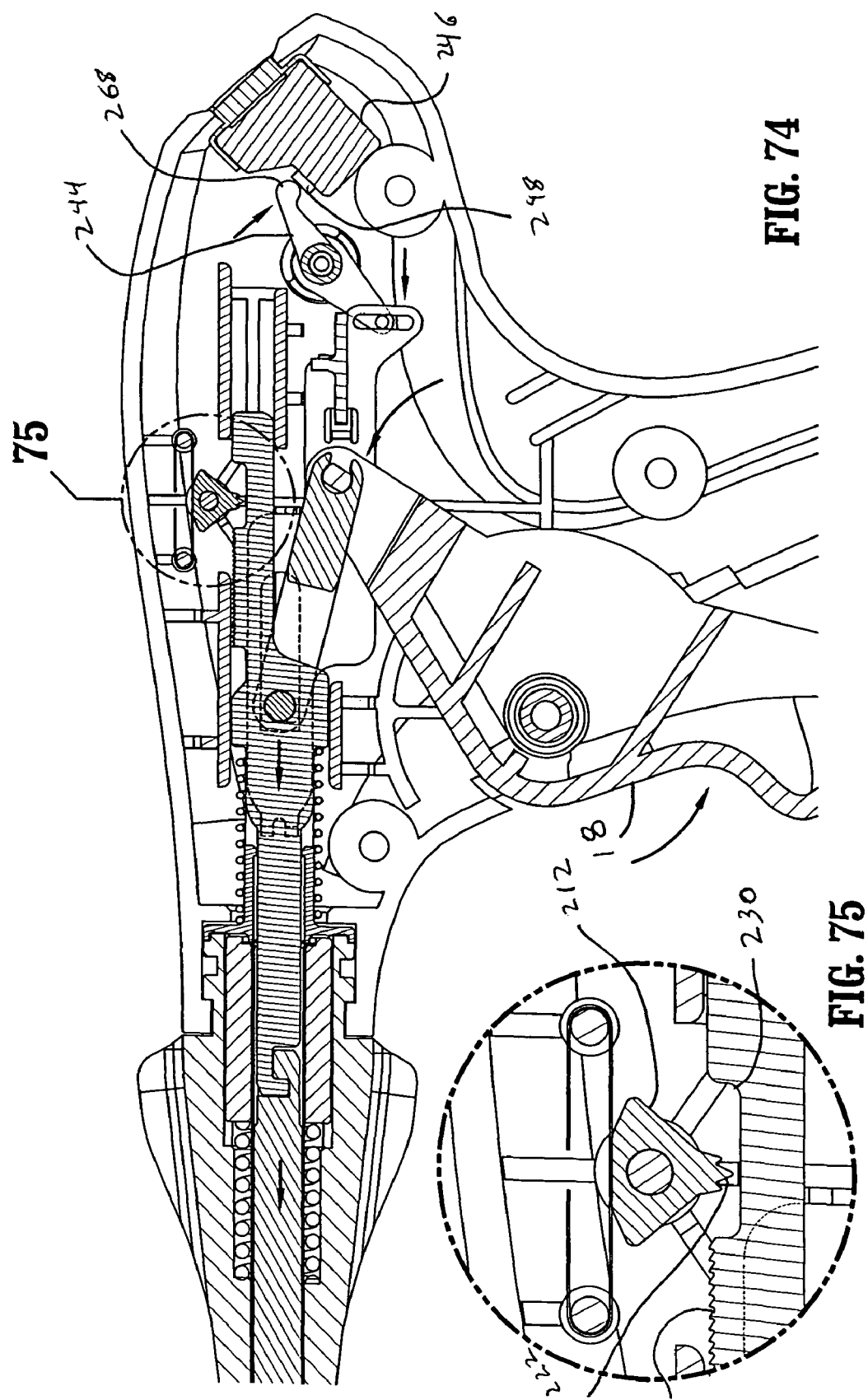

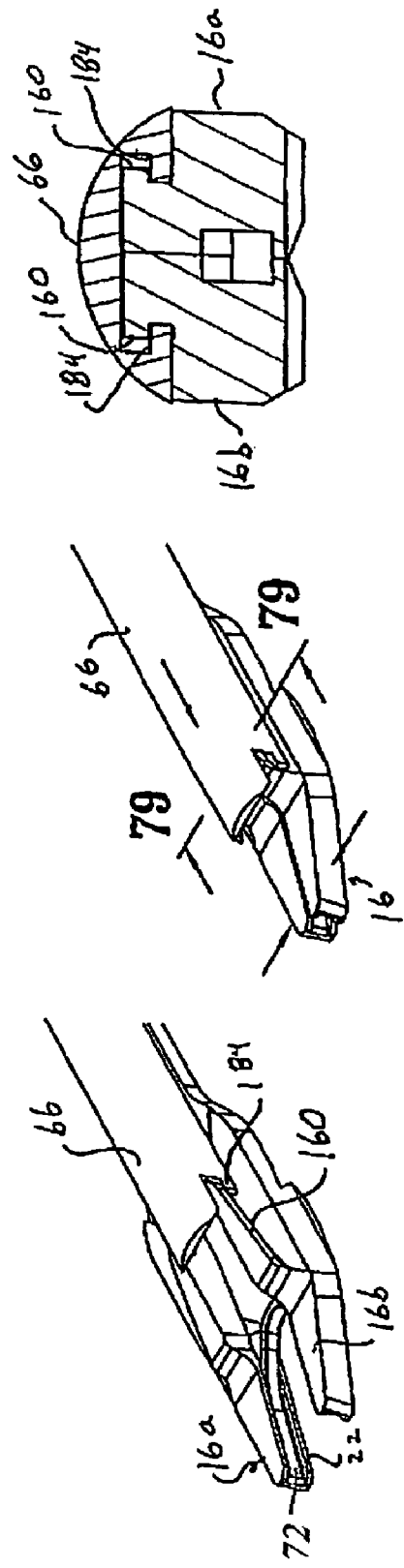

ENDOSCOPIC SURGICAL CLIP APPLIER

CROSS REFERENCE TO RELATED PATENT APPLICATIONS

The instant patent application claims priority to U.S. Provisional Patent Application Ser. No. 60/617,104 filed on Oct. 8, 2004 and U.S. Provisional Patent Application Ser. No. 60/617,016 filed on Oct. 8, 2004 which are both herein incorporated by reference in its entirety.

TECHNICAL FIELD

The technical field relates to surgical clip appliers. More particularly, the present disclosure relates to an endoscopic surgical clip applier having a mechanism for stabilizing the jaw structure during the insertion of a surgical clip.

DESCRIPTION OF THE RELATED ART

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying a single clip during an entry to the body cavity. Such single clip appliers are typically fabricated from a biocompatible material and are usually compressed over a vessel. Once applied to the vessel, the compressed clip terminates the flow of fluid therethrough.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 by Pratt et al., the contents of which is also hereby incorporated by reference herein in its entirety. These devices are typically, though not necessarily, used during a single surgical procedure. U.S. patent application Ser. No. 08/515,341 now U.S. Pat. No. 5,695,502 to Pier et al., the disclosure of which is hereby incorporated by reference herein, discloses a resterilizable surgical clip applier. The clip applier advances and forms multiple clips during a single insertion into the body cavity. This resterilizable clip applier is configured to receive and cooperate with an interchangeable clip magazine so as to advance and form multiple clips during a single entry into a body cavity. One significant design goal is that the surgical clip be loaded between the jaws without any compression of the clip from the loading procedure. Such bending or torque of the clip during loading often has a number of unintended consequences. Such compression during loading may alter slightly the alignment of the clip between the jaws. This will cause the surgeon to remove the clip from between the jaws for discarding the clip. Additionally such preloading compression may slight compress parts of the clip and change a geometry of the clip. This will cause the surgeon to remove the compressed clip from between the jaws for discarding the clip.

Endoscopic or laparoscopic procedures are often performed remotely from the incision. Consequently, application of clips may be complicated by a reduced field of view or reduced tactile feedback for the user at the proximal end of the device. It is therefore desirable to improve the operation of the instrument by providing indication to the user of a firing of an individual clip, the depletion of the clips contained in the loading unit, or any other surgical event. It is also desirable to provide a surgical clip applier that promotes a successful loading of the clip and that wedges the jaws of the surgical clip applier open, then loads the clip between the jaws in order to prevent any damage or excessive compression of the clip and prevents compression of the jaws on the clip before firing.

SUMMARY

According to a first aspect of the present disclosure, there is provided an apparatus for application of surgical clips to body tissue has a handle portion and a body extending distally from the handle portion and defining a longitudinal axis. The apparatus also has a plurality of surgical clips disposed within the body, and a jaw assembly mounted adjacent a distal end portion of the body. The jaw assembly includes first and second jaw portions movable between a spaced-apart and an approximated position. The apparatus also has a wedge plate longitudinally movable between the first and the second jaw portions, and a clip pusher configured to individually distally advance a surgical clip to the jaw assembly while the jaw portions are in the spaced apart position. The apparatus still further has an actuator at least partially disposed within the body and longitudinally movable in response to actuation of the handle portion and a jaw closure member positioned adjacent the first and second jaw portions to move the jaw portions to the approximated position.

According to another aspect of the present disclosure, the apparatus has a wedge plate that biases the first and the second jaw portions when the wedge plate is longitudinally moved between the first and the second jaw portions. The wedge plate maintains the first and the second jaw portions in a fixed predetermined relationship during loading of the clip. The fixed predetermined relationship prevents flexing of the first and the second jaw members during clip loading.

According to another aspect of the present disclosure, the apparatus has the wedge plate with a rounded distal tip.

According to another aspect of the present disclosure, the apparatus has the wedge plate with a first proximal window. The first proximal window is adapted to be engaged by a member disposed in the body and configured to hold the wedge plate in a distal most position. The distal most position is between the first and the second jaw members.

According to another aspect of the present disclosure, the apparatus has the wedge plate with a second proximal window. The second proximal window is adapted to be engaged by the member and the second proximal window is configured to hold the wedge plate in a proximal most position. The proximal most position is retracted from the first and the second jaw members. The proximal most position of the wedge plate is configured to allow the first and the second jaw members to compress the clip.

According to another aspect of the present disclosure, the member is movable from the second proximal window to first proximal window by the actuator. The actuator moves the wedge plate distally. The member moves from the second proximal window to the first proximal window upon the wedge plate moving distally.

According to another aspect of the present disclosure, the actuator further comprises a cam link. The cam link is engageable with a cam slot in the wedge plate. The cam link moves the wedge plate distally.

According to another aspect of the present disclosure, the member is a flexible leg.

According to another aspect of the present disclosure, the apparatus has a cam slot with a driving edge. The cam link engages the driving edge. The cam link is configured to longitudinally move the wedge plate distally.

According to another aspect of the present disclosure, when the actuator is driven distally the cam link is driven distally. The cam link engages the driving edge of the cam slot. The cam link longitudinally moves the wedge plate to move the rounded distal end between the first and the second jaw members. The member engages the first proximal window to hold the wedge plate between the first and second jaws for loading.

According to another aspect of the present disclosure, when the cam link is driven further distally the cam link disengages the driving edge and traverses in the cam slot. The cam link permits the wedge plate to move the rounded distal end proximally from between the first and the second jaw members. The member engages the second proximal window to hold the wedge plate in the proximal most position.

According to another aspect of the present disclosure, there is provided an apparatus for the application of surgical clips to body tissue. The apparatus has a handle portion, a body extending distally from the handle portion and defining a longitudinal axis, and a plurality of surgical clips disposed within the body. The apparatus also has a jaw assembly mounted adjacent a distal end portion of the body, and a clip pusher configured to individually distally advance a surgical clip to the jaw assembly. The apparatus further includes an actuator at least partially disposed within the body and longitudinally movable in response to actuation of the handle portion with a counter mechanism. The counter mechanism is associated with the handle portion and the counter mechanism indexes in response to actuation of the handle portion.

According to another aspect of the present disclosure, the counter mechanism comprises a liquid crystal display.

According to yet another aspect of the present disclosure, the counter mechanism comprises a backlight.

According to another aspect of the present disclosure, the counter mechanism is indexed upon full actuation of the handle portion.

According to another aspect of the present disclosure, the apparatus has a counter mechanism that is triggered by the actuator.

According to another aspect of the present disclosure, the counter mechanism is in the handle and connected to the actuator. The counter mechanism has a member connected to the actuator. The counter mechanism has a liquid crystal display having a display contact. The display contact is activated when the member contacts the display contact.

According to another aspect of the present disclosure, the member is rotatable. The member rotates in response to longitudinal movement of the actuator to contact the display contact.

According to another aspect of the present disclosure, the counter mechanism is a liquid crystal display having a lens. The liquid crystal display displays an image. The lens magnifies the image.

According to another aspect of the present disclosure, the actuator includes an opening. The counter mechanism with the member has a first arm and a second arm. The first arm is connected to the opening. When said actuator longitudinally moves in a distal direction the actuator deflects the first arm and the member rotates in response to the movement. The second arm contacts the display contact in response to the rotation of the member. The display contact is activated when the second arm contacts the display contact.

According to another aspect of the present disclosure, there is provided an apparatus for the application of surgical clips to body tissue. The apparatus has a handle portion, a body extending distally from the handle portion and defining a longitudinal axis, a plurality of surgical clips disposed within the body and a jaw assembly mounted adjacent a distal end portion of the body. The jaw assembly includes first and second jaw portions movable between a spaced-apart and an approximated position. The apparatus also has a clip pusher configured to individually distally advance a surgical clip to the jaw assembly while the jaw portions are in the spaced apart position and an actuator at least partially disposed within the body and longitudinally movable in response to actuation of the handle portion. The apparatus also has a jaw closure member positioned adjacent the first and second jaw portions to move the jaw portions to the approximated position and a lockout mechanism configured to engage with the clip pusher to prevent the application of the surgical clips to tissue when the plurality of clips are substantially exhausted.

According to another aspect of the present disclosure, the lockout mechanism has a member. The member is longitudinally movable with the actuator to a distal most position. The member reaches said distal most position and the member engages the clip pusher. The member prevents the clip pusher to distally advance the surgical clip to the jaw assembly.

According to another aspect of the present disclosure, the apparatus further comprises a clip follower. The clip follower distally biases the clips disposed in the body. The lockout mechanism includes a member. The member is longitudinally movable with the actuator to a distal most position. The member reaches the distal most position and the member engages the follower. The member prevents the follower from retracting proximally. Upon retraction of the clip pusher, the clip pusher engages the follower. The member prevents the clip pusher to distally advance the surgical clip to the jaw assembly.

According to another aspect of the present disclosure, the member is a lockout wedge.

According to another aspect of the present disclosure, the member has at least one member angled surface. The actuator has at least one actuator angled surface. As the actuator retracts proximally the at least one actuator angled surface engages the member angled surface. The engagement prevents the actuator from retracting proximal to a proximal most position.

According to another aspect of the present disclosure, there is provided an apparatus for the application of surgical clips to body tissue. The apparatus has a handle portion, and a body extending distally from the handle portion and defining a longitudinal axis. The apparatus also has a plurality of surgical clips disposed within the body, and a jaw assembly mounted adjacent a distal end portion of the body. The jaw assembly includes first and second jaw portions movable between a spaced-apart and an approximated position. The apparatus also has a clip pusher configured to individually distally advance a surgical clip to the jaw assembly while the jaw portions are in the spaced apart position. The apparatus further has an actuator at least partially disposed within the body and longitudinally movable in response to actuation of the handle portion. The apparatus also has a jaw closure member positioned adjacent the first and second jaw portions to move the jaw portions to the approximated position, and a rack having a plurality of ratchet teeth being connected to the actuator. The apparatus also has a pawl with at least one tooth configured to engage the ratchet teeth. The pawl is biased in the handle portion. As the actuator is moved longitudinally, the ratchet teeth are passed over the pawl. The pawl is configured to prevent an inadvertent return of the actuator before full actuation of the apparatus. The apparatus also has a wedge plate longitudinally movable between the first and the second jaw portions.

According to another aspect of the present disclosure, the pawl is biased by a pawl spring. The pawl spring biases the pawl into engagement with the rack.

According to another aspect of the present disclosure, the apparatus further comprises a first and a second post connected to an interior side of the handle portion. The first and the second posts are configured to support the pawl spring.

According to another aspect of the present disclosure, there is provided an apparatus for the application of surgical clips to body tissue. The apparatus also has a handle portion, a body extending distally from the handle portion and defining a longitudinal axis, a plurality of surgical clips disposed within the body, and a jaw assembly mounted adjacent a distal end portion of the body. The jaw assembly includes first and second jaw portions movable between a spaced-apart and an approximated position. The apparatus also has a clip pusher configured to individually distally advance a surgical clip to the jaw assembly while the jaw portions are in the spaced apart position, and an actuator at least partially disposed within the body and longitudinally movable in response to actuation of the handle portion. The apparatus further has a jaw closure member positioned adjacent the first and second jaw portions to move the jaw portions to the approximated position. The body portion has an outer diameter. The jaw assembly has a width in the spaced apart position. The width is less than or equal to said outer diameter of the body.

According to another aspect of the present disclosure, the apparatus has the body with a length. The length is suitable to facilitate use in bariatric surgery. According to another aspect of the present disclosure, the apparatus with the length suitable to facilitate use in bariatric surgery has the length being greater than thirty centimeters.

BRIEF DESCRIPTION OF THE DRAWINGS

A particular embodiment of a surgical clip applier is disclosed herein with reference to the drawings wherein;

FIG. 2 is another perspective view of the surgical clip applier of FIG. 1;
FIG. 3 is an enlarged perspective view of the jaw structure of the surgical clip applier;
FIG. 4 is a top view of the surgical clip applier;
FIG. 5 is a side view of the surgical clip applier;
FIG. 7A is a perspective view of a drive link and spindle connection;
FIG. 7B is a cross sectional view of the knob, bushing and retention pins;
FIG. 7C is a perspective view of the knob;
FIG. 7D is a perspective view of the proximal end of the outer tube;
FIG. 7E is a perspective view of the proximal end of the outer tube assembled with the bushing;
FIG. 8 is a perspective view of a pawl;
FIG. 9 is a perspective view of a rack;
FIG. 9A is another perspective view of the rack;
FIGS. 9B and 9C are opposite perspective views of an actuator plate;
FIG. 10A is a perspective view of a feed bar;
FIG. 10B is a perspective view of a follower and surgical clips;
FIGS. 10C and 10D are opposite perspective views of a trip block;
FIG. 10E is a perspective view of a spindle;
FIG. 10F is an enlarged area of detail of FIG. 10E;
FIG. 10G is an enlarged area of detail of FIG. 10E;
FIG. 10H is a perspective view of a follower illustrating an abutment surface on the underside of the follower;
FIG. 11 is a perspective view of the distal end of the spindle and a driver;
FIG. 12 is a perspective view of a trip lever mechanism on the spindle and lock out wedge;
FIGS. 14 and 15 are opposite perspective views of a filler component;
FIG. 16 is a perspective view of the rotation knob and shaft assembly;
FIG. 17 is a perspective view of the overpressure assembly;
FIG. 18 is a perspective view of the spindle and jaw assembly;
FIG. 19 is an enlarged area of detail of the spindle and jaw assembly of FIG. 18;
FIG. 20 is an enlarged area of detail of the spindle and trip lever of FIG. 18;
FIG. 22 is a perspective view of the surgical clip applier shaft assembly with parts removed;
FIG. 23 is an enlarged area at detail of FIG. 22;
FIG. 24 is an enlarged area of detail of FIG. 22;
FIG. 25 is an enlarged area of detail of FIG. 22;
FIG. 26 is a perspective view of the spindle, driver and jaw assembly;
FIG. 27 is an enlarged area of detail of FIG. 26;
FIG. 28 is a perspective view of the cam link and wedge plate assembly;
FIG. 29 is an enlarged area of detail of FIG. 28;
FIG. 30 is an enlarged area of detail of FIG. 29;
FIG. 31 is a perspective view of the filler component and jaw assembly;
FIG. 32 is an enlarged perspective view of the jaw assembly of FIG. 31;

FIGS. 33 and 34 are perspective views of the distal end of the spindle including wedge plate and driver;

FIG. 35 is a side view, partially shown in section, of the surgical clip applier in a pre-fired condition;

FIG. 36 is in enlarged area of detail of FIG. 35;

FIG. 41 is enlarged area of detail of FIG. 40;

FIG. 42 is a side view, shown in section, of the distal end of the surgical clip applier of FIG. 37;

FIG. 42A is a side view, shown in section, of a feedback pusher and lance on a channel;

FIG. 43 is a perspective view of the wedge plate and jaw assembly;

FIG. 44 is an enlarged area of detail of FIG. 43 showing the wedge plate and jaw members;

FIG. 48 is a side view, shown in section, of the handle housing at the beginning of an initial stroke;

FIG. 49 is an enlarged area of detail of FIG. 48 showing the rack and pawl;

FIG. 50 is an enlarged area of detail of FIG. 48 similar to FIG. 49;

FIG. 51 is a side view, shown in section, of the feed bar and trip lever;

FIG. 52 is a side view, shown in section, of the follower;

FIG. 57 is a top view of the wedge plate and cam link moving distally;

FIG. 58 is a side view, shown in section, showing the movement of the flexible leg cammed out of a wedge plate window;

FIG. 74 is a side view of the handle housing with the trigger at full stroke;

FIG. 75 is an enlarged area of detail of FIG. 74 with the pawl clearing the teeth on the rack;

FIG. 76 is a side view, shown in section, of the driver camming the jaws closed about a surgical clip;

FIGS. 77 to 79 are sequential views of the driver camming the jaws closed about a surgical clip;

DETAILED DESCRIPTION

Figure 1:
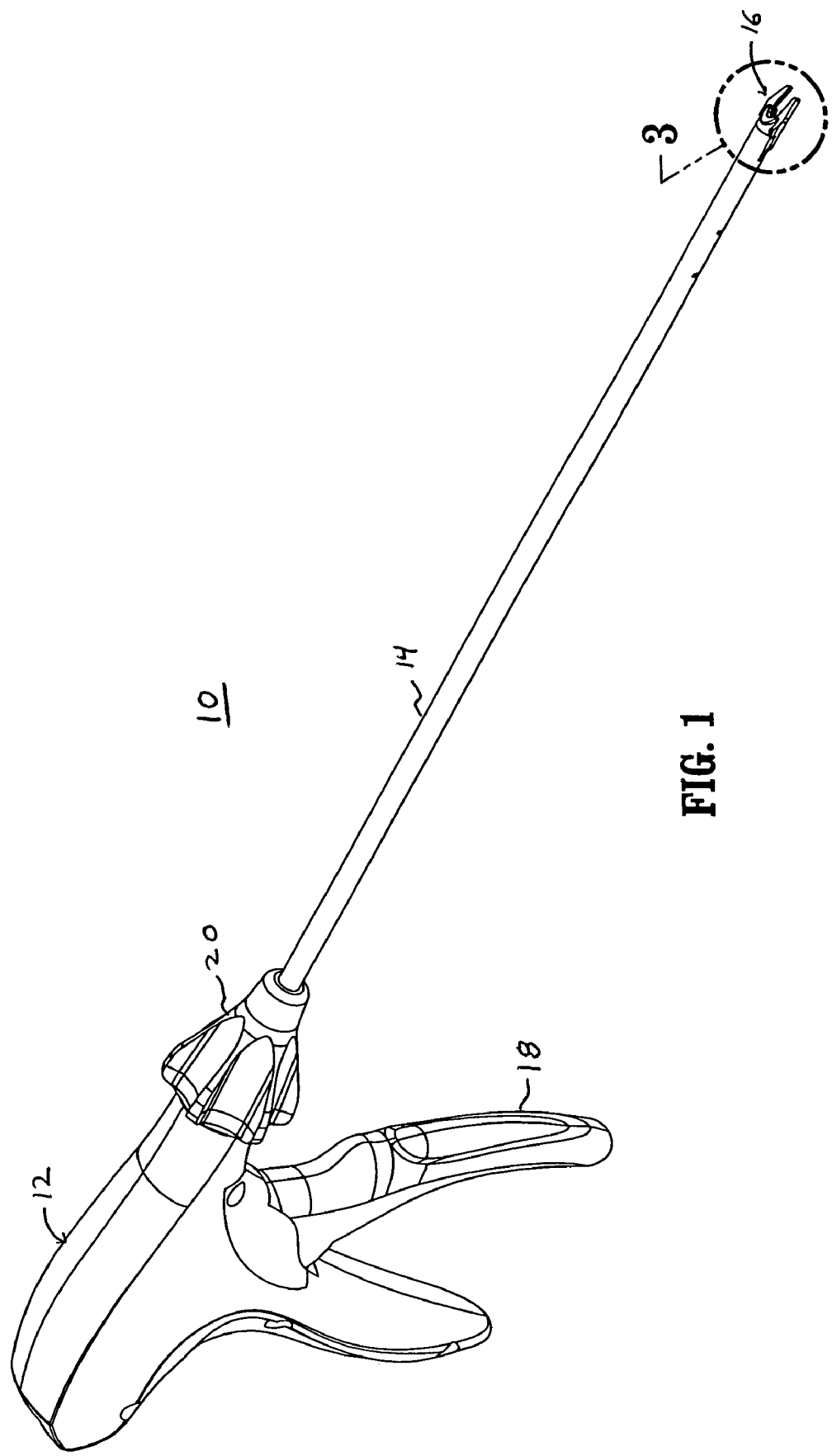
FIG. 1 is a perspective view of a surgical clip applier.

There is disclosed a novel endoscopic surgical clip applier having a jaw control mechanism configured to maintain jaws of the surgical clip applier in a spaced apart and stable position during insertion of a surgical clip. It should be noted that, while the disclosed jaw control mechanism is shown and described in an endoscopic surgical clip applier, the disclosed jaw control mechanism is applicable to any surgical clip applier or other instrument having a pair of compressible jaws.

Referring now to FIGS. 1-5, surgical clip applier 10 generally includes a handle assembly 12 and an endoscopic portion including an elongated tubular member 14 extending distally from handle assembly 12. Handle assembly 12 is formed of a plastic material while elongated tubular member 14 is formed of a biocompatible material such as stainless steel. Elongated tubular member 14 of surgical clip applier 10 may have various outer diameters such as an outer diameter of 5 m or 10 mm depending on intended use. Further, elongated tubular member may have various elongated or shortened lengths depending on intended use, such as, for example, in bariatric surgery. In one embodiment, the elongated tubular member 14 in bariatric surgery may have a length that is in excess of 30 centimeters. In one preferred embodiment of bariatric surgery, the length of the elongated tubular member 14 is 33 centimeters. In another preferred embodiment, the length of the elongated tubular member 14 for bariatric surgery is 37 centimeters. In still another preferred embodiment, the length of the elongated tubular member 14 for bariatric surgery is 40 centimeters, however one skilled in the art should appreciate that the outer tubular member 14 may have any length in excess of 30 centimeters and the present disclosure is not limited to any of the above embodiments. A pair of jaws 16 are mounted on the distal end of elongated tubular member 14 and are actuated by a trigger 18 movably mounted in handle assembly 12. Jaws 16 are also formed of a biocompatible material such as stainless steel or titanium. Notably, in some embodiments, when jaws 16 are in an open condition relative to each other, the maximum width of jaws 16 measure less than or equal to the outer diameter of elongated tubular member 14 to allow insertion through a trocar or other part in a body in a open condition. This is particularly true of the 10 mm clip applier. Jaws 16 are mounted such that they are longitudinally stationary relative to elongated tubular member 14. A knob 20 is rotatably mounted on a distal end of handle assembly 12 and affixed to elongated tubular member 14 to provide 360 degree rotation of elongated tubular member 14 and jaws 16 about its longitudinal axis. Referring for the moment to FIG. 3, jaws 16 define a channel 22 for receipt of a surgical clip therein.

As best shown in FIGS. 2 and 4 a window 200 is provided in handle assembly 12 to view an indicator, such as, for example, a counter mechanism associated with handle assembly 12.

Figure 6:
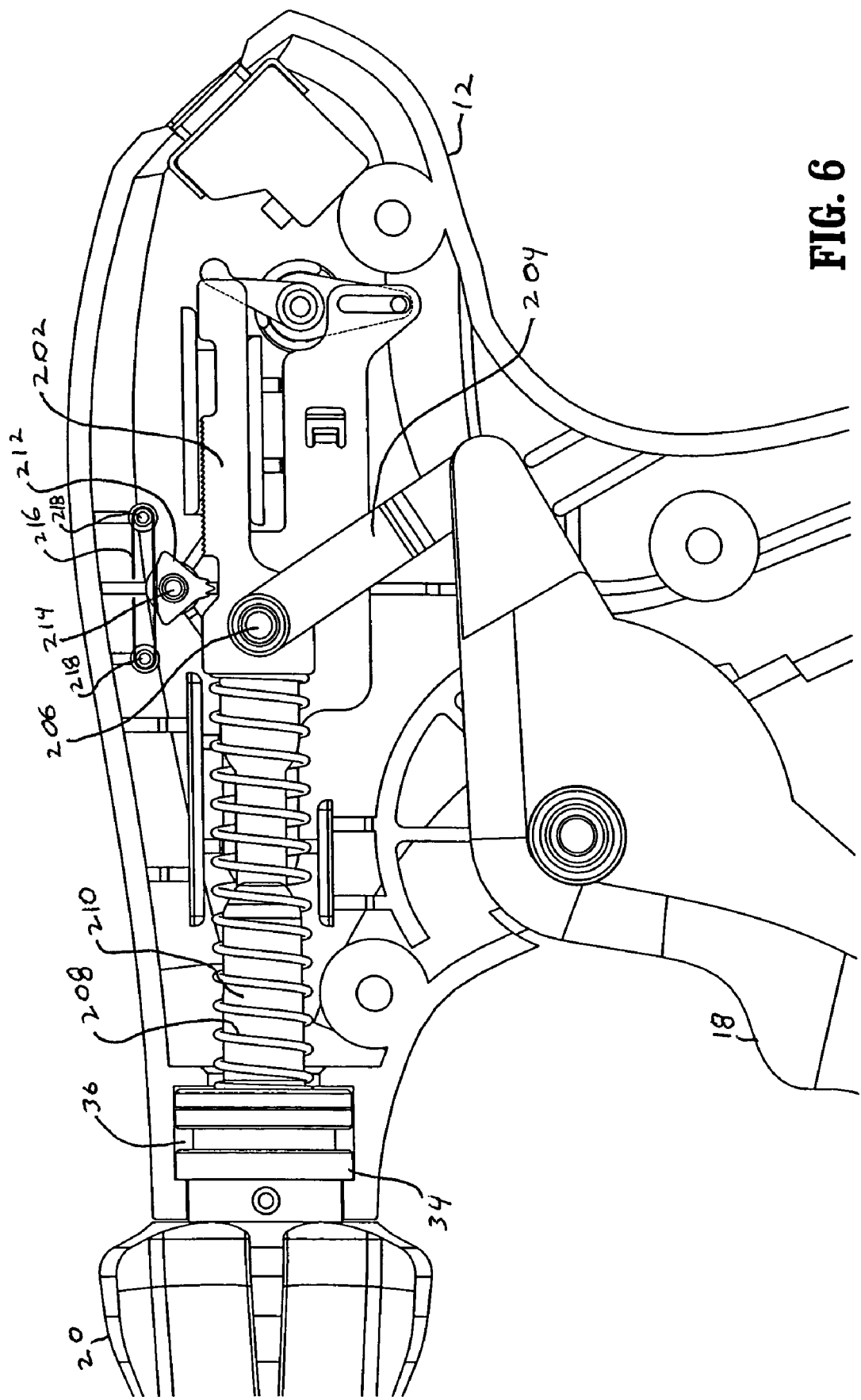
FIG. 6 is a side view, with half of the body removed, of the handle assembly of the surgical clip applier.
Figure 7:
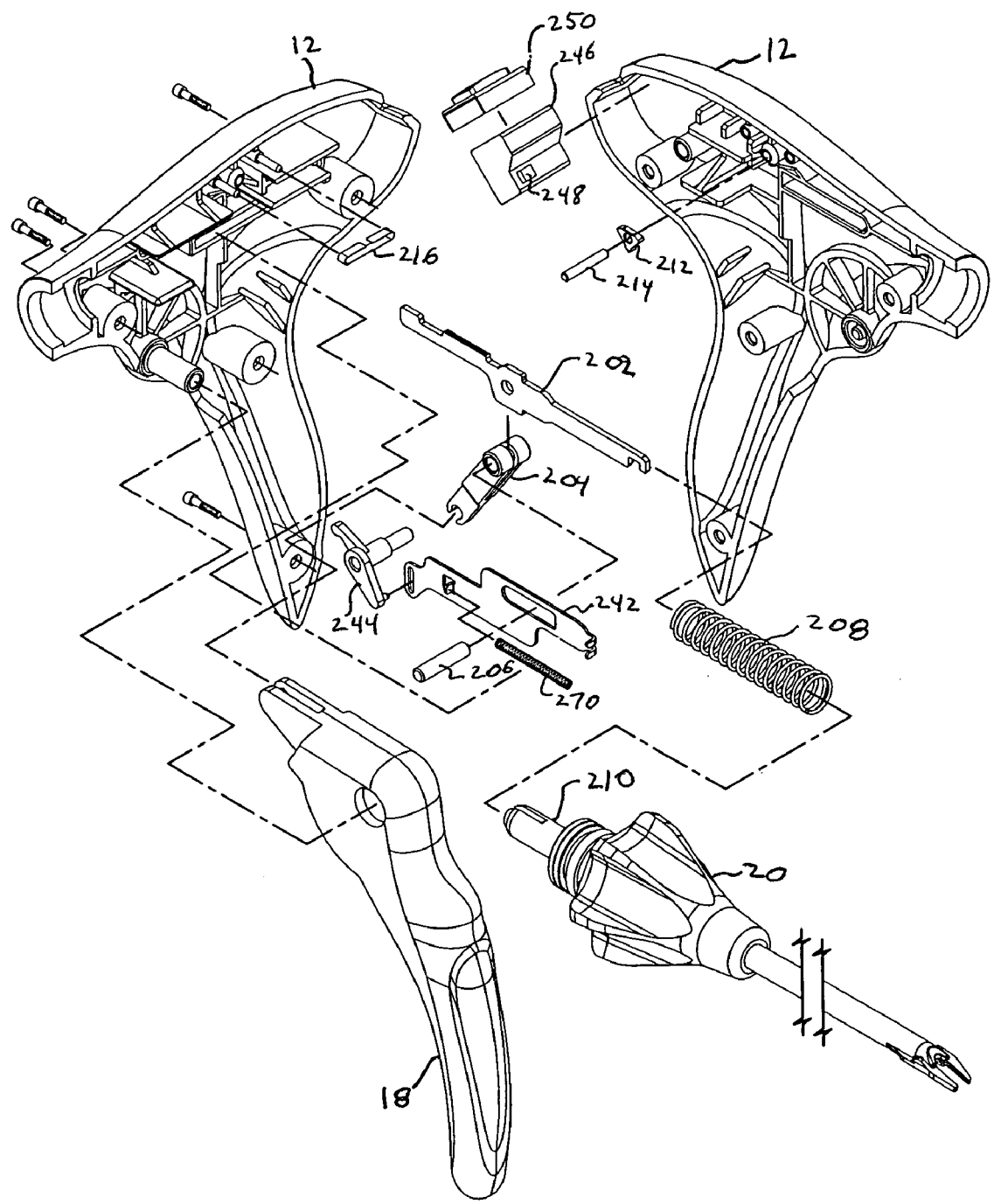
FIG. 7 is an exploded perspective view of the handle of the clip applier, with shaft assembly.

Referring now to FIGS. 6 through 7, handle assembly 12 of clip applier 10 is shown. Handle assembly 12 includes a longitudinally movable rack 202 which is connected to trigger 18 by means of a wishbone link 204. A pin 206 is provided to connect wishbone link 204 to rack 202. Rack 202 is provided for advancing and crimping a surgical clip between jaws 16 in response to actuation of trigger 18. Rack 202 is biased to a proximal position by a return spring 208 positioned between rack 202 and a bushing 210 that is mounted within journal 36 in housing 12.

In order to prevent inadvertent return of trigger 18 and rack 202 before full actuation of surgical instrument 10, a pawl 212 is movably mounted on a pawl pin 214. Pawl 212 is engageable with rack 202 in a manner discussed in more detail hereinbelow. A pawl spring 216 is provided between spring posts 218 in order to bias pawl 212 into engagement with rack 202.

Referring for the moment to FIG. 8, pawl 212 includes a pawl hole 220 for mounting pawl 212 on pawl pin 214. Pawl 212 also includes pawl teeth 222 engageable with rack 202 in a manner described below.

Referring to FIGS. 7, 9 and 9A, rack 202 generally includes a rack hole 224 for connecting rack 202 to wishbone link 204 by means of pin 206. Rack 202 also includes rack teeth 226 which are engageable with pawl teeth 222 to restrict longitudinal movement of rack 202 within handle assembly 12. Rack 202 is also provided with a distal recess 228 and a proximal recess 230. Recesses 228 and 230 are provided to allow pawl 212 to reverse and advance back over rack 202 when rack 202 reverses to proximal movement. A distal hook 232 is provided on rack 202 to engage rack 202 with the various drive mechanisms in a manner described hereinbelow. Thus, actuation of trigger 18 drives wish bone link 204, thereby driving rack 202 distally through wishbone link 204 and against the bias of return spring 208.

Figure 9F:
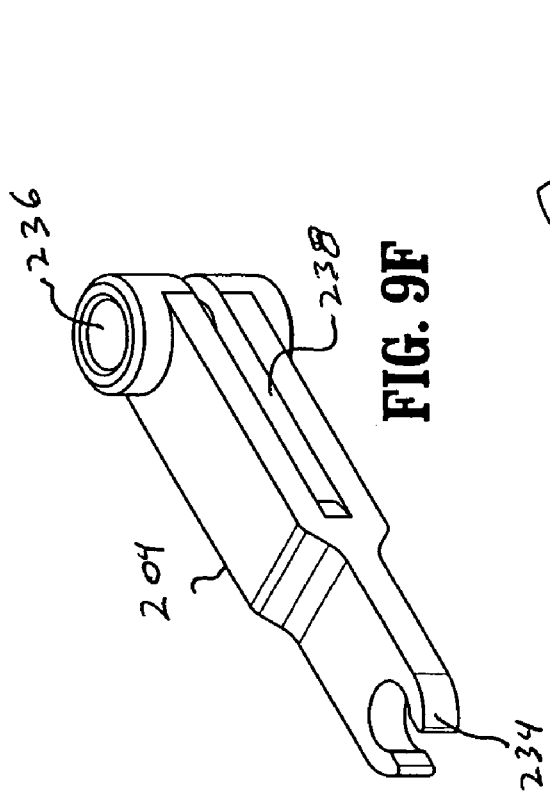
FIGS. 9F and 9G are opposite perspective views of a wishbone link.
Figure 9G:
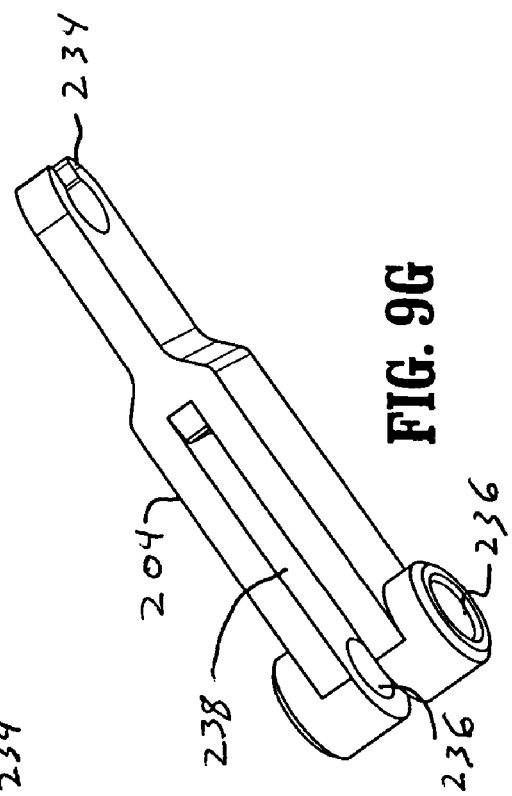

Referring for the moment to FIGS. 9F and 9G, wishbone link 204, as noted above, is provided to connect trigger 18 to rack 202. Specifically, wishbone link 204 includes a snap fit end or locking feature 234 which is engageable with a post (now shown) on trigger 18. Bores 236 formed at an opposing end of wishbone link 204 are provided to mount on rack pin 206. A slot 238 provided in wishbone link 204 allows wishbone link 204 to support rack 202 from opposite sides thereof. Linkage mechanism, including trigger 18 and wish bone link 204, allows for a greater mechanical advantage while minimizing the space the linkage mechanism occupies in handle assembly 12. Knob 20 includes a flange 34 which is also rotatably mounted in a journal 36 in housing 12.

Figure 6A:
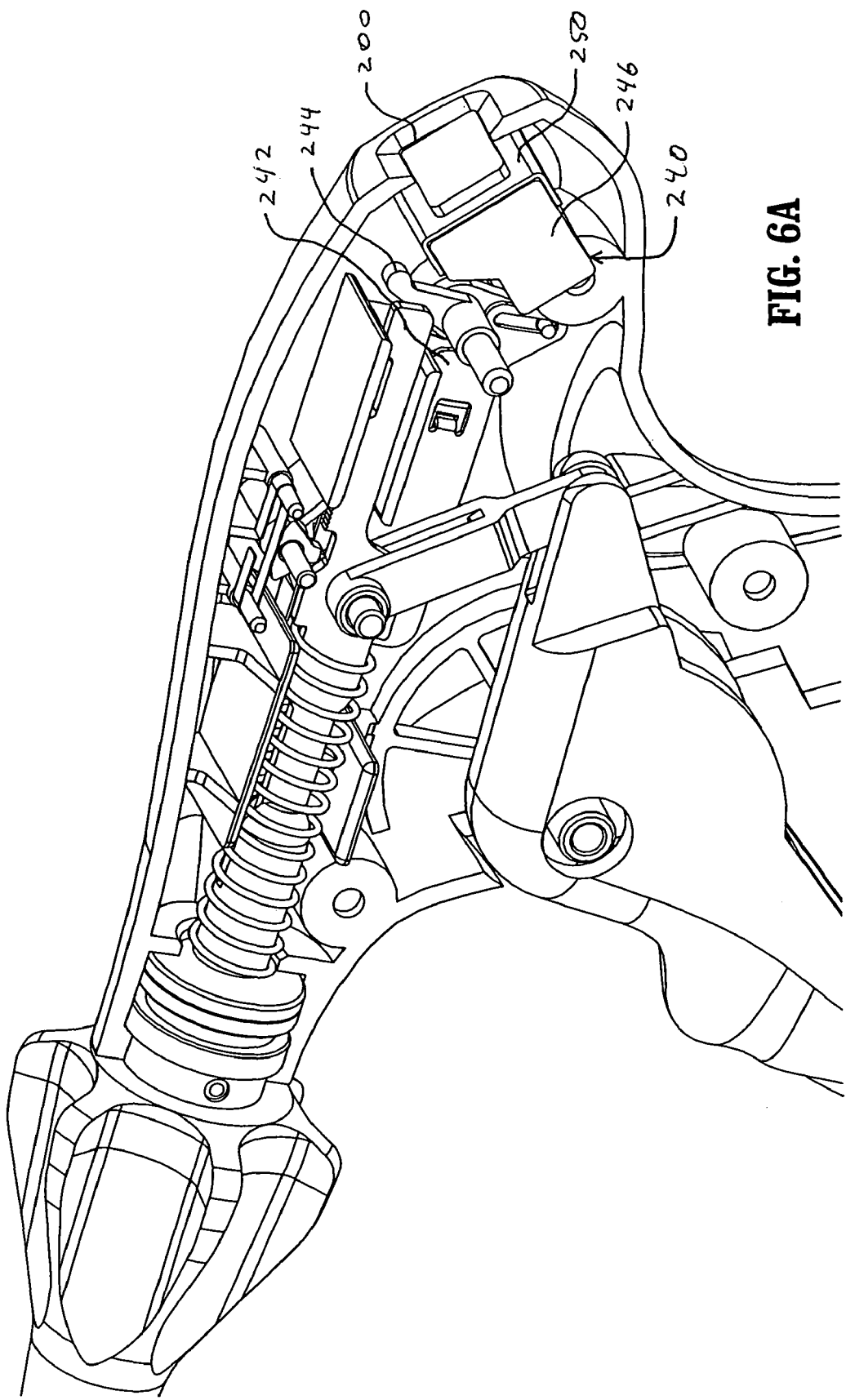
FIGS. 6A and 6B are perspective views, with half of the body removed, of the handle assembly of the surgical clip applier.
Figure 6B:
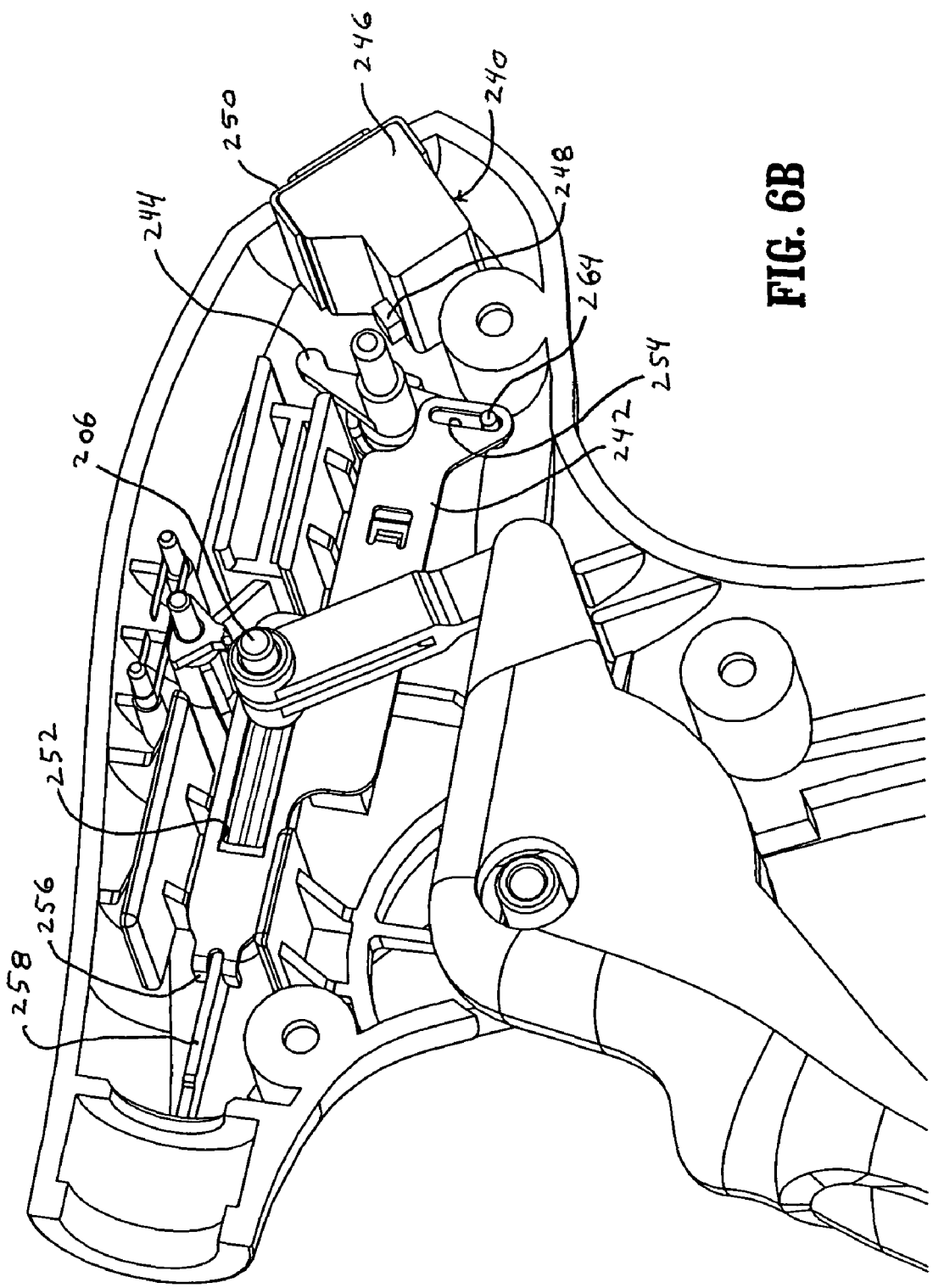

Referring now to FIGS. 6A and 6B, and as noted above, handle assembly 12 is provided with a window 200 at a proximal end thereof revealing an indicator mechanism associated with handle assembly 12. Thus, there is provided a novel counter mechanism 240 which is configured to provide an indication of either the number of clips fired or the number of clips remaining within surgical instrument 10. Counter mechanism 240 is triggered by an actuator 242 associated with handle assembly 12 via a toggle arm 244 pivotally mounted to handle assembly 12. Counter mechanism 240 generally includes a counter 246 having an actuation feature 248, such as, a leaf spring and contact, button, etc. which is tripped or actuated by toggle arm 244 in response to actuation of trigger 18. A lens 250 is provided in between counter 246 and counter window 200 to protect counter 246 or enhance magnification of alpha-numeric digits during operation. Counter 246 can be of the liquid crystal display (LCD) light emitting diode (LED) or analog/mechanical type. Counter 246 may also include a printed circuit board, battery and a backlight or lighted display. Counter 246 can be configured to count down from the total number of surgical clips originally provided in surgical instrument 10 to indicate the number of clips remaining. Alternatively, counter 246 can count up from 0 to the total number of clips already fired. One contemplated counter 246 is an LCD counter module available from Golden View Display, Inc. The counter 246 may be any device known in the art to provide an indication of an event. The event may be related to the procedure or the operation of the clip applier 10. The counter 246 in a preferred embodiment may be various types of liquid crystal displays. However, in another embodiment, the display may be one or more light emitting diodes, a luminescent display, a multi-color display, a digital display, an analog display, a passive display, an active display, a so called "twisted nematic" display, a so called "super twisted nematic" display, a "dual scan" display, a reflective display, a backlit display, an alpha numeric display, a monochrome display, a so called "Low Temperature Polysilicon Thin Film Transistor" or LPTS TFT display, or any other display that indicates a parameter, information or graphics related to the procedure or the clip applier 10. In one embodiment, the display is a liquid crystal display or "LCD". The LCD may be a black and white or color display that displays one or more operating parameters of the clip applier 10 to the surgeon. In one embodiment, the displayed parameter may be an amount of remaining clips, a number clips that have been used, a position parameter, a surgery time of usage, or any other parameter of the procedure.

Referring for the moment to FIGS. 9B and 9C, the specific structure of actuator 242 will now be described. As noted above, actuator 242 is configured to index counter mechanism 240 in response to movement of trigger 18 thus actuator 242 includes a drive slot 252 which is configured to be positioned about pin 206 extending through rack 202 and wishbone link 204. Drive slot 252 allows surgical instrument 10 to be actuated through a predetermined length of stroke prior to pin 206 engaging actuator 242. A connecting slot 254 is provided to engage a corresponding pin on toggle arm 244 in order to bias toggle arm 244 against counter 246. In order to prevent any flexing or wobbling of actuator 242 during its reciprocal movement within handle assembly 12 actuator 242 is provided with a pair of fingers 256 which are configured to ride along a housing rail 258 formed in handle assembly 12 (FIG. 6B). A tab 260 (FIGS. 6C and 6D) is provided on actuator 242 to engage a return spring in a manner described in more detail hereinbelow.

Figure 9D:
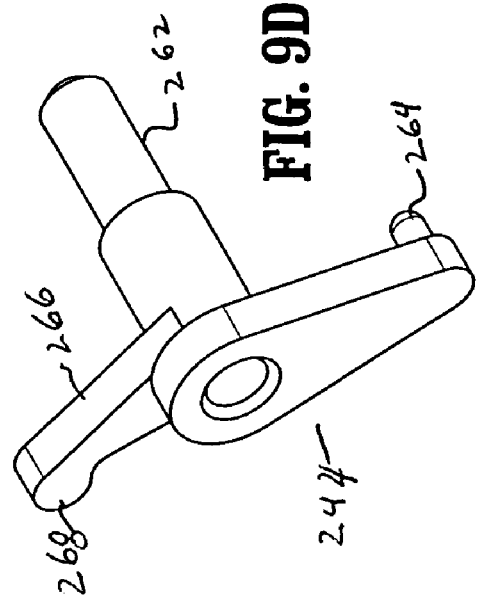
FIGS. 9D and 9E are opposite perspective views of a toggle arm.
Figure 9E:
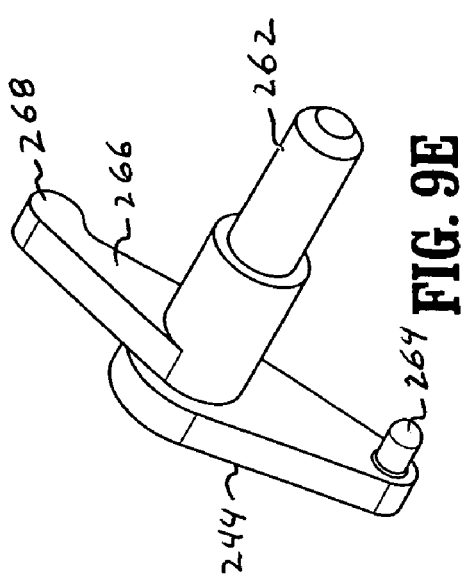

Referring for the moment to FIGS. 9D and 9E counter lever 244 includes a post 262 which is pivotally mounted into housing assembly 12. A first end of toggle arm 244 includes a pin 264 which is engageable within connecting slot 254 in actuator 242 such that longitudinal movement of actuator 242 within housing assembly 12 pivots counter lever 244 about stud 262. An opposed end of toggle arm 244 includes a contact lever 268 which is configured to engage and depress counter button 248 on counter 246 to trigger or increment counter 246 in any number of predetermined fashions either up or down numerically.

Figure 6C:
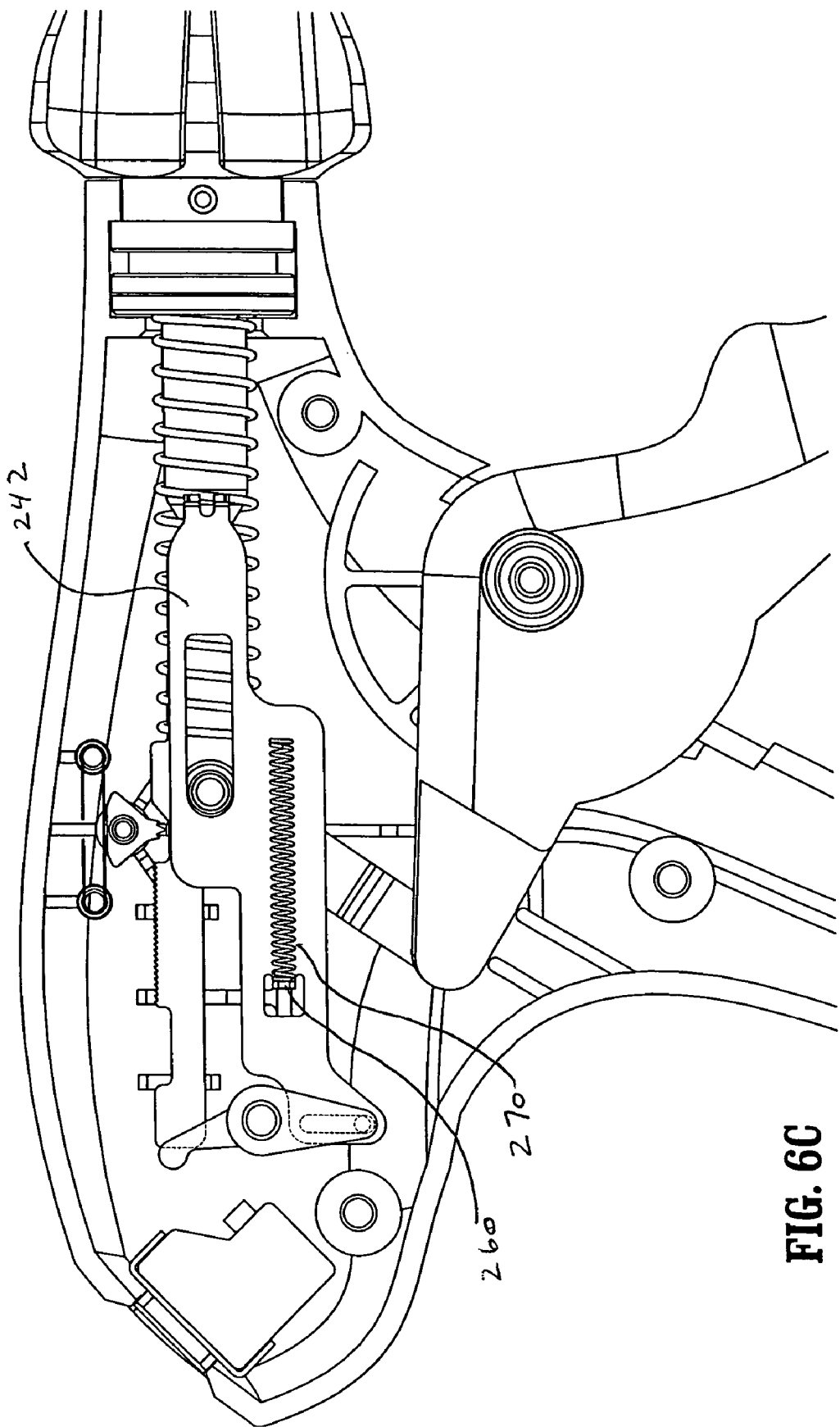
FIG. 6C is a side view, with half of the body removed, of the handle assembly of the surgical clip applier.
Figure 6D:
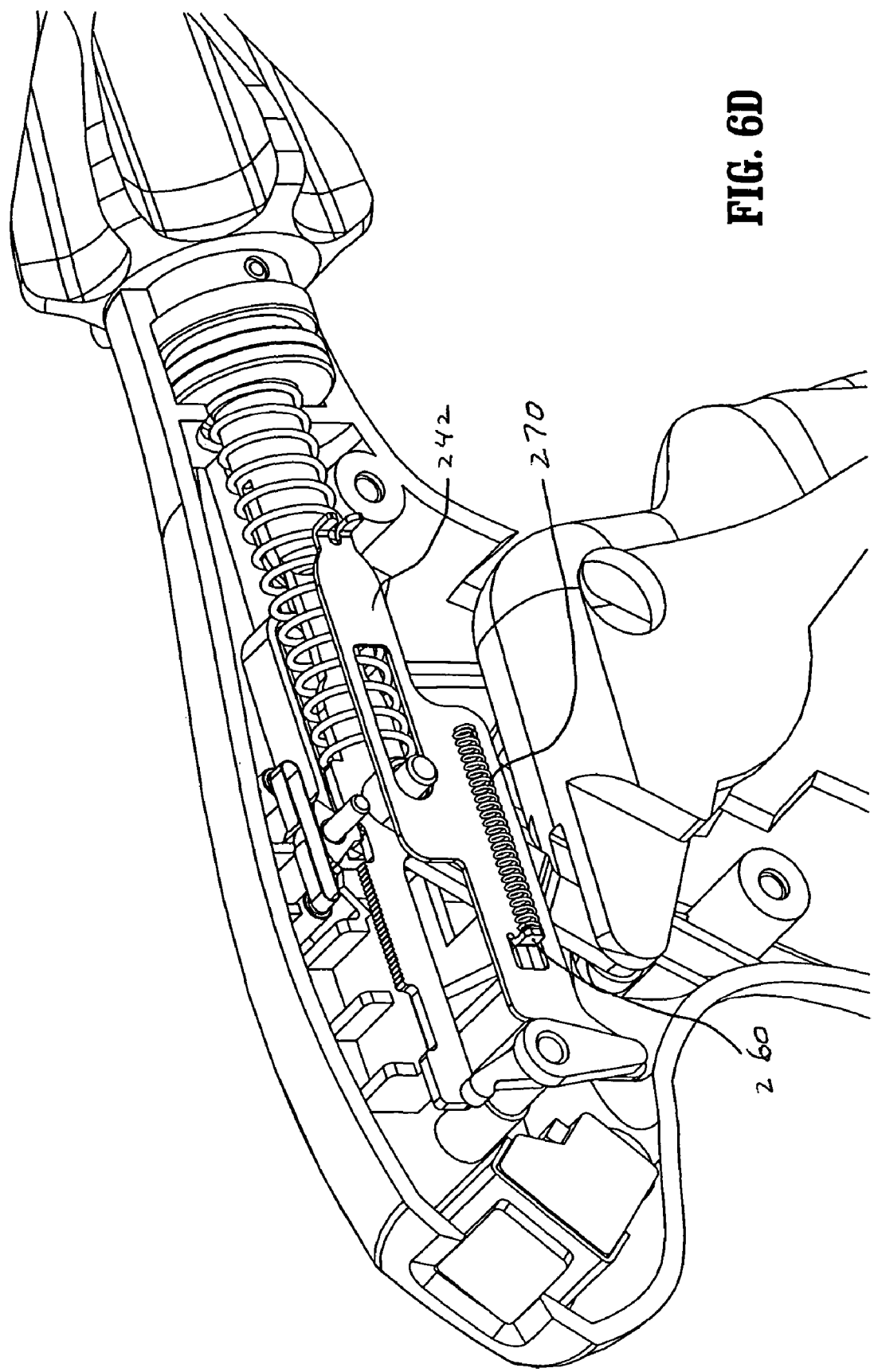
FIG. 6D is a perspective view, taken from the opposite side, of the handle assembly of the surgical clip applier with half the body removed.

The arrangement of the various components of the counter mechanism 240, actuator 242 and counter lever 244 mounted within handle assembly, is best illustrated in FIGS. 6B to 6D. Referring initially to FIG. 6B, wherein rack 202 has been removed for clarity, it can be seen that fingers 256 of actuator 242 ride along housing rail 258 formed in housing assembly 12. Pin 206 associated with wishbone link 204 rides within drive slot 252. At a proximal end of actuator 242 pin 264 on counter lever 244 is positioned within connecting slot 254.

Referring now to FIGS. 6C and 6D, in order to maintain counter lever 244 out of engagement with counter mechanism 240 prior to actuation of trigger 18 there is provided a compression spring 270 which is engageable with tab 260 on actuator 242. An opposed end of compression spring 270 engages a corresponding projection formed on opposed side of housing handle assembly 12 in order to bias actuator 242 in a proximal most direction.

Combinations of the various elements and mechanisms associated with clip applier 10 will now be described.

Figure 10:
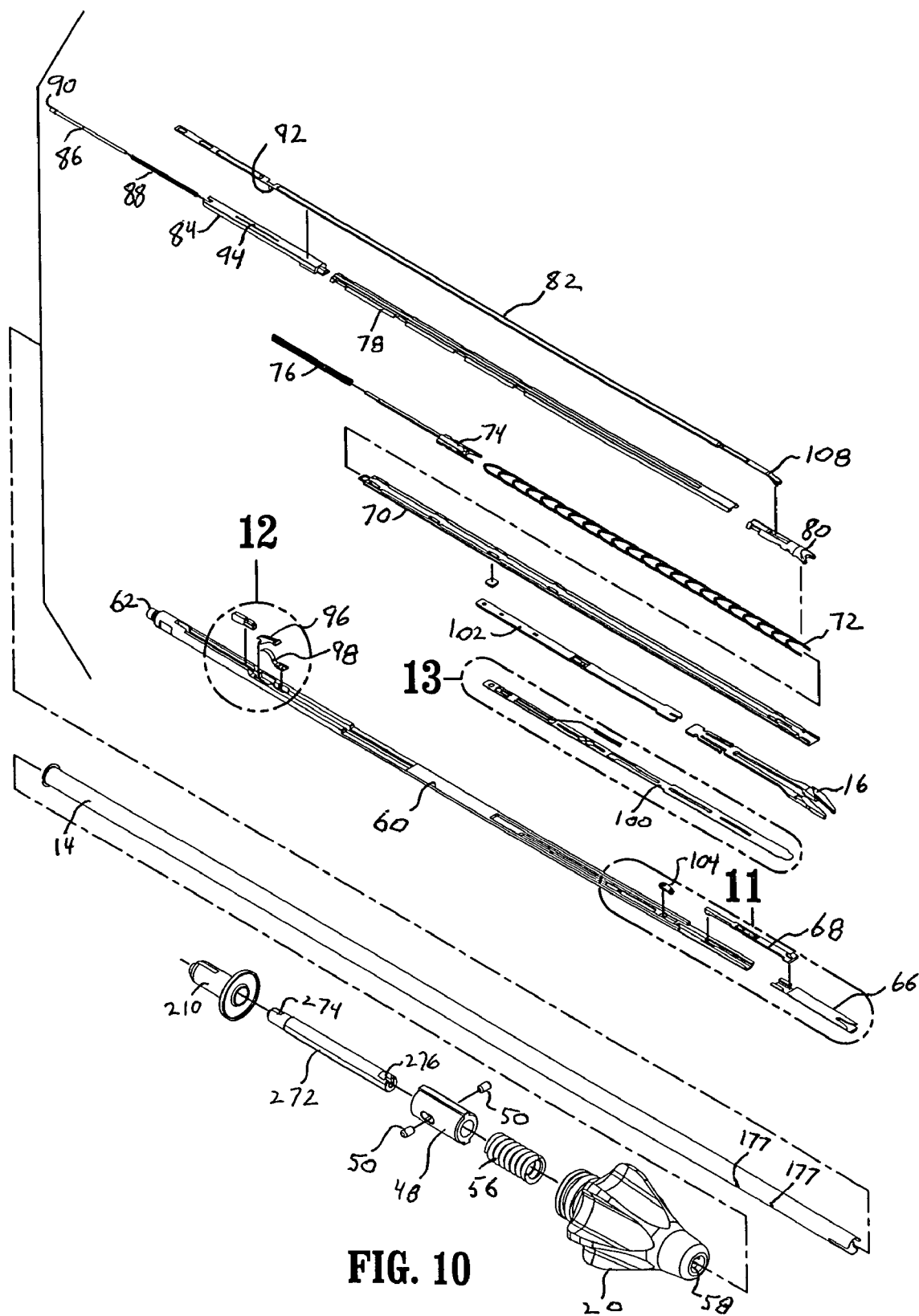
FIG. 10 is an exploded perspective view of the shaft assembly of the surgical clip applier.

Referring to FIG. 10, a bushing 48, including retention pins 50, is provided to secure the bushing 210 to the knob 20. A drive link 272 is connected, to rack 202 (FIGS. 6 and 7) such that a proximal end of drive link 272 engages rack 202. Specifically, distal hook 232 of rack 202 engages a slot 274 in a proximal end of drive link 272. An over pressure mechanism including an impact spring 56 is provided about outer tube 14 between bushing 48 and housed in a bore of knob 20 to prevent over compression of jaws 16 during actuation of the instrument in a manner described in more detail hereinbelow. Drive link 272 extends within a bore 58 in knob 20.

A flange located at a proximal end of elongated tube member 14 abuts a proximal end of bushing 48 (FIGS. 7D and 7E).

With continued reference to FIG. 10, in order to actuate the various components there is provided an actuation mechanism or spindle 60 mounted for longitudinal movement through elongated tubular member 14. Spindle 60 includes a boss 62 at its proximal end which is engageable with a recess 276 on the distal end of spindle link 272. (FIG. 7A) by positioning boss 62 of spindle 60 within a recess 276 of spindle link 272, spindle 60 can rotate with the outer tube assembly independent of the longitudinal motion of spindle link 272 and spindle 60. As best shown in FIG. 7B bushing 48 is positioned within knob 20 and secured therein by means of retention pins 50.

Referring for the moment to FIGS. 7C and 7E, bushing 48 is provided with a pair of opposed longitudinal ribs 278 which fit within corresponding slots 280 in knob 20 for the purpose of orientation.

Referring now to FIGS. 7D and 7E, it can be seen that tabs 282 formed on an inner surface of the proximal end of bushing 48 are configured to engage corresponding cutouts 284 on outer tube 14. Thus, outer tube 14 is allowed to rotate in response to rotation of knob 20.

Referring to FIG. 10, a camming mechanism including a driver 66 and a slider joint 68 extend from a distal end of spindle 60 to cam closed jaws 16 about a surgical clip.

Clip applier 10 is configured to retain a plurality of surgical clips for application to tissue. Clip applier 10 includes an elongated channel member 70 configured to retain a plurality of surgical clips 72 and convey surgical clips 72 to jaws 16. It should be noted that channel member 70 and jaws 16 do not move longitudinally relative to elongated tubular member 14. A follower 74 is biased by a spring 76 to urge surgical clips 72 distally within channel member 70. A channel cover 78 overlies channel 70 to retain and guide spring 76 and surgical clips 72 therein. A nose 80 is provided at a distal end of channel cover 78 to assist in directing surgical clips 72 into jaws 16.

A feeder mechanism including a feed bar 82 is provided for longitudinal movement relative to channel cover 78 in order to advance individual clips 72 into jaws 16. A trip block 84 having a guide pin 86 and a feed bar spring 88 are provided adjacent the proximal end of channel cover 78 to bias feed bar 82 in a proximal direction. Specifically, a proximal end 90 of guide pin 86 is interconnected with a hook 92 on an underside of feed bar 82 and through slot 94 in trip block 84. (See also FIG. 10) In order for spindle 60 to move feed bar 82, spindle 60 is provided with a trip lever 96 and a biasing spring 98. Trip lever 96 is engageable with a proximal end of feed bar 82 in a manner described in more detail herein below.

A notable advantage of presently disclosed clip applier 10 is that it is provided with a wedge plate 100 which is configured to advance into jaws 16 during actuation of surgical clip applier 10 and maintain jaws 16 in a spaced apart condition while receiving a surgical clip 72. Cam slot 136 (FIG. 13), described in detail hereinbelow, formed through wedge plate 100 and a filler component 102 mounted within elongated tubular member 14, cooperate in connection with a cam link 104, provided on spindle 60, to move wedge plate 100 relative to filler component 102 and jaws 16. Filler component 102 is positioned directly behind jaws 16 and does not move relative to elongated tubular member 14.

Turning to FIG. 10A, and as noted above, feed bar 82 is provided to move surgical clips 72 into jaws 16. Feed bar 82 is driven by trip lever 96 on spindle 60. (See FIG. 10.) Specifically, feed bar 82 is provided with an elongated window 106 which is configured to be engaged by trip lever 96 as spindle 60 is driven distally. Feed bar 82 also includes a window 286 for receipt of lockout structure as described herein below. To facilitate insertion of the clip into jaws 16, feed bar 82 is provided with a pusher 108 at its distal end which is configured to advance an individual clip 72 out of the line of clips 72 and into jaws 16. As shown in FIG. 10B, follower 74 is positioned behind the line of clips to advance clips 72 through surgical clip applier 10. As shown in FIG. 10H, follower 74 includes an abutment surface 288 for engagement with further lockout structure located on a distal end of clip channel 70.

Referring to FIG. 10C, as noted above, trip block 84 includes a slot 94 to receive hook 92 of feed bar 82. In order to disengage trip lever 96 from window 106 and thus feed bar 82, trip block 84 is provided with an angled surfaces 110 which is configured to engage trip lever 96 and disengage it from window 106 of feed bar 82 as best shown in FIG. 10D.

Referring now to FIGS. 10E-10G, various features of spindle 60 will now be described. A perspective view of spindle 60, isolated from other components is shown in FIG. 10E. With specific reference to FIG. 10F, at a proximal end, spindle 60 includes a pivot point 112 for attachment of trip lever 96 at its proximal end. Additionally, a boss 114 is provided in spindle 60 for attachment of biasing spring 98 to bias trip lever 96 into engagement with window 106 of feed bar 82. An angled surface 290 is provided to engage spindle 60 with lockout structure and prevent spindle from completely retracting after a final clip has been fired. With respect to FIG. 10G, at a distal end, spindle 60 is provided with a boss 116 for mounting cam link 104. Spindle 60 is additionally provided with a raised feature 118 which functions to disengage filler component 102 from wedge plate 100 in a manner described in hereinbelow.

Referring to FIG. 11, spindle 60 is provided to advance driver 66 into engagement with jaws 16 to close jaws 16 about a surgical clip after the surgical clip has been positioned within jaws 16. A distal end 120 of slider joint 68 resides in a recess 122 in driver 66. A proximal projection 124 of slider joint 68 rides within a longitudinal slot 126 in the distal end of spindle 60. The length of longitudinal slot 126 allows spindle 60 to move a predetermined longitudinal distance before engaging and moving driver 66 longitudinally to close jaws 16 about a clip 72. A latch retractor 128 is integrally formed within a slot 130 in slider joint 68 so as to allow driver 66 to be driven distally after wedge plate 100 has been allowed to retract proximally in a manner described in more detail hereinbelow.

Referring to FIG. 12, clip applier 10 is provided with novel lock out structure to prevent actuation of clip applier 10 after a last clip 72 has been dispensed. Clip applier 10 includes a lockout wedge 292 which is movably mounted within a channel 294 in spindle 60. Lockout wedge 292 includes an angled surface 296 configured to cam against angled surface 290 on spindle 60. A raised projection 298 mates with window 286 in feed bar 82 to affix lockout wedge 292 to feed bar 82 during longitudinal movement thereof.

Figure 13:
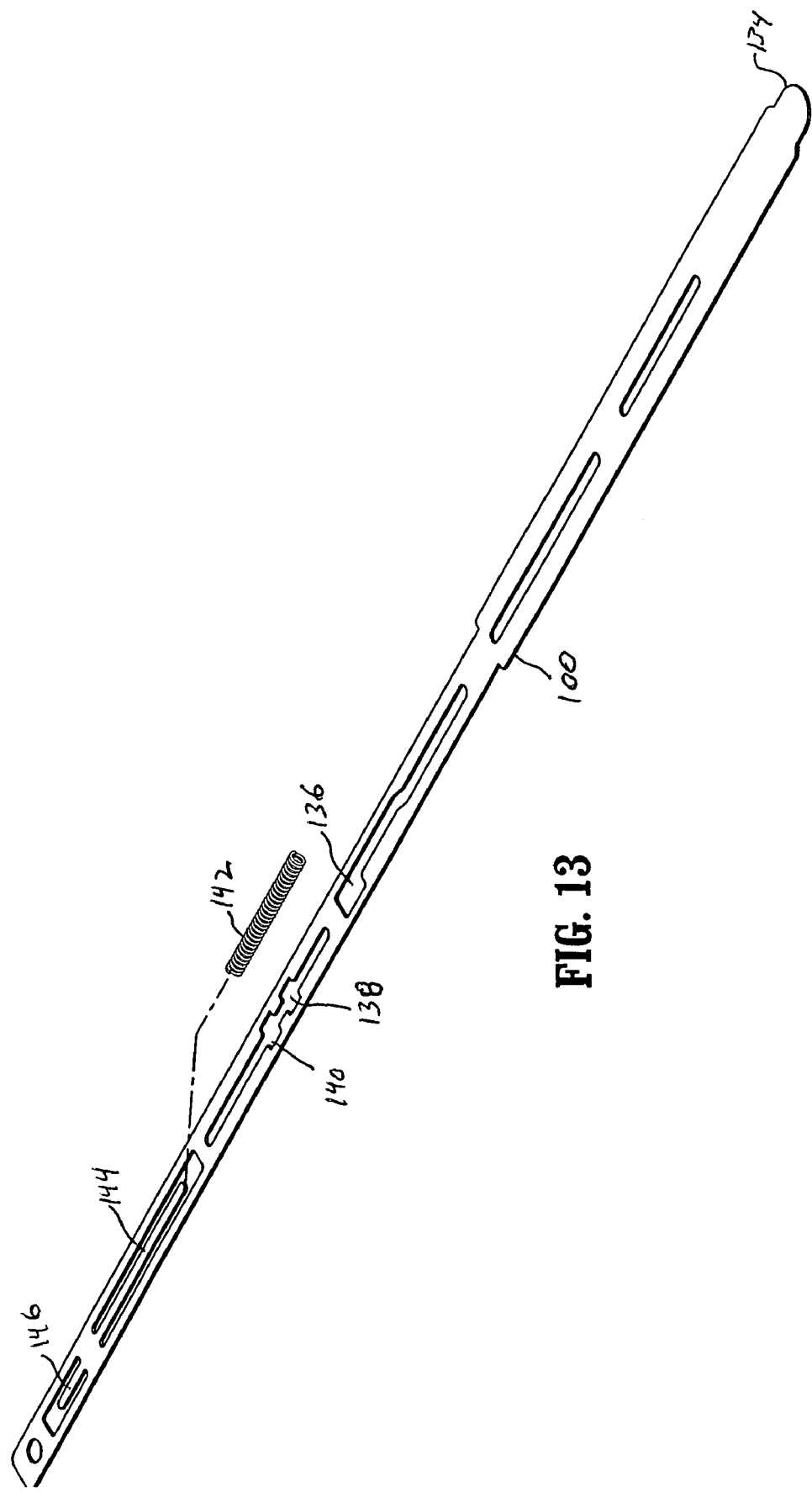
FIG. 13 is a perspective view of a wedge plate and biasing spring.

Referring now to FIG. 13, wedge plate 100 will be described in more detail. As noted above, wedge plate 100 is provided to bias and maintain jaws 16 in a spaced apart condition during loading of a surgical clip 72 within jaws 16. Additionally, the presence of wedge plate 100 provides stability to jaws 16 to prevent them from flexing during loading of surgical clip 72. As shown, wedge plate 100 includes a distal tip 134 which is configured to engage and cam jaws 16 open and maintain them in a spaced condition. Additionally, wedge plate 100 includes a cam slot 136 which is configured to cooperate with cam link 104 mounted on spindle 60 to control the motions of wedge plate 100 as discussed in more detail below. Further, distal and proximal windows 138 and 140, respectively, are provided to engage flexible structure on the filler component 102. A biasing spring 142 is provided on a mount 144 to bias wedge plate 100 generally proximally within elongated tubular member 14. Finally, a stop 146 is configured to engage corresponding structure on filler component 102.

Referring now to FIGS. 14 and 15, various aspects of filler component 102 will now be described. Filler component 102 includes a flexible leg 152 which is configured to engage distal and proximal windows 138 and 140 in wedge plate 100. Filler component 102 also includes an elongated cam slot 148 configured to receive part of cam link 104. A disengaging edge 150 is provided within cam slot 148 to facilitate disengaging cam link 104 from within cam slot 136 in wedge plate 100. Filler component 102 additionally includes a stop 154 for engagement with tongue 146 on wedge plate 100 (FIG. 13), to limit the proximal retraction of wedge plate 100, as well as a longitudinal recess 156 to accommodate the length of return spring 142 of wedge plate 100.

FIGS. 16 and 17 illustrate the position of impact spring 56 relative to rotation knob 20. As noted above, impact spring 56 is provided as an over pressure mechanism to prevent over compression of jaws 16 during the crimping of a surgical clip 72 as described in more detail below with respect to the operation of surgical clip applier 10. The over pressure mechanism is designed to prevent overstroke of trigger 18 applied by the surgeon and ultimately prevent damage to jaws 16.

Referring to FIGS. 18-20, spindle 60 and related drive components are shown with elongated tubular member 14 removed. Specifically, with regard to FIG. 19, pusher 108 of feed bar 82 extends through a slot 158 in nose 80 to engage a surgical clip 72. Similarly, as shown in FIG. 20, at a proximal end of spindle 60, trip lever 96 extends through window 106 in feed bar 82. In this position, trip lever 96 can engage an edge of slot 106 to drive feed bar 82 distally along with spindle 60 through elongated tubular member 14. Lockout wedge 292 is longitudinally movable within channel 294 in spindle 60. Projection 298 on lockout wedge mates with window 286 in feedbar 82.

Figure 21:
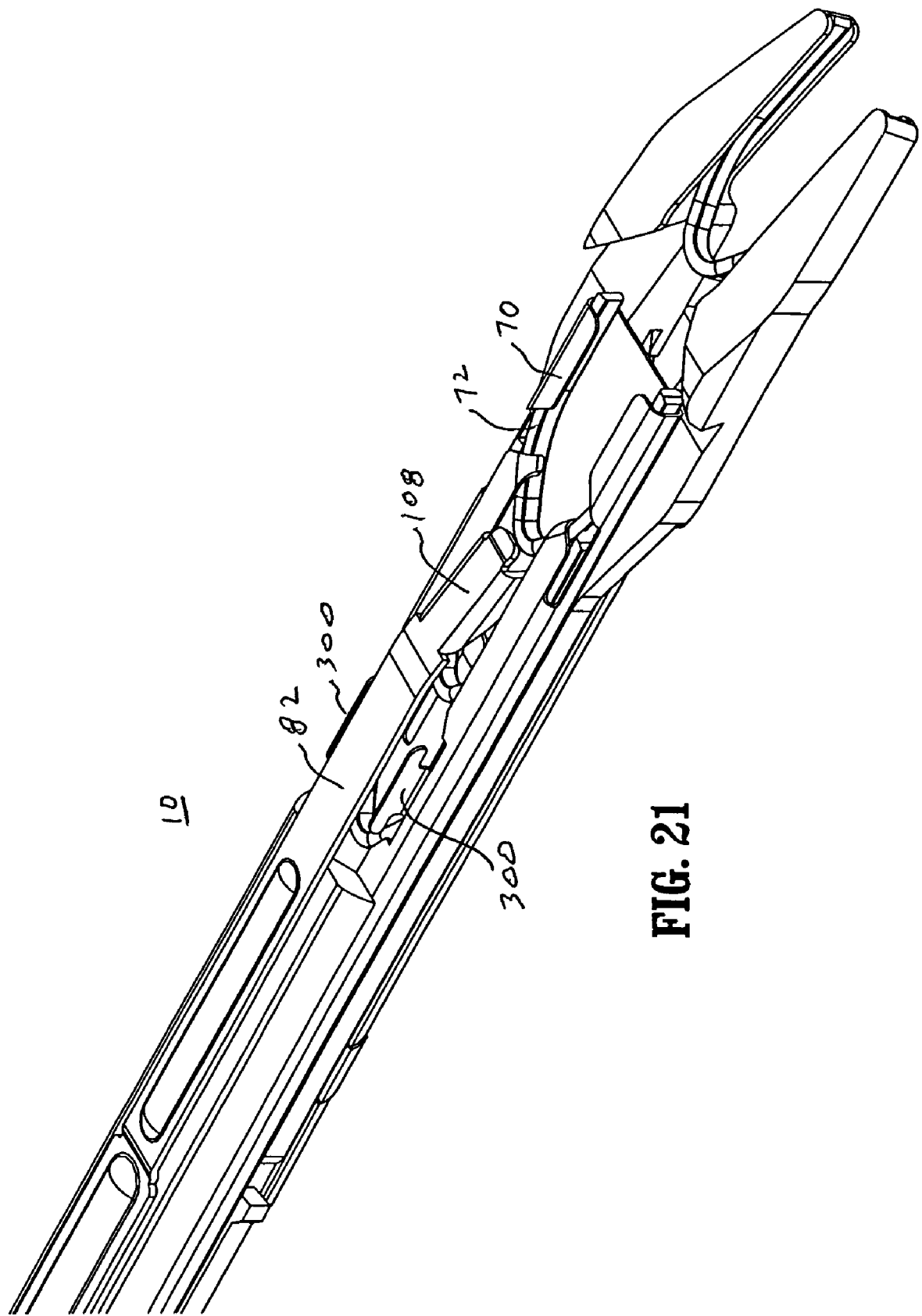
FIG. 21 is an enlarged view of the distal end of the surgical clip applier with outer tube removed.
Figure 37:
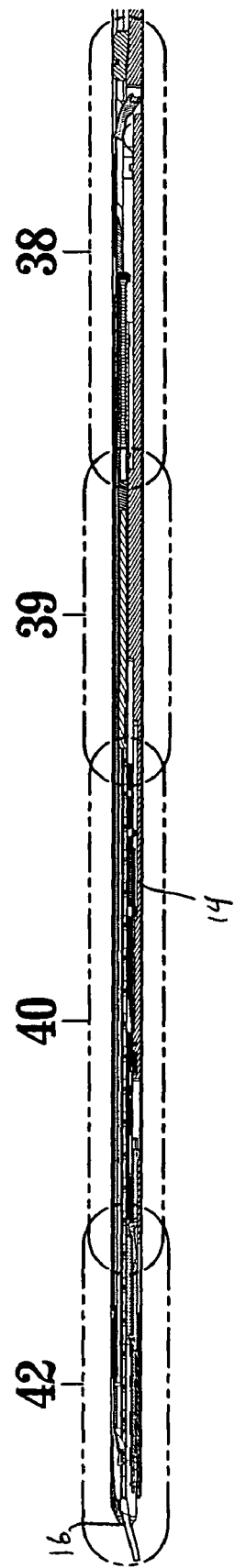
FIG. 37 is an enlarged area of detail of FIG. 35.
Figure 38:
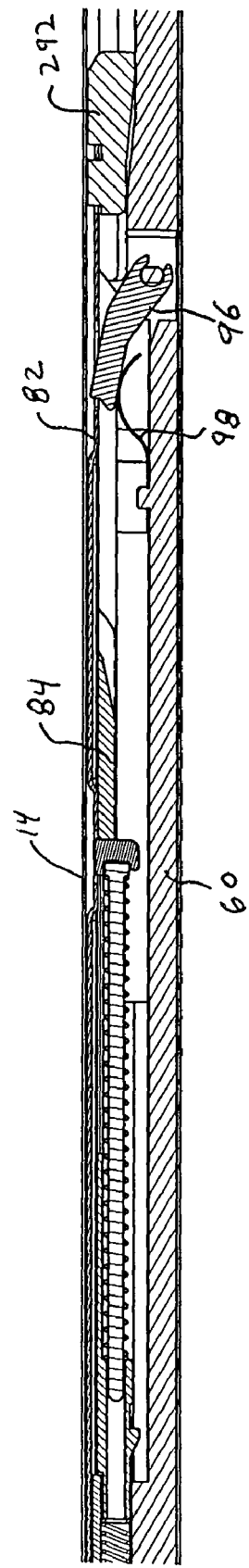
FIG. 38 is in enlarged area of detail of FIG. 37 showing the trip lever.

Referring to FIG. 21, there is a view similar to FIG. 19, however, nose 80 has been removed to illustrate pusher 108 engaging a surgical clip 72 located in channel 70. T-shaped tabs 300 are provided on channel 70 to hold channel cover 78 and nose 80 securely to channel 70.

Referring now to FIG. 22, spindle 60 and associated components are shown with feed bar 82 removed.

Referring to FIG. 23, there are illustrated multiple clips 72 positioned within channel 70 for supply to jaws 16 at a distal end of spindle 60. Clips 72 are arranged in longitudinal alignment within channel 70. Retention fingers 71 are provided at a distal end of channel 70 to restrain a stack of a clips 72 within channel 70 until advanced into jaws 16 by feedbar 82. A lance 302 on channel 70 is configured to engage abutment surface 288 on feed bar 82.

Referring to FIG. 24, there is illustrated an intermediate section of spindle 60 assembled with follower 74 and follower spring 76. As noted, spring 76 biases follower 74 distally relative to spindle 60.

With reference to FIG. 25, there is illustrated spindle 60 assembled with trip lever 96 and biasing spring 98, with trip lever 96 being biased into an upward most position by biasing spring 98. Lockout wedge 292 is positioned within channel 294.

Referring to FIGS. 26 and 27, an opposed side of spindle 60 assembled with driver 66 about jaws 16 is illustrated. As noted above, driver 66 is configured to cam jaws 16 closed about a surgical clip. Thus, jaws 16 include angled camming surfaces 160 for receipt of corresponding camming surfaces 184 (FIG. 34) of driver 66. A pocket 187 (FIG. 31) in the proximal end of jaws 16 limits the retraction of driver 66. Specifically, protrusion 186 of slider joint 68 engages pocket 187 of jaws 16. (See FIGS. 31 & 34).

Referring to FIGS. 28-30, the relative assembled positions of channel 70, trip lock 84, wedge plate 100 and filler component 102 will now be described. Referring initially to FIGS. 29 and 30, filler component 102 is positioned on channel 70. Proximal end of filler component 102 abuts a stop 162 positioned on channel 70. The wedge plate 100 lies over filler component 102 in the manner shown. As best shown in FIG.

30, filler component 102 includes a cam slot 148 having a disengaging edge 150 formed within cam slot 148. Similarly, wedge plate 100 includes a cam slot 136. As noted above, a cam link 104 is provided attached to spindle 60 (not shown) in order to drive wedge plate 100 distally. To facilitate driving wedge plate 100, cam link 104 is provided with a cam link boss 164 which rides in cam slots 136 and 148 of wedge plate 100 and filler component 102 respectively. As cam link 104 is advanced distally relative to wedge plate 100 cam link boss 164 engages a driving edge 166 of wedge plate 100 to drive wedge plate 100 distally. In the manner described hereinafter, once cam link 104, and in particular cam link boss 164, engages disengaging edge 150 of filler component 102 cam link boss 164 is cammed out of engagement of driving edge 166.

Referring to FIG. 30, filler component 102 is provided with a flexible leg 152 which is movable between distal and proximal windows 138, 140, respectively, of wedge plate 100. In order to cam flexible leg 152 out of one of the proximal or distal windows, there is provided a cam surface 168 on flexible leg 152 which cams flexible leg 152 out of the windows in response to relative movement of wedge plate 100 relative to filler component 102.

As noted hereinabove, jaws 16 are provided to receive and crimp surgical clips 72 positioned therein. Referring to FIGS. 31 and 32, jaws 16 generally include a pair of flexible legs 170 fixed to a base 172. Jaw members 16a and 16b are located at a distal end of flexible legs 170. A pair of locking arms 174 extend distally from base 172 and terminate in tabs 176. Tabs 176 are configured to engage corresponding holes 177 on elongated tube 14 (FIG. 10) to secure jaws 16 to elongated tube 14. Jaws 16 include channel 22 for receipt of surgical clips 72. As shown, filler component 102 is positioned directly behind jaws 16 and, as with jaws 16, does not move longitudinally relative to outer tubular member 14.

Referring for the moment to FIG. 32, jaws 16 are configured to receive wedge plate 100 such that the distal tip 134 of wedge plate 100 is used to initially separate jaws section 16a and 16b and maintain them in a separated and aligned configuration during insertion of a surgical clip into jaws 16. As noted, this prevents any torquing or flexing of jaw 16a relative to jaw 16b while a surgical clip 72 is being loaded therein. Each of flexible legs 170 includes a cam edge 178 (see FIGS. 44 & 63) to guide distal tip 134 of wedge plate 100 within jaws 16.

Referring to FIG. 33, wedge plate 100 is illustrated positioned on spindle 60 such that latch retractor 128 extends through a slot 182 in wedge plate 100. As best shown in FIG. 34, with wedge plate 100 removed, it can be seen that a distal end of driver 66 is provided with camming surfaces 184. Camming surfaces 184 cooperate with cam surfaces 160 on jaws 16, (see FIG. 27), to cam jaws 16 together in response to longitudinal movement of driver 66 relative to jaws 16. Protrusion 186 on slider joint 68 extends through a slot 188 in wedge plate 100 to limit retraction of slider joint 68 relative to jaws 16.

The operation of surgical clip applier 10 to crimp a surgical clip around a target tissue, such as, for example, a vessel, will now be described. With reference to FIGS. 35 and 36, trigger 18 is in a generally uncompressed state with rack 202 and thus spindle 60 biased to a proximal most position by return spring 208. Additionally, actuator 242 is in a proximal most position holding counter lever 244 away from counter 246. Pawl 212 is positioned in distal recess 228 on rack 202. As best shown in FIGS. 37-42, and with initial reference to FIG. 38, in an unfired state, trip lever 96 carried by spindle 60, biased upwardly by biasing spring 98, is positioned adjacent to, and in contact with, a slot in feed bar 82. Trip block 84 is in a distal position relative to trip lever 96. Lockout wedge, affixed to feed bar 82, is in a proximal position.

Figure 39:
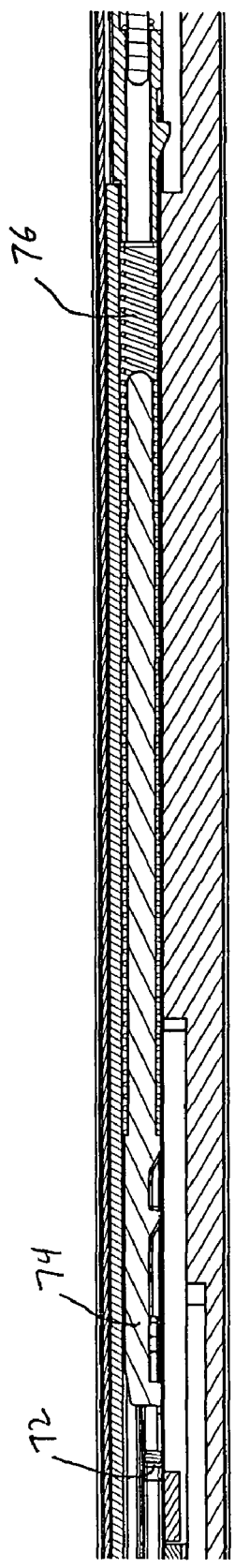
FIG. 39 is an enlarged area of detail of FIG. 37 showing the follower.

Referring to FIG. 39, follower 74 is biased distally by a spring 76 such that clips 72 are biased in a distal direction.

Figure 40:
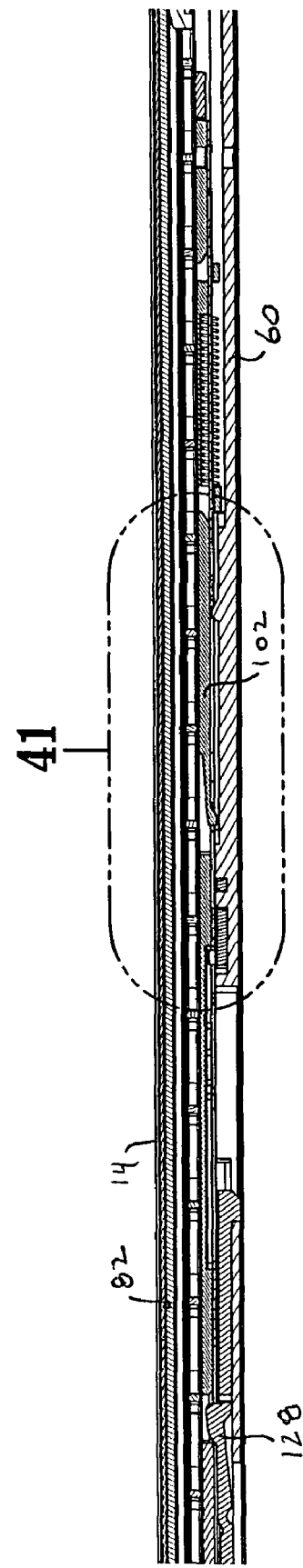
FIG. 40 is an enlarged the area of detail of FIG. 37.

Referring to FIG. 40, spindle 60 and feed bar 82 are stationery with latch retractor 128 biased to an upward position.

Referring to FIG. 41, flexible leg 152 of filler component 102 is in the distal window 138 of wedge plate 100. Raised feature 118 on spindle 60 is proximal of flexible leg 152.

As best shown in FIG. 42, at the distal end of surgical clip applier 10, when at rest in an unfired state, wedge plate 100 and feed bar 82 are in a proximal-most position relative to jaws 16. Pusher 108 is distal of lance 302 (FIG. 42A).

FIGS. 43-47 illustrate the initial at rest position of the wedge plate 100, jaws 16 and filler component 102.

Referring initially to FIGS. 43 and 44, as shown, wedge plate 100 is in a proximal-most position relative to jaws 16. As shown in FIG. 43, flexible leg 152 is in distal window 138 of wedge plate 100, while cam link 104 is in a proximal-most position relative to cam slot 136 in wedge plate 100.

Figure 45:
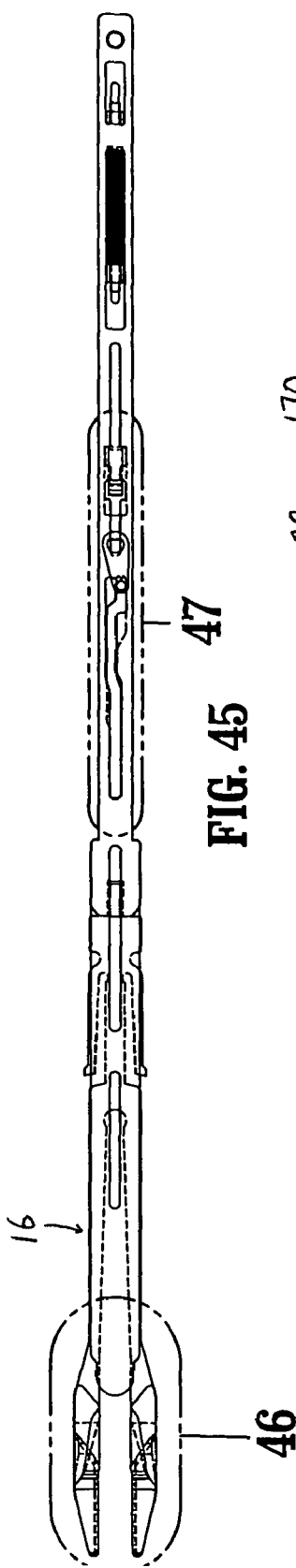
FIG. 45 is a top view of FIG. 43 taken along line 45-45.
Figure 46:
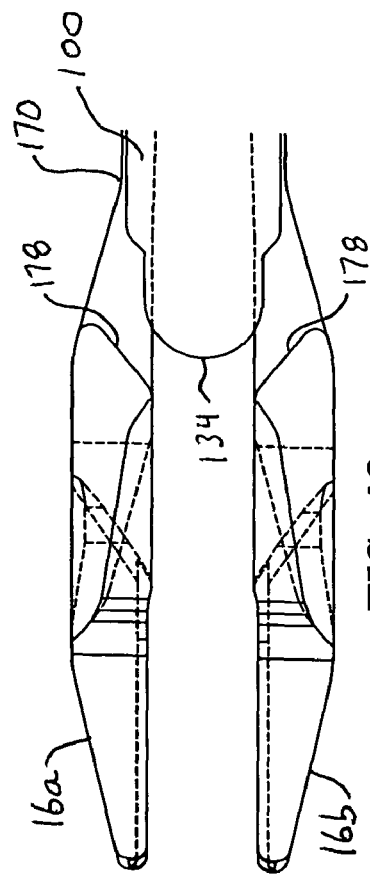
FIG. 46 is an enlarged area of detail of FIG. 45 showing the jaw and the wedge plate.

As best shown in FIGS. 45 and 46, wedge plate 100 is in a proximal most position relative to jaws 16 with distal tip 134 proximal of cam edges 178 of jaws 16.

Figure 47:
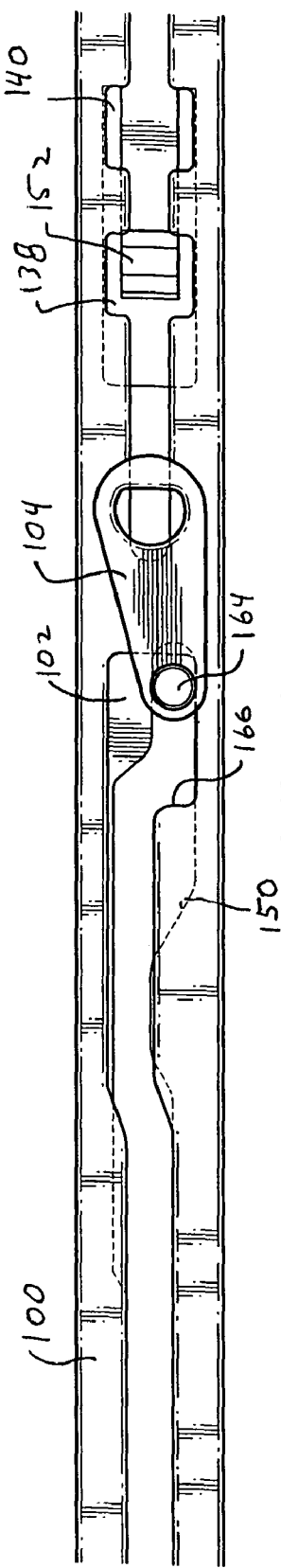
FIG. 47 is an enlarged area of detail of FIG. 45 showing the wedge plate and cam link.

Referring to FIG. 47, wedge plate 100 is in a proximal-most position relative to filler component 102, such that driving edge 166 of wedge plate 100 is proximal of disengaging edge 150 of filler component 102.

Referring to FIG. 48, to initiate actuation of clip applier 10, trigger 18 is moved through an initial swing wishbone link 204 drives rack 202 distally thereby driving spindle 60 distally. Actuator 242 remains in a proximal most position as pin 206 moves through drive slot 252 in actuator 242. With reference for the moment to FIG. 50, if the trigger 18 is released at this point, rack teeth 226 would restrain pawl teeth 222 against proximal motion, preventing release of trigger 18 and partial or inadvertent partial actuation of surgical clip applier 10.

During the initial stroke, spindle 60 moves a predetermined distance. With regard to FIG. 51, as spindle 60 is driven an initial distal distance, trip lever 96 engages elongated window 106 feed bar 82 and moves feed bar 82 distally a similar distance. Lockout wedge 292 is carried distally by feed bar 82. As shown in FIGS. 42 & 51, as feed bar 82 is driven distally and a clip 72 is driven into jaws 16, follower 74 moves distally (FIG. 52) due to the bias of spring 76 to urge the stack of surgical clips 72 distally.

With reference to FIG. 49, as rack 202 moves distally pawl 212 rotates clockwise such that pawl teeth 222 move out of distal recess 228 and begin to ride over rack teeth 226.

Figure 53:
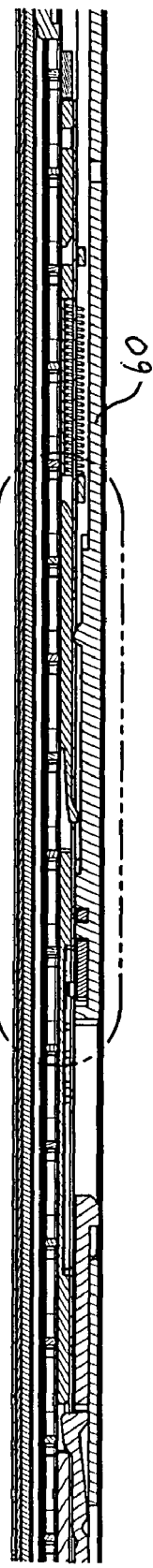
FIG. 53 is a side view, shown in section, of the endoscopic portion of the surgical clip applier.
Figure 54:
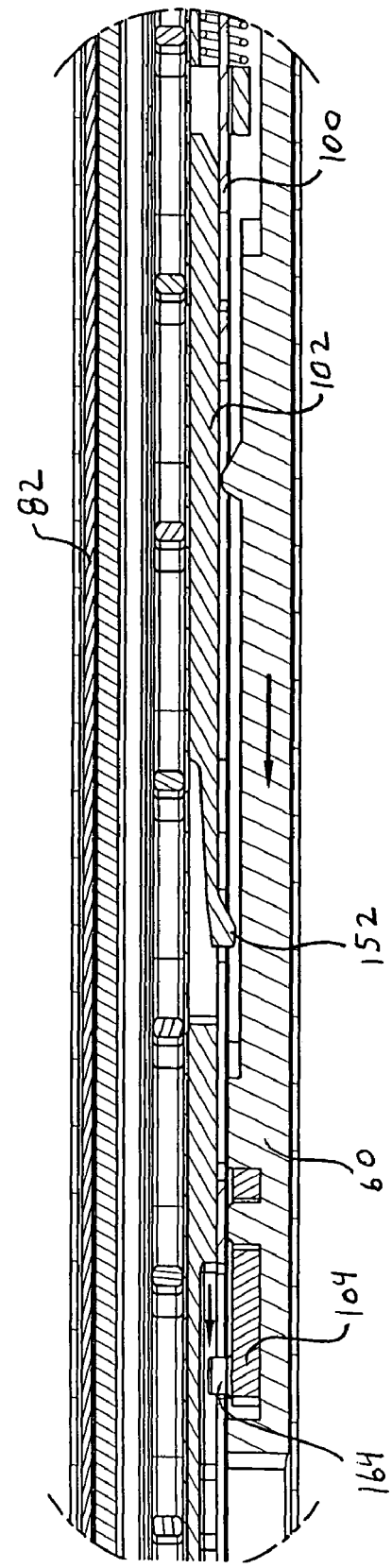
FIG. 54 is an enlarged area of detail of FIG. 53 illustrating the spindle movement.

Referring to FIGS. 53 and 54, as spindle 60 and feed bar 82 move distally, spindle 60 drives cam link 104 distally an initial distance such that cam link boss 164 on cam link 104 engages wedge plate 100. As shown, flexible leg 152 of filler component 102 is positioned in distal-most window 138 of wedge plate 100.

Figure 55:
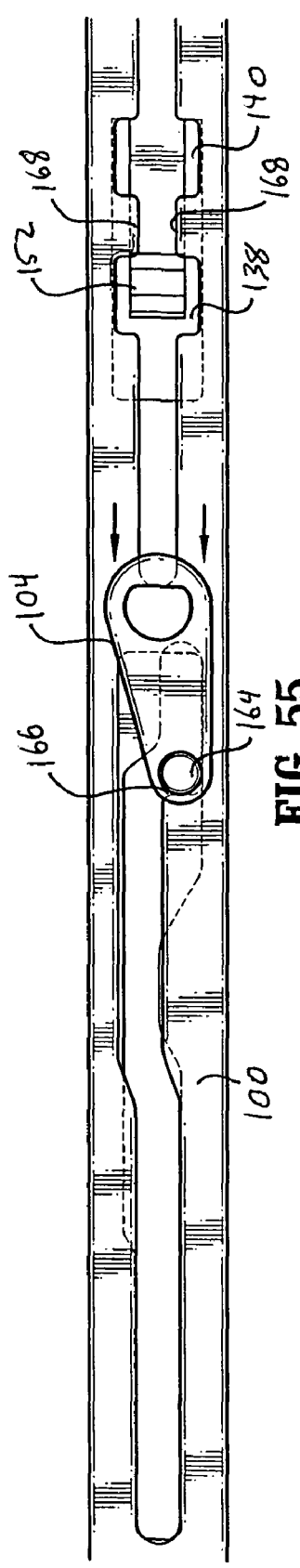
FIG. 55 is a top view of the wedge plate and filler component illustrating the movement of the cam link.

As shown in FIG. 55, as cam link 104 moves distally with spindle 60, cam link boss 164 engages driving edge 166 on wedge plate 100 to urge wedge plate 100 distally relative to filler component 102.

Figure 56:
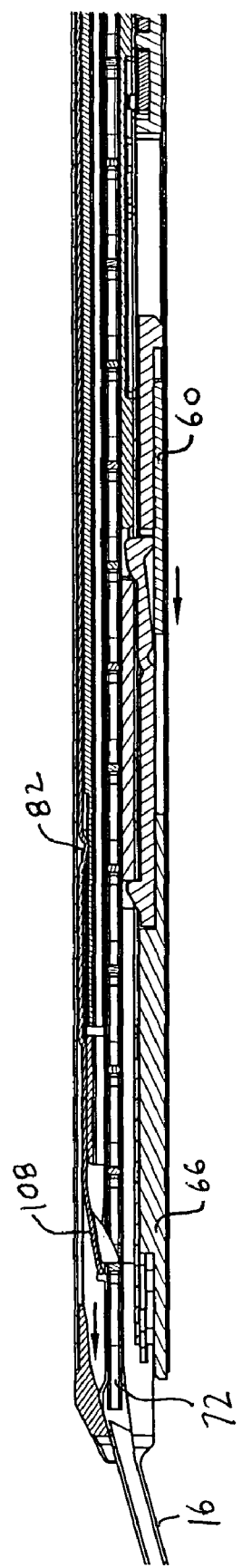
FIG. 56 is a side view, shown in section, illustrating the feed bar advancing a clip.

Referring to FIG. 56, as feed bar 82 moves distally, pusher 108 at the distal end of feed bar 82 engages a clip 72 and begins to urge clip 72 into jaws 16. Notably, at this point, spindle 60 has not yet contacted driver 66, thereby preventing compression of jaws 16 prior to full insertion of surgical clip 72.

Turning again to FIG. 55, as surgical clip applier 10 is actuated through a further second predetermined distance, cam boss 164 on cam link 104 continues to drive wedge plate 100 distally and flexible leg 152 is cammed out of distal window 138 and into proximal window 140 by cam surface 168 to engage wedge plate 100 with filler component 102. As shown in FIGS. 57 & 58, at this point, feed bar 82, wedge plate 100, spindle 60, clips 72 and follower 74 (FIG. 52) are all moving in a distal-most direction.

Figure 59:
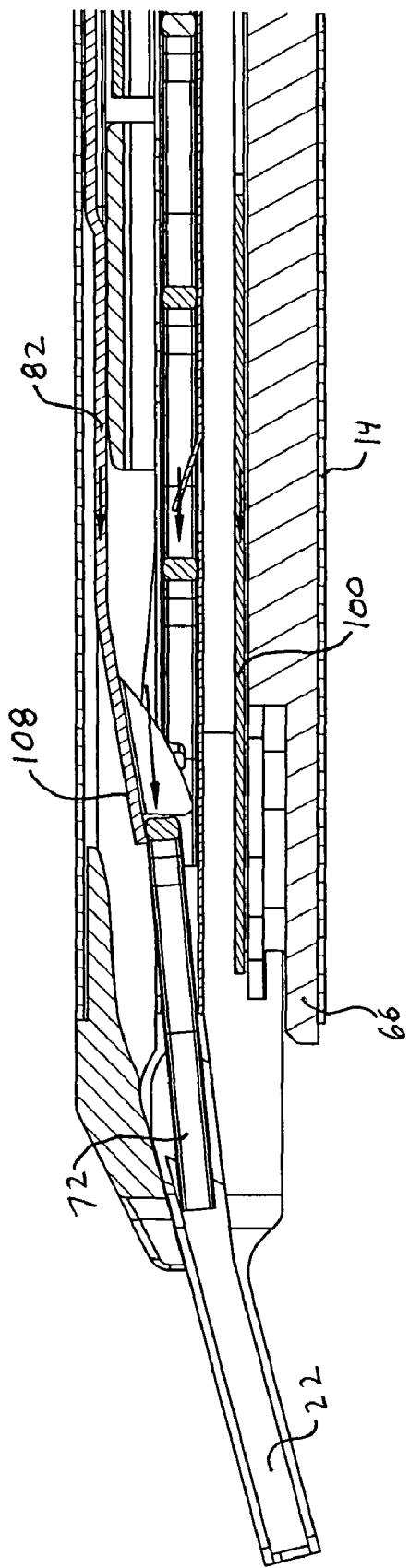
FIG. 59 is a side view, shown in section, illustrating a clip entering the jaws.

Referring to FIG. 59, feed bar 82 continues to urge pusher 108 at the distal end of feed bar 82 against a surgical clip 72 to urge clip 72 into channel 22 in jaws 16. Surgical clips 72 contained in channel 70 are biased in a distal direction by follower 74 (FIG. 52) and wedge plate 100 (FIG. 54) continues to move distally while driver 66 remains stationery relative to elongated tubular member 14.

Figure 60:
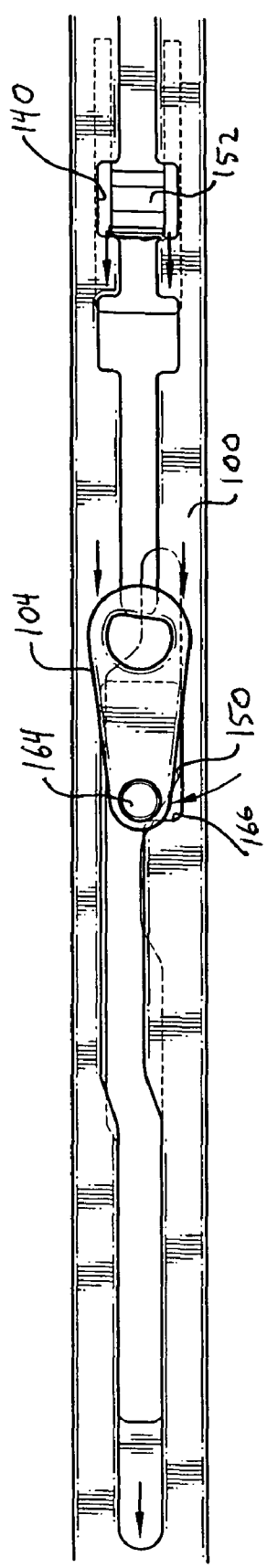
FIG. 60 is a further top view of the cam link and wedge plate movement.

Referring to FIG. 60, as spindle 60 is moved further, cam boss 164 of cam link 104 is cammed out of engagement with driving edge 166 of wedge plate 100 by means of disengaging edge 150 formed in filler component 102 as best shown by the arrows in FIG. 60. During this further stroke of a predetermined distance, flexible leg 152 of filler component 102 snaps into proximal window 140 of wedge plate 100, thereby preventing retraction of wedge plate 100 from its distal-most position.

Figure 61:
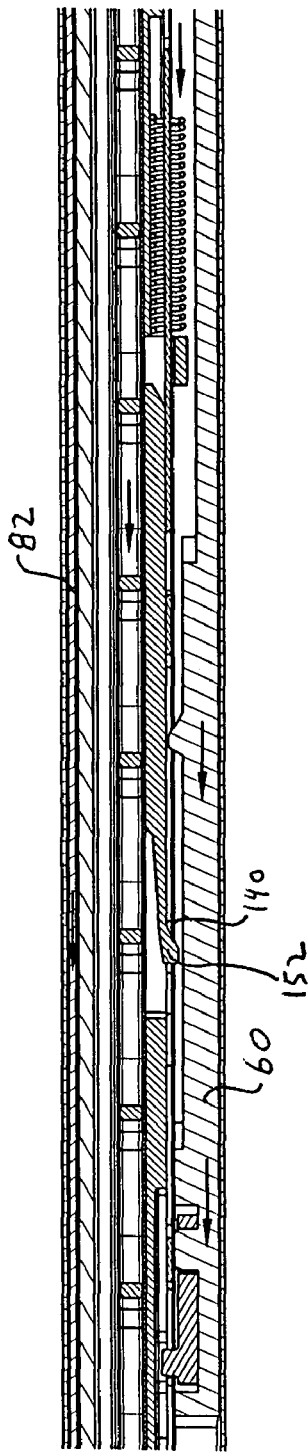
FIG. 61 is a side view, shown in section, of the flexible leg and wedge plate disengagement

As shown in FIG. 61, flexible leg 152 is positioned within proximal window 140 of wedge plate 100, thereby restraining wedge plate 100 against retraction, while feed bar 82 and spindle 60 continue to move in a distal direction as shown by the arrows.

Figure 63:
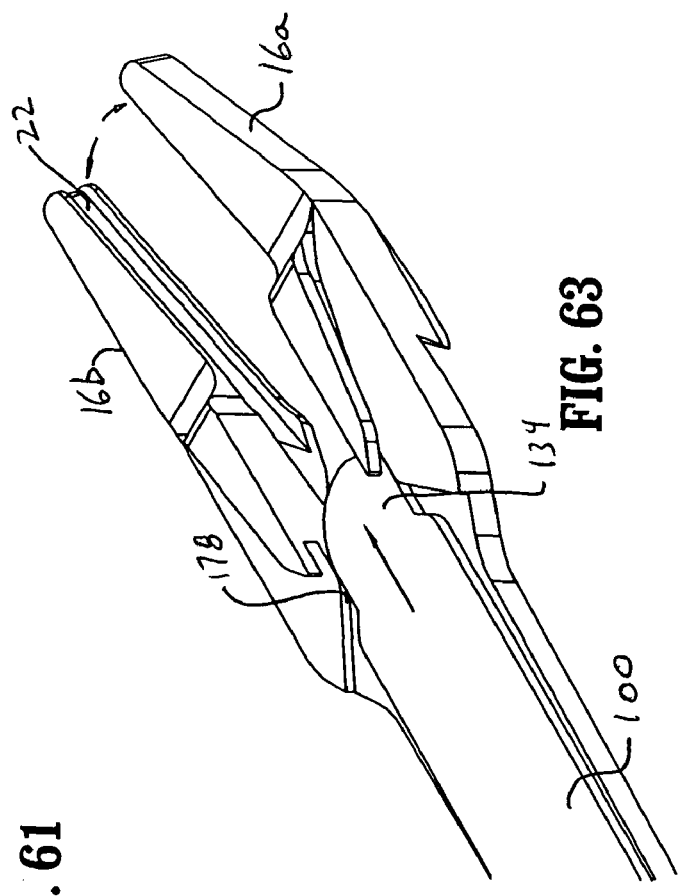
FIG. 63 is a perspective view illustrating the wedge plate camming open the jaw structure.
Figure 62:
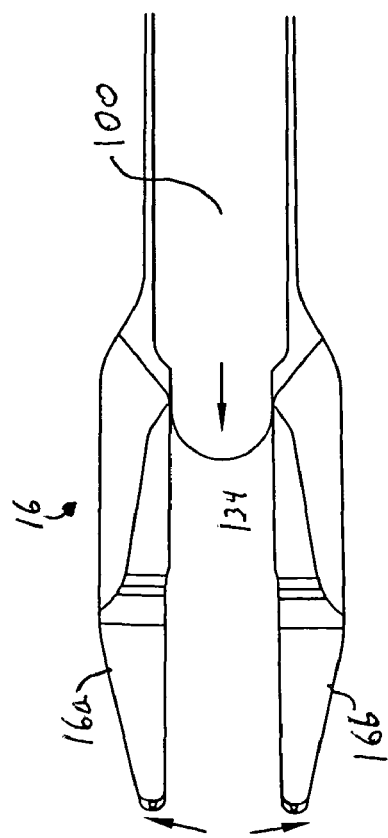
FIG. 62 is a top view of the wedge plate entering the jaw structure.

As shown in FIGS. 62-63, distal tip 134 of wedge plate 100 urges jaw members 16a and 16b apart by engaging cam surfaces 178 in jaw members 16a and 16b. As noted above, by positioning wedge plate 100 in cam surfaces 178 of jaw members 16a and 16b, wedge plate 100 not only spreads the jaws 16 apart to properly receive surgical slip 72, but additionally restrains each individual jaw member 16a and 16b from flexing with respect to each other, thereby preventing any torque of clip 72 as it is being inserted into jaws 16.

Figure 64:
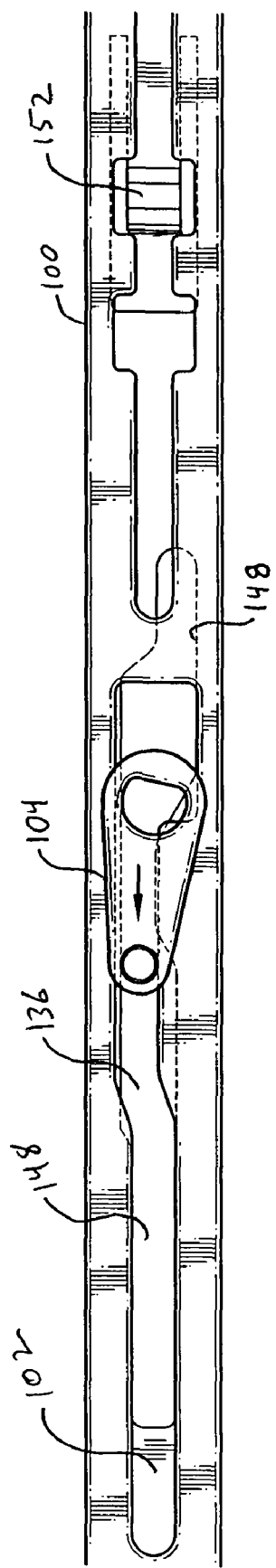
FIG. 64 is a top view illustrating further advancement of the cam link in the wedge plate.

Referring to FIG. 64, as noted above, flexible leg 152 restrains wedge plate 100 from proximal retraction while cam link 104 continues to advance through slots 148 and 136 in filler component 102 and wedge plate 100 (FIG. 64).

Figure 65:
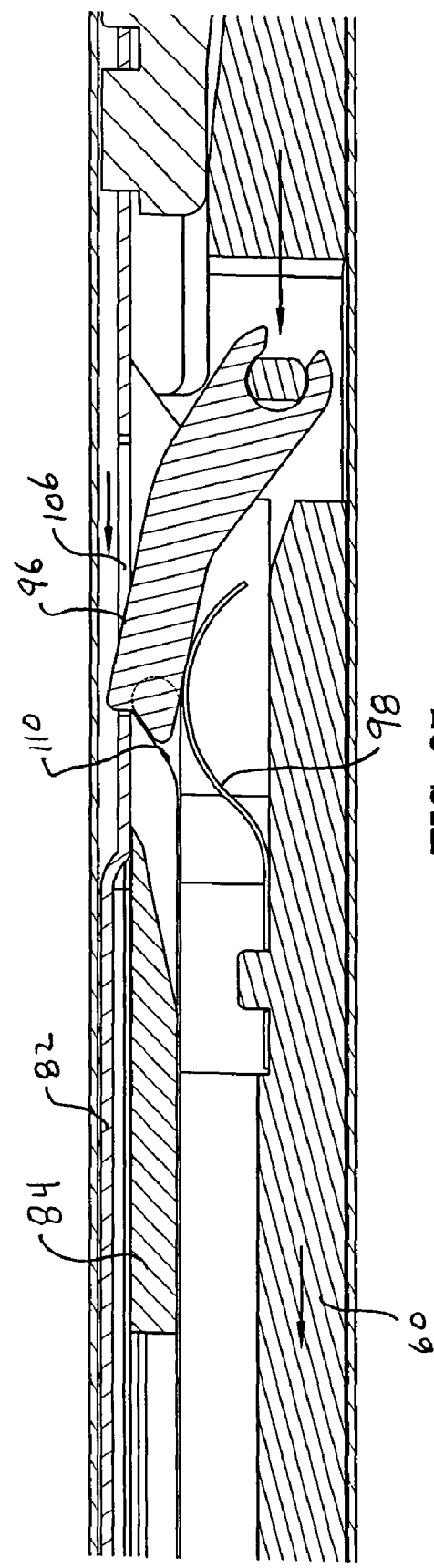
FIG. 65 is a side view, shown in section, illustrating the trip lever engaged with the feed bar.

As best shown in FIG. 65, as spindle 60 continues to move distally through the stroke, trip lever 96 is urged distally with spindle 60 until trip lever 96 engages camming surface 110 (See FIG. 10D) of trip block 84. As camming surface 110 (FIG. 10D) of trip block 84 is urged against trip lever 96, trip lever 96 will be cammed out of engagement with elongated window 106 of feed bar 82 allowing feed bar 82 to return to a proximal position due to the bias of feed bar spring 88 (see FIG. 10).

Figure 66:
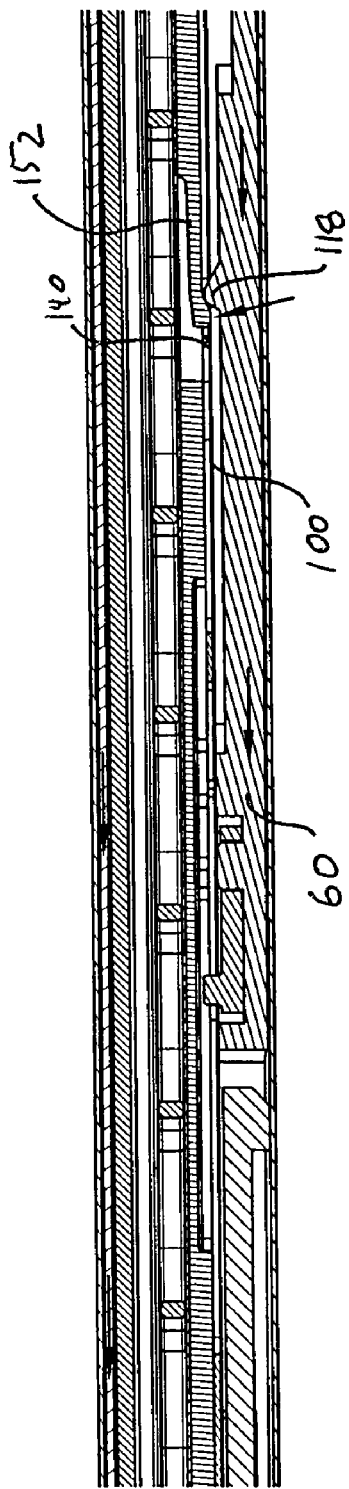
FIG. 66 is a side view, shown in section, illustrating the spindle camming the flexible leg out of engagement with the wedge plate.
Figure 67:
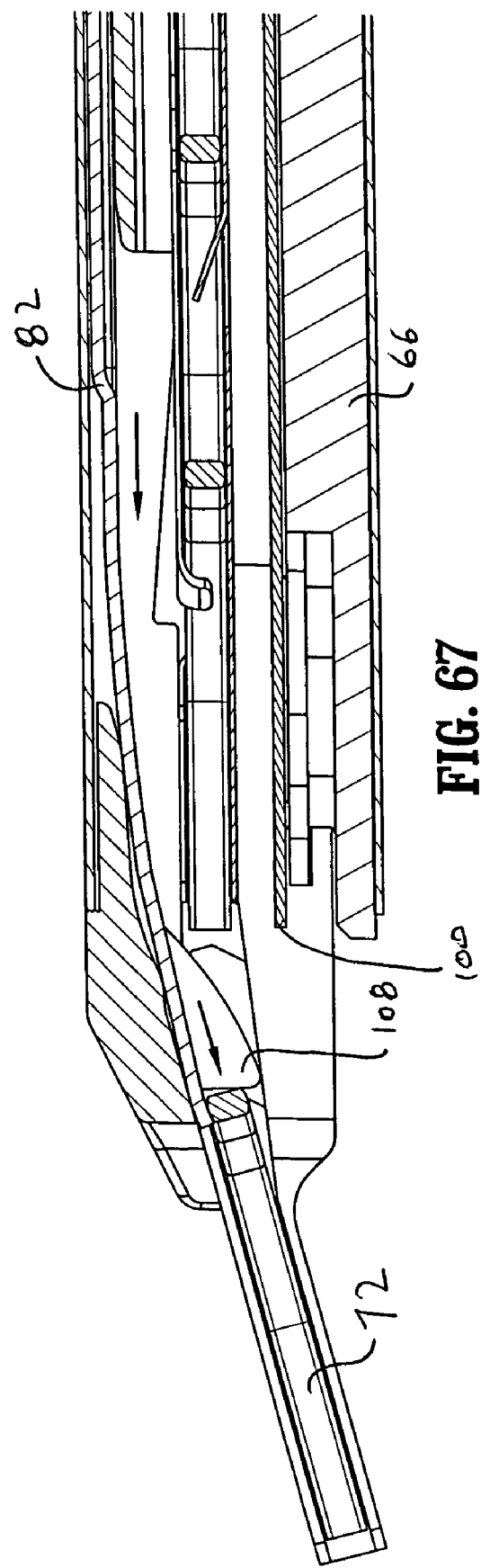
FIG. 67 is a side view, shown in section, illustrating the feed bar loading a clip into the jaw structure.

Referring for the moment to FIG. 66, as spindle 60 continues to move through its stroke, raised feature 118 on spindle 60 begins to cam flexible leg 152 out of proximal window 140 of wedge plate 100, so that the wedge plate 100 will be able to retract prior to, and so that, surgical clip 72 is crimped between jaws 16. This is best illustrated in FIG. 67 where feed bar 82 has fully inserted clip 72 within jaws 16 and wedge plate 100 has retracted to a proximal-most position.

Figure 68:
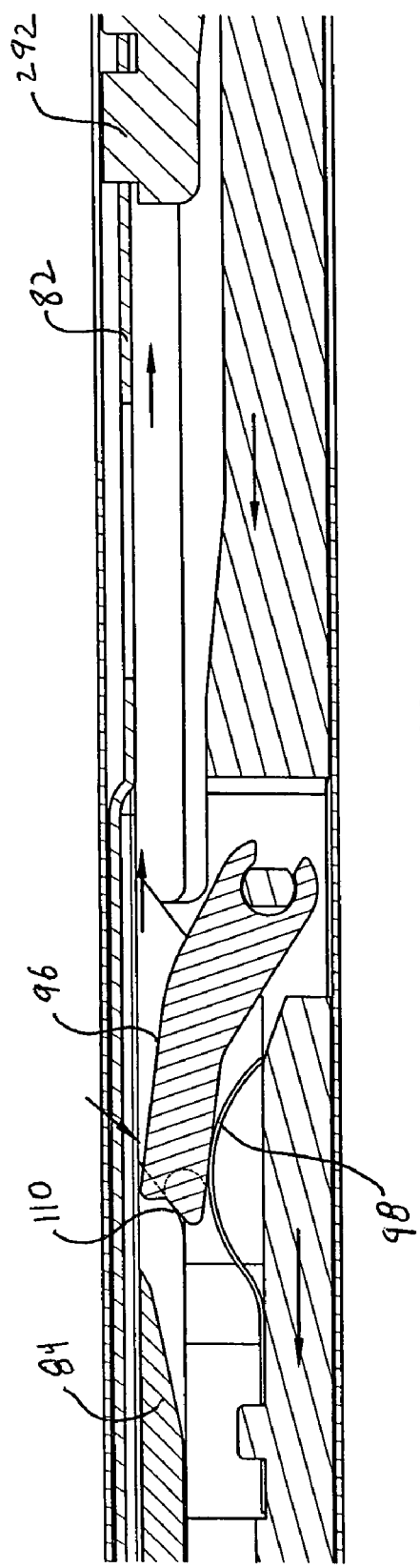
FIG. 68 is a side view, shown in section, illustrating the trip lever being cammed out of engagement with the feed bar by means of a trip block.
Figure 69:
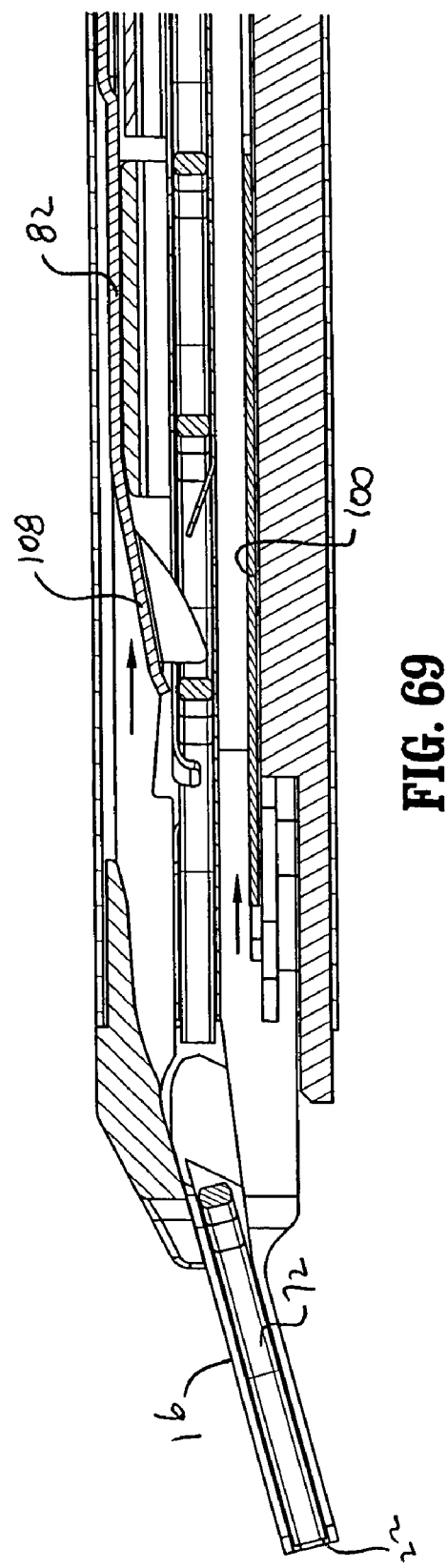
FIG. 69 is a side view, shown in section, illustrating the retraction of the wedge plate and feed bar.

FIG. 68 illustrates trip lever 96 being cammed out of engagement with feed bar 82 by camming surface 110 of trip block 84 and against the bias of biasing spring 98 such that feed bar 82 is disengaged from trip lever 96 and feed bar 82 can start to retract proximally. As shown, in FIG. 69, pusher 108 of feed bar 82 is retracted to a proximal position behind the next distal-most clip 72 as wedge plate 100 retracts leaving clip 72 inserted into jaws 16.

Figure 69A:
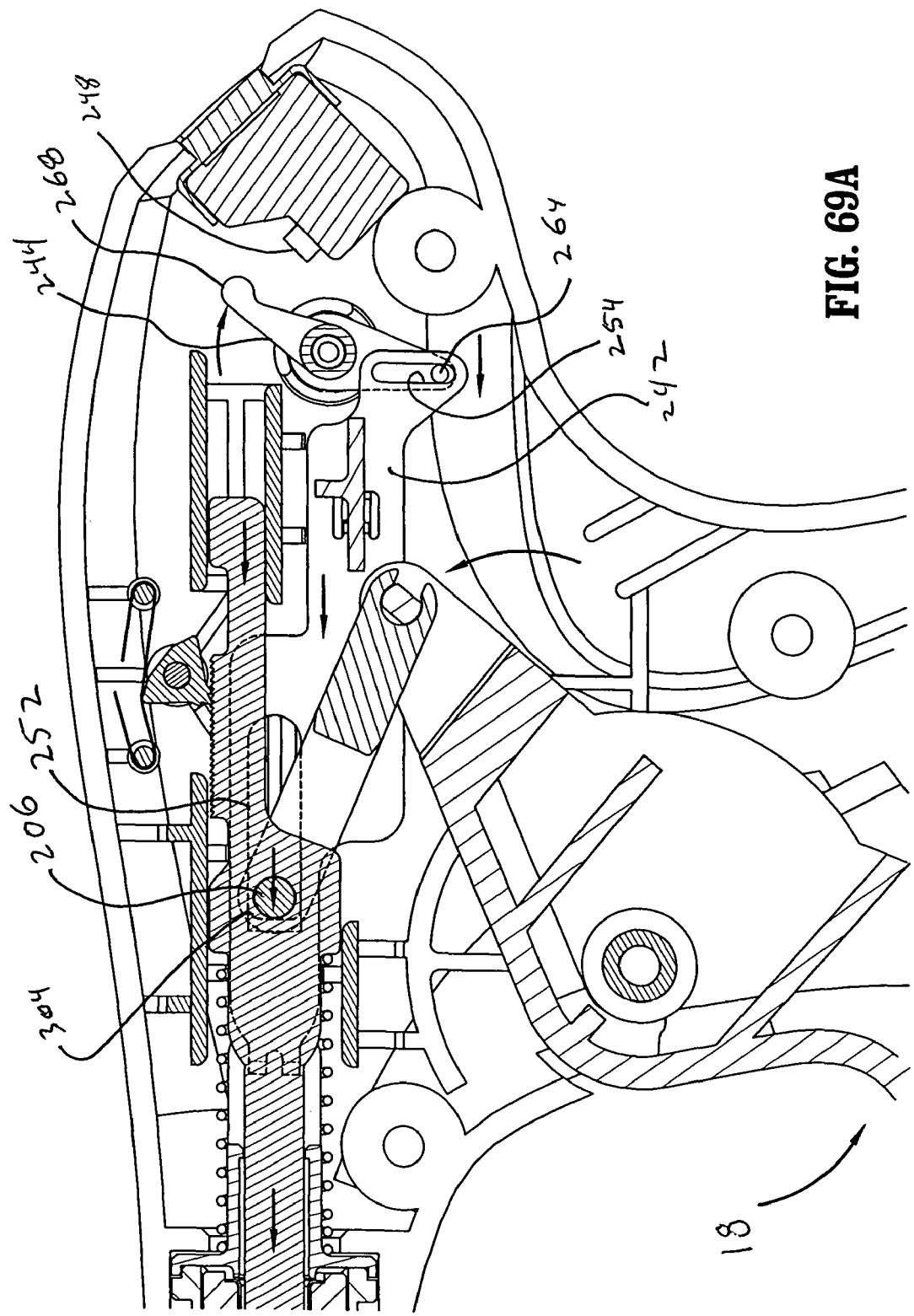
FIG. 69A is a perspective view, with half the body removed, illustrating initial actuation.

Referring to FIG. 69A, as trigger 18 is continued to be compressed, pin 206 advances distally within drive slot 252 on actuator 242 until pin 206 engages a distal end 304 of drive slot 252. Thereafter, as trigger 18 is further compressed, pin 206 moves actuator 242 distally. Pin 264 on toggle arm 244 is rotated clockwise within connecting slot 254 thereby driving contact arm 268 on toggle arm 244 towards actuation feature 248.

Figure 70:
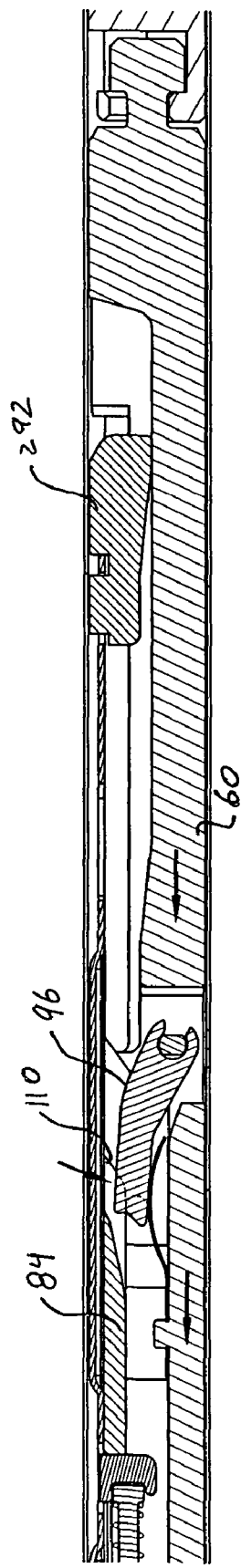
FIG. 70 is a side view, shown in section, illustrating further advancement of the spindle.

Referring to FIG. 70, trip lever 96 is completely cammed down by cam surface 110 on trip block 84 and spindle 60 continues to move distally through a further predetermined stroke.

Figure 71:
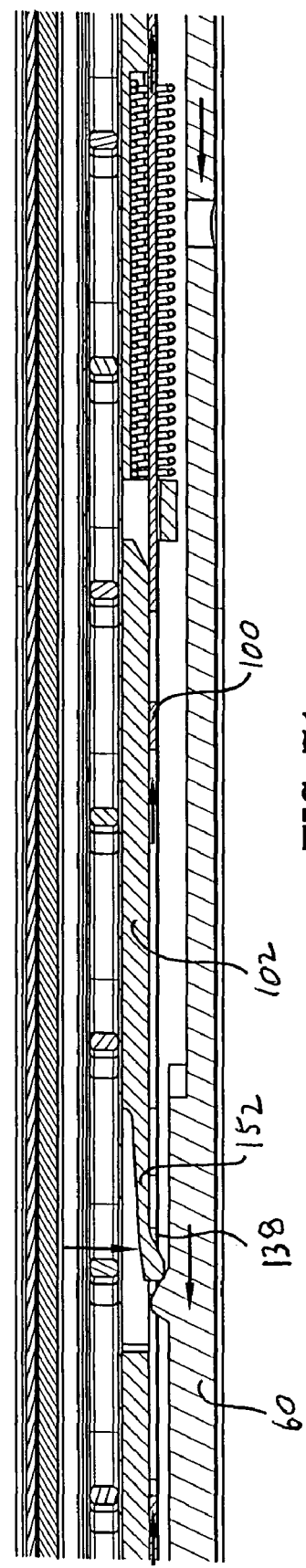
FIG. 71 is a side view, shown in section, illustrating the retraction of the wedge plate and further advancement of the spindle.
Figure 72:
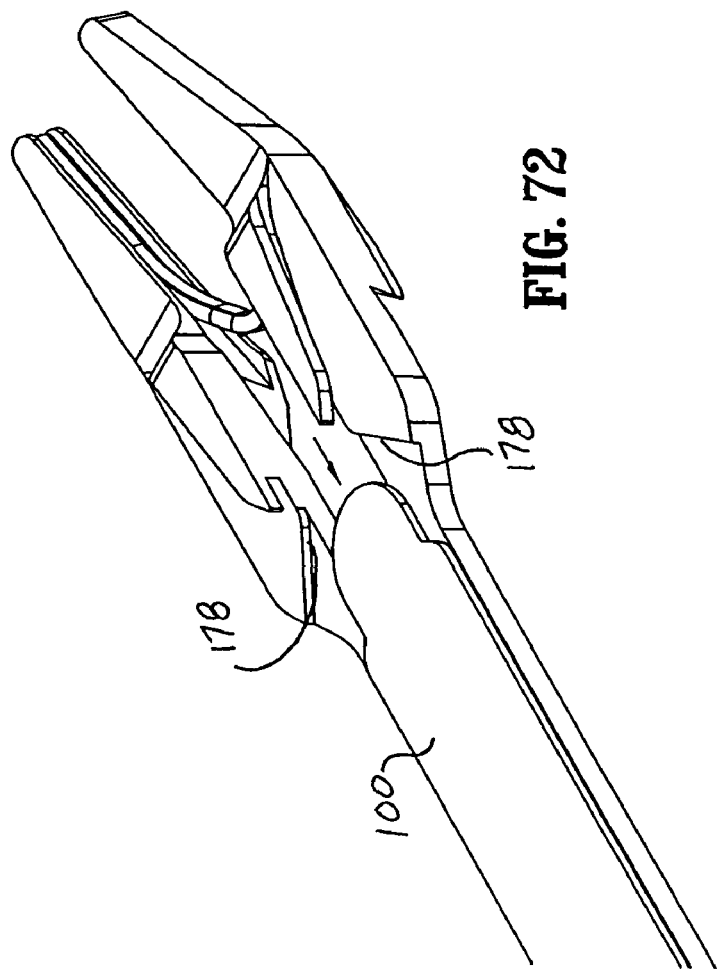
FIG. 72 is a perspective view of the wedge plate retracting from the jaw structure.

Referring for the moment to FIG. 71, as wedge plate 100 retracts proximally while spindle 60 continues to move distally, flexible leg 152 on filler component 102 snaps into distal window 138 of wedge plate 100. As shown in FIG. 72, wedge plate 100 is retracted to a proximal position relative to jaws 16.

Figure 73:
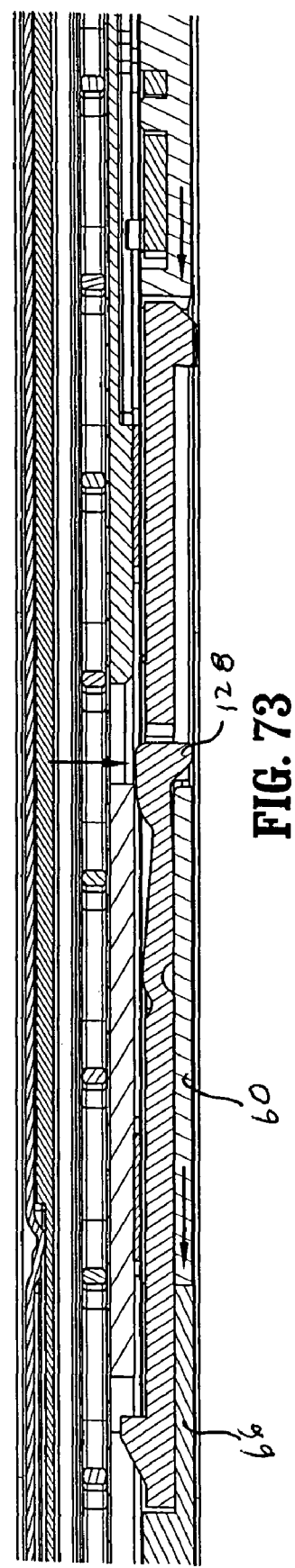
FIG. 73 is a side view, shown in section, with the spindle engaging the driver and a latch retractor engaging the spindle.

Referring to FIG. 73, when latch retractor 128 is cammed downwardly relative to spindle 60, spindle 60 has moved distally to a predetermined distance. The action of spindle 60, now engaging driver 66, pushes driver 66 distally. Driver 66 draws slider joint 68 and simultaneously slider joint 68 drags latch retractor 128 distally mechanically forcing cam surface no. of latch retractor 128 downward to underside of jaw pad 172 and engaging latch retractor 128 with slot 126 of spindle 60.

Referring to FIGS. 74-75, as trigger 18 is fully compressed to drive spindle 60 to a distal-most position, upon complete compression of trigger 18 and fully forming of clip 72, and with reference to FIG. 74, counter lever is fully rotated clockwise driving bumper 268 against counter button 248 to thereby increment the number displayed by counter 246.

As noted hereinabove, the incrementation of the number illustrated in counter 246 can be either down from a full complement of surgical clips 72 contained within an original surgical stapler 10 or can be counted up to indicate the number of clips dispensed by surgical instrument 10.

Referring for the moment to FIG. 75, on full firing of surgical instrument 10, pawl teeth 222 disengage from rack teeth 226 and reside within proximal recess 230. Notably, a full stroke of the spindle 60 is required to take a clip 72 from an initial position to a fully inserted position in the jaws 16. As spindle 60 moves through its distal-most position, it moves driver 66 in the manner described hereinabove to crimp a surgical clip 72. For example, referring to FIGS. 76-79, driver 66 advances distally relative to camming surfaces 160 on jaws 16a and 16b, such that camming surfaces 184 on driver 66 cam jaws 16a and 16b closed thereby closing surgical clip 72 contained therebetween.

Figure 80:
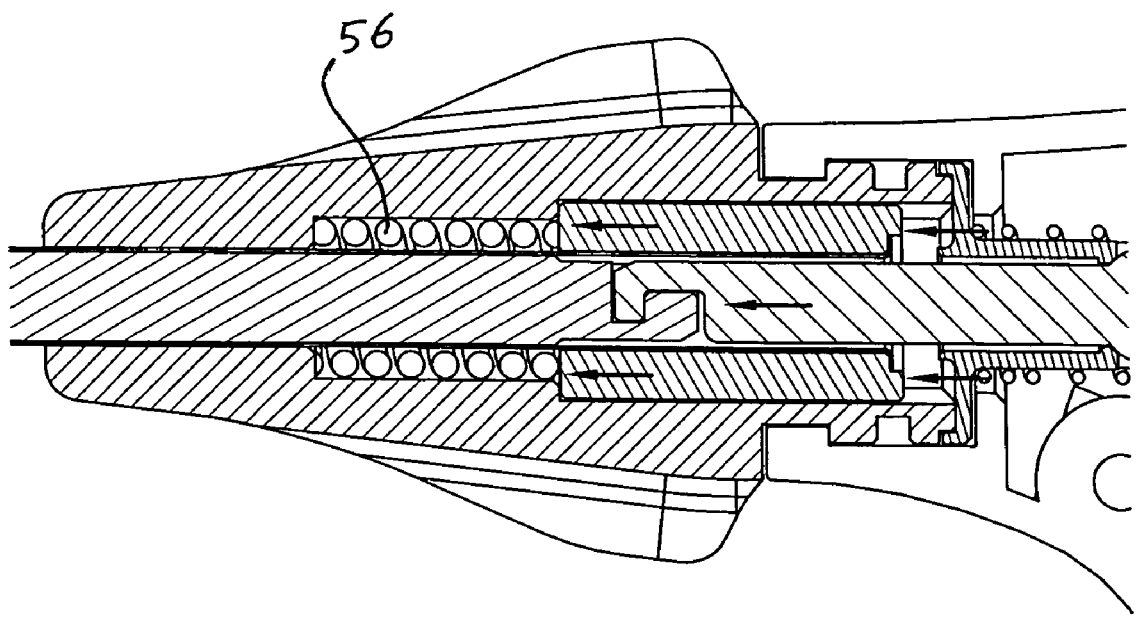
FIG. 80 is a view, shown in section, of the overpressure mechanism including the impact spring.

Referring for the moment to FIG. 80, a security mechanism is provided to prevent an overstroke condition and thereby excessive compression of clip 72 from damaging tissue, jaws 16 or driver 66. If trigger 18 is continued to be squeezed past a stroke required for a full forming of clip 72 impact spring 56 compresses within the space defined between knob 20 and bushing 48 thereby preventing any further distal movement of spindle 60.

Figure 81:
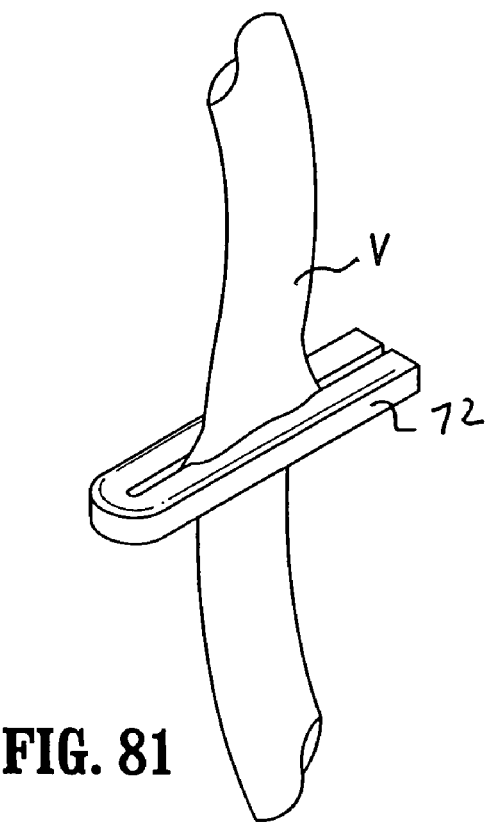
FIG. 81 is a perspective view of a surgical clip formed on a vessel.

A fully formed clip formed about vessel V is illustrated in FIG. 81.

Figure 82:
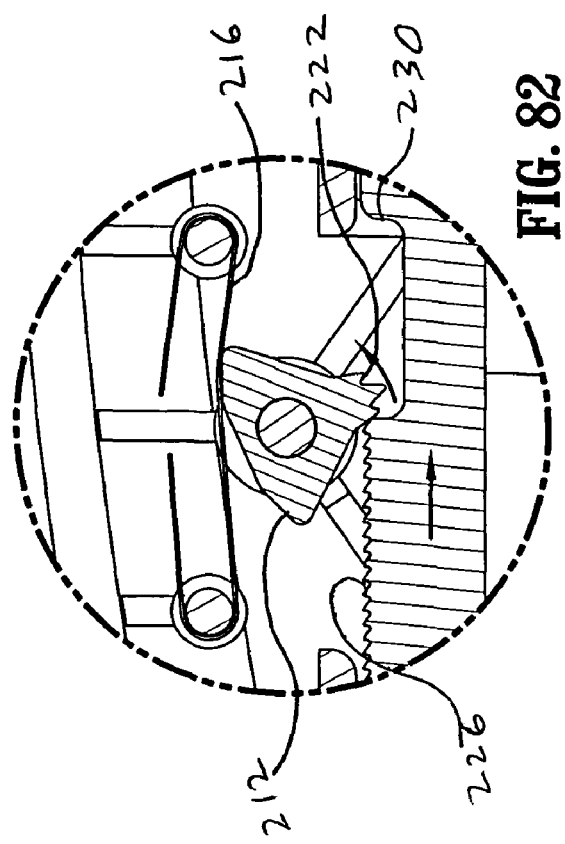
FIG. 82 is an enlarged area of detail of the pawl resetting.
Figure 83:
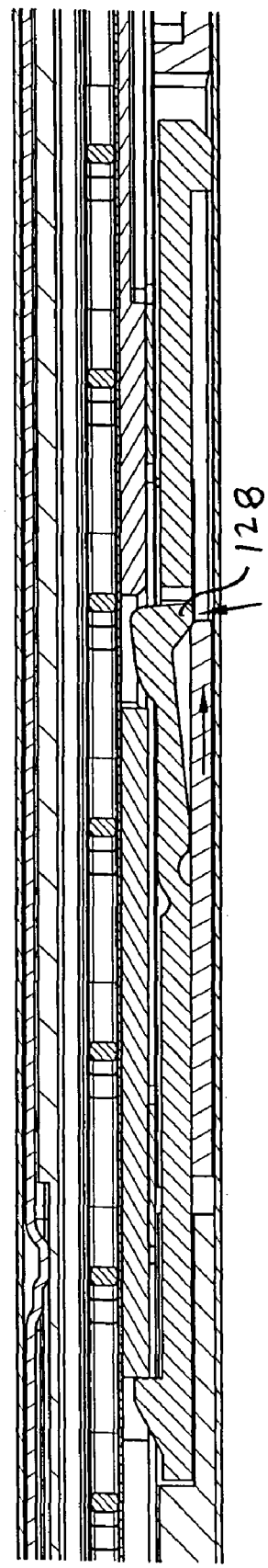
FIG. 83 is a side view, shown in section, illustrating the latch retractor resetting.

Referring to FIG. 82, as trigger 18 is released (not shown), pawl 212 now rotates counter-clockwise against the bias of pawl spring 216 such that pawl teeth 222 ride along rack teeth 226 to reset the handle assembly. As shown in FIG. 83, when driver 66 retracts, latch retractor 128 is again biased up into its upper-most position, thereby, resetting the drive mechanism.

Figure 84:
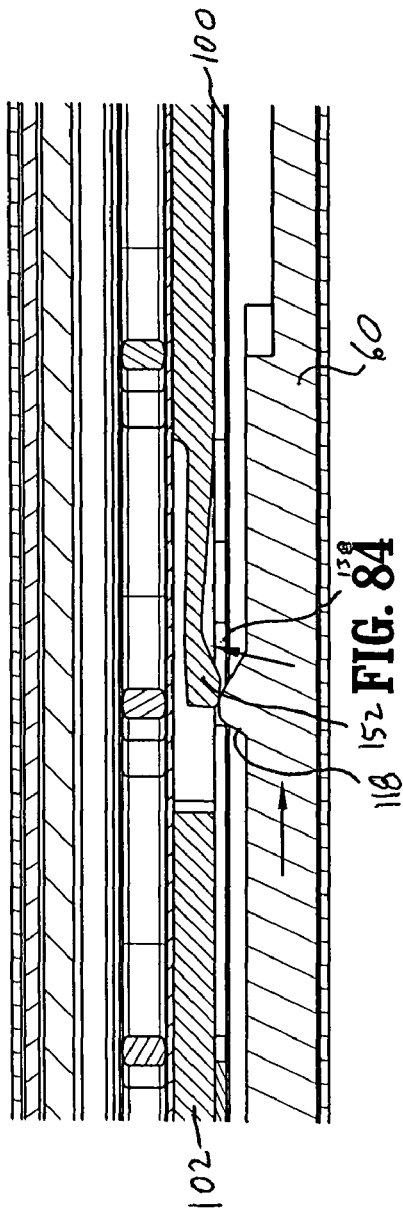
FIG. 84 is a side view, shown in section, illustrating the spindle retracting.
Figure 85:
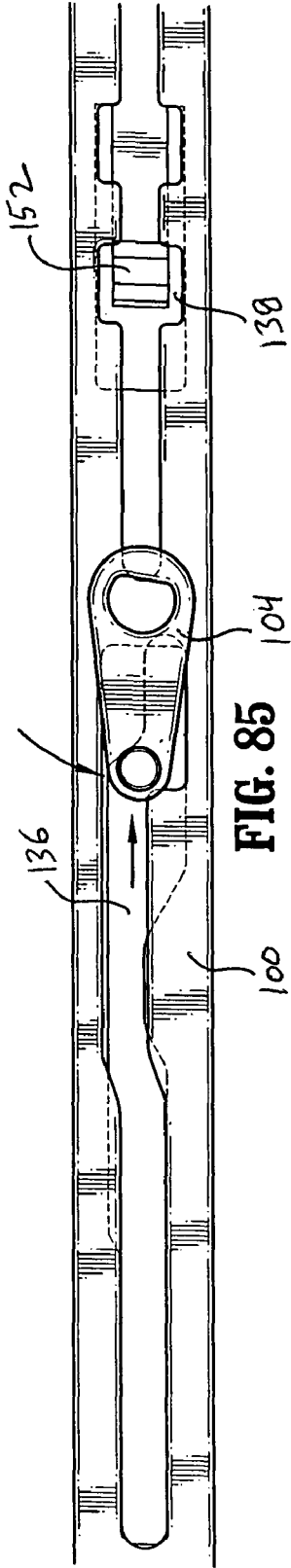
FIGS. 85 and 86 are top views illustrating the cam link resetting within the wedge plate.
Figure 86:
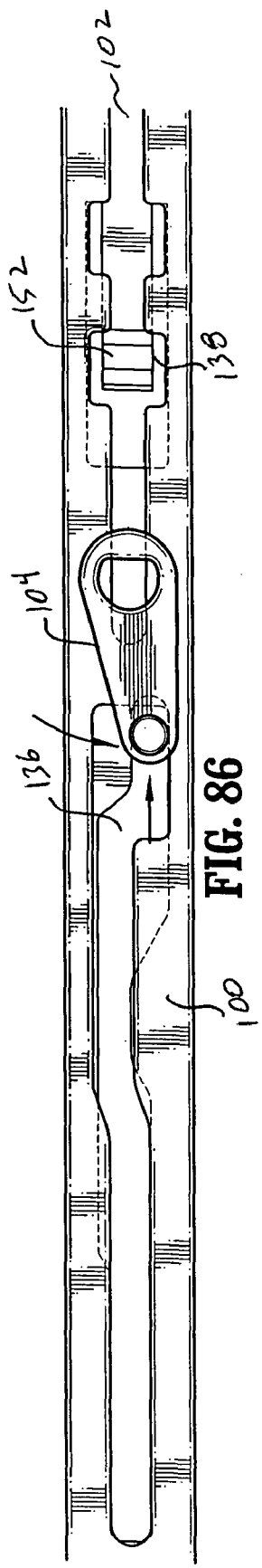

Referring to FIGS. 84-86, as spindle 60 retracts, raised feature 118 of spindle 60 moves past flexible leg 152 in filler component 102. It should be noted that wedge plate 100 does not move as it has already fully retracted. As spindle 60 retracts, it draws cam link 104 proximally within slots 136 and 148 of wedge plate 100 and filler component 102 to its initial position. As best seen in FIG. 86, in this position, clip applier 10 is again in an initial position to be refired and thus to attach another clip to a vessel.

Figure 87:
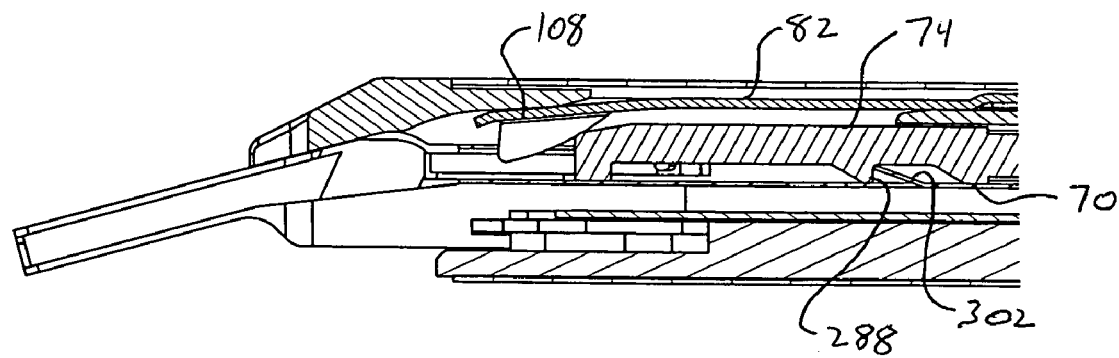
FIG. 87 is a side view of the distal end of the surgical clip applier illustrating the follower engagement with a lance.
Figure 88:
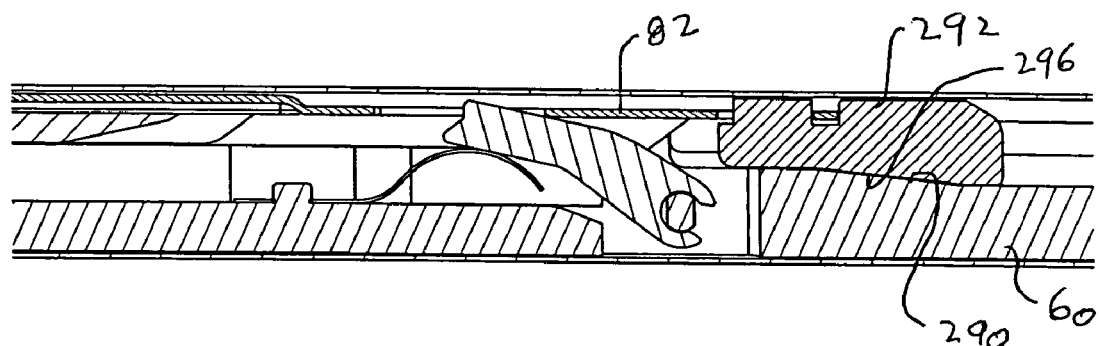
FIG. 88 is a side view, partially showing section, of the lockout wedge engagement with the spindle.
Figure 89:
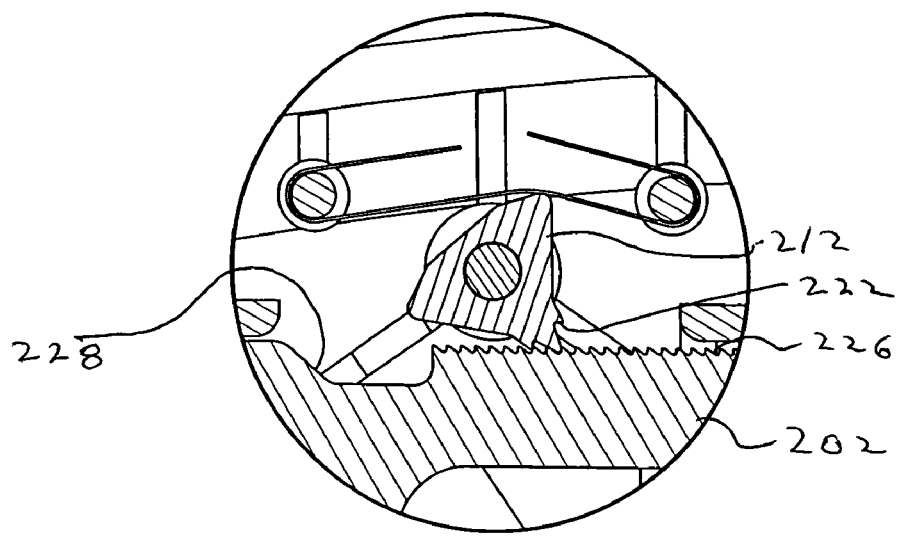
FIG. 89 is a enlarged view of the pawl and rack in a locked out condition.

Referring now to FIGS. 87 to 89 with initial reference to FIG. 87, once all surgical clips 72 have been discharged from surgical clip applier 10, follower 74 is in a distal-most position such that abutment surface 288 engages lance 302 on channel 70 thereby locking out or preventing proximal retraction of follower 74. As shown, pusher 108 on feed bar 82 upon retraction engages follower 74 and wedges between nose 80 and follower 74 such that feedbar 82 cannot retract proximally.

As shown in FIG. 88, since feed bar 82 is restrained in a distal-most position, lockout wedge 292, affixed to feed bar 82, is also restrained in a distal-most position. Thus, as spindle 60 attempts to retract proximally, angled surface 296 on lockout wedge 292 engages angled surface 290 on spindle 60 thereby preventing further retraction of spindle 60.

Referring to FIG. 89, because spindle 60 cannot retract completely proximally rack 202 cannot retract completely proximally. Rack teeth 226 engage pawl teeth 222 and prevent pawl 212 from rotating back into distal recess 228 thereby preventing resetting of the clip applier 10. In this manner, clip applier 10 is completely locked out from any further attempted firings after the last surgical clip 72 has been dispensed. Because pawl teeth 222 and rack teeth 226 prevent any distal movement of the drive mechanism, specifically trigger 18 is prevented from being squeezed further.

What is claimed is:

1. An apparatus for application of surgical clips to body tissue, which comprises:
    a) a handle portion;
    b) a body extending distally from the handle portion and defining a longitudinal axis;
    c) a plurality of surgical clips disposed within the body;
    d) a jaw assembly mounted adjacent a distal end portion of the body, the jaw assembly including first and second jaw portions movable between a spaced-apart and an approximated position;
    e) a feed bar configured to individually distally advance a surgical clip to the jaw assembly while the jaw portions are in the spaced apart position;
    f) an actuation mechanism at least partially disposed within the body and longitudinally movable in response to actuation of the handle portion, the actuation mechanism including a first angled surface;
    g) a jaw closure member positioned distally of the actuation mechanism and adjacent the first and second jaw portions to move the jaw portions to the approximated position upon longitudinal movement of the actuation mechanism; and
    h) a lockout mechanism directly and fixedly connected to the feed bar, the lockout mechanism including a second angled surface and being configured and dimensioned to cooperatively engage the first angled surface of the actuation mechanism, wherein re-actuation of the apparatus is prevented upon engagement of the first angled surface and the second angled surface and subsequent to the application of a final surgical clip.

2. The apparatus of claim 1, wherein the lockout mechanism includes a wedge member disposed within the body, the wedge member being longitudinally movable through the body between a proximal-most position and a distal-most position.

3. The apparatus of claim 2, wherein the first and second angled surfaces are in engagement when the wedge member is in the distal-most position such that proximal retraction of the actuation mechanism is substantially prevented.

4. The apparatus of claim 1, further comprising a follower disposed proximally of the plurality of surgical clips and being adapted to urge the plurality of surgical clips distally.

5. The apparatus of claim 4, wherein the follower is longitudinally movable between a proximal-most position and a distal-most position and includes an abutment surface, the abutment surface being configured to engage a protrusion when the follower is in the distal-most position such that proximal retraction of the follower is substantially prevented.

6. The apparatus of claim 5, wherein the feed bar includes a pusher, the pusher being configured to engage the follower upon retraction of the feed bar relative to the follower such that retraction of the feed bar is substantially prevented.

7. An apparatus for application of surgical clips to body tissue, which comprises:
    a) a handle portion;
    b) a body extending distally from the handle portion and defining a longitudinal axis;
    c) a plurality of surgical clips disposed within the body;
    d) a jaw assembly mounted adjacent a distal end portion of the body, the jaw assembly including first and second jaw portions movable between a spaced-apart and an approximated position;
    e) a feed bar configured to releasably engage a surgical clip to individually distally advance the surgical clip to the jaw assembly while the jaw portions are in the spaced apart position, wherein subsequent to the application of a final surgical clip a pusher of the feed bar is wedged between a distal-most surface of a clip follower and an inner surface of the body, such that the feed bar is prevented from proximal retraction to prevent re-actuation of the apparatus;
    f) an actuation mechanism at least partially disposed within the body and longitudinally movable in response to actuation of the handle portion; and
    g) a jaw closure member positioned distally of the actuation mechanism and adjacent the first and second jaw portions to move the jaw portions to the approximated position upon longitudinal movement of the actuation mechanism.

8. The apparatus of claim 7, wherein the pusher of the feed bar has a distal end that is configured to advance an individual clip such that the individual clip is positioned between the first and second jaws.

9. The apparatus of claim 8, wherein the pusher is affixed to a distal end of the feed bar.

10. The apparatus of claim 8, further comprising a disposed proximally of the plurality of surgical clips and adapted to urge the plurality of surgical clips distally.

11. The apparatus of claim 10, wherein the clip follower is longitudinally movable between a proximal-most position and a distal-most position, the clip follower including an abutment surface configured to engage a protrusion when the clip follower is in the distal-most position such that proximal retraction of the clip follower is substantially prevented.

12. The apparatus of claim 11, wherein a proximal end of the pusher is configured and dimensioned to engage a distal end of the clip follower upon retraction of the feed bar relative to the follower such that retraction of the feed bar is substantially prevented.

* * * * *